US005683904A

United States Patent [19]
Baker et al.

[11] Patent Number: 5,683,904
[45] Date of Patent: *Nov. 4, 1997

[54] UBIQUITIN-SPECIFIC PROTEASES

[75] Inventors: Rohan T. Baker, Garran, Australia; John W. Tobias, Cambridge; Alexander Varshavsky, Boston, both of Mass.

[73] Assignee: Massachusetts Institute of Technology, Cambridge, Mass.

[*] Notice: The term of this patent shall not extend beyond the expiration date of Pat. No. 5,212,058.

[21] Appl. No.: 487,203

[22] Filed: Jun. 7, 1995

Related U.S. Application Data

[60] Continuation of Ser. No. 5,002, Jan. 15, 1993, Pat. No. 5,494,818, which is a division of Ser. No. 789,915, Nov. 8, 1991, Pat. No. 5,212,058, which is a continuation-in-part of Ser. No. 573,958, Aug. 28, 1990, abandoned, which is a continuation-in-part of Ser. No. 521,089, May 9, 1990, abandoned.

[51] Int. Cl.$^6$ .............................. C12N 1/20; C12N 9/50; C12N 9/48; C12N 1/00
[52] U.S. Cl. ...................... 435/252.3; 435/212; 435/219; 435/252.33; 435/243; 435/320.1; 435/6; 536/23.2; 536/23.4
[58] Field of Search ...................... 435/219, 243, 435/252.3, 252.8, 6, 252.33; 536/23.2, 23.4

[56] References Cited

U.S. PATENT DOCUMENTS

| | | | |
|---|---|---|---|
| 5,108,919 | 4/1992 | Liu et al. | |
| 5,132,213 | 7/1992 | Bachmair et al. | 435/69.7 |
| 5,156,968 | 10/1992 | Liu | 435/224 |
| 5,212,058 | 5/1993 | Baker et al. | 435/252.33 |

FOREIGN PATENT DOCUMENTS

| | | |
|---|---|---|
| WO 88/02406 | 4/1988 | WIPO. |
| WO 89/12678 | 6/1989 | WIPO. |
| WO 91/17245 | 11/1991 | WIPO. |

OTHER PUBLICATIONS

Baker et al., "Ubiquitin–Specific Processing Proteases of the Yeast *Saccharomyces cerevisiae*", CH200, Abstracts, 20th Annual Meetings *Journal of Cellular Biochemistry*, Keystone Symposia on Molecular & Cellular Biology, supplement 15G, 1991, Apr. 6–Apr. 25, 1991, Wiley–Liss.
Tobias et al., *J. Biol. Chem.* 266: 12021 (1991).
Agell et al, *Biochem. J.* 272: 615 (1991).
Baker et al., *J. Biol. Chem.* 267: 2364 (1992).
Sullivan et al., *Plant Physiol.* 94: 710 (1990).
Hershko et al., "Role of the α–amino group of protein in ubiquitin–mediated protein breakdown", *Pro. Natl. Acad. Sci. USA* 81: 7021 (1985).
Tsunasawa et al., "Amino–terminal Processing of Mutant Forms of Yeast ISO–1–cytochrome c", *J. Biol. Chem* 260: 5382 (1985).
Boissel et al., "Amino–terminal processing of proteins: Hemoglobin South Florida, a variant with retention of initiator methionine and $N^\alpha$–acetylation", *Proc. Natl. Acad. Sci. USA* 82: 8448 (1985).
Thornton et al., "Amino and Carboxy–terminal regions in globular proteins", *J. Mol. Biol.* 167: 443 (1983).
Feber et al., "Transfer RNA is Required for Conjugation of Ubiquitin to Selective Substrates of the Ubiquitin–and ATP–dependent Proteolytic System", *J. Biol. Bhem.* 261: 3128 (1986).
Bachmair et al., "In Vivo Half–Life of a Protein is a Function of its Amino–Terminal Residue", *Science* 234: 179 (1986).
Feber et al., "Role of arginine–tRNA in protein degradation by the ubiquitin pathway", *Nature* 326: 808 (1988).
Reiss et al., "Specificity of Binding of $NH_2$–terminal Residue of Proteins to Ubiquitin–Protein Ligase", *J. Biol. Chem.* 263: 2693 (1988).
Townsend et al., "Defective Presentation to Class I–Restricted Cytotoxic T Lymphocytes in Vaccinia–Infected Cells is Overcome by Enhanced Degradation of Antigen", *J. Exp. Med.* 168: 1211 (1988).
Bachmair, A. and Varshavsky, A., "The Degradation Signal in a Short–Lived Protein", *Cell* 56: 1019 (1989).
Chau et al., "A Multiubiquitin Chain is confined to Specific Lysine in a Targeted Short–Lived Protein", *Science* 243: 1576 (1989).
Gonda et al., "Universality and Structure of the N–End Rule", *J. Biol. Chem.* 264: 16700 (1989).
Miller et al., "Cloning and Expression of a Yeast Ubiquitin–Protein Cleaving Activity in *Escherichia Coli*", *Biotechnology* 1: 698 (1989).
International Search Report, PCT/US89/01468.
Sassenfeld, H.M., "Engineering Proteins for Purification", *Trends in Biotechnology* 8: 88 (1990).
Tobias and Varshavsky, "Cloning and Functional Analysis of the Ubiquitin–specific Protease Gene UBP1 of *Saccaromyces cerevisiae*", *J. Biol. Chem* 266: 12021 (1991).
Ohmen et al., "Divergent Overlapping Transcripts of the PET122 Locus in *Saccharomyces cerevisiae*", *Mol. Cell. Biol.* 10: 3027 (1990).
Ohmen et al., "Molecular Cloning and Nucleotide Sequence of the Nuclear PET122 Gene Required for Expression of the Mitochondrial COX3 Gene in *S. cerevisiae*", *Nucleic Acids Research* 16: 10783 (1988).

*Primary Examiner*—Robert A. Wax
*Assistant Examiner*—Nashaat T. Nashed
*Attorney, Agent, or Firm*—Kevin M. Farrell

[57] ABSTRACT

The disclosure relates to a generic class of ubiquitin-specific proteases which specifically cleave at the C-terminus of the ubiquitin moiety in a ubiquitin fusion protein irrespective of the size of the ubiquitin fusion protein. More specifically, the disclosure relates to ubiquitin-specific proteases of this class which have been isolated from a cell. The disclosure also relates to isolated DNA sequences encoding the proteases of this class.

10 Claims, 4 Drawing Sheets

UBIQUITIN-SPECIFIC PROTEASES

This application is a continuation of application Ser. No. 08/005,002, filed on Jan. 15, 1993 (now U.S. Pat. No. 5,494,818) which is a divisional of application Ser. No. 07/789,915, filed on Nov. 8, 1991 (now U.S. Pat. No. 5,212,058), which is a continuation-in-part of application Ser. No. 07/573,958, filed Aug. 28, 1990 (now abandoned), which is a continuation-in-part of application Ser. No. 07/521,089, filed May 9, 1990 (now abandoned).

GOVERNMENT FUNDING

This invention was partially supported by the U.S. Government and the government has certain rights to the invention.

BACKGROUND OF THE INVENTION

Ubiquitin (Ub), a highly conserved 76-residue protein, is present in eukaryotic cells either free or covalently joined to a great variety of proteins. The post-translational coupling of ubiquitin to other proteins is catalyzed by a family of Ub-conjugating (E2) enzymes and involves formation of an isopeptide bond between the C-terminal Gly residue of ubiquitin and the ε-amino group of a Lys residue in an acceptor protein. One function of ubiquitin is to mark proteins destined for selective degradation. Ubiquitin was also shown to have a chaperone function, in that its transient (cotranslational) covalent association with specific ribosomal proteins promotes the assembly of ribosomal subunits.

Unlike branched Ub-protein conjugates, which are formed posttranslationally, linear Ub-protein adducts are formed as the translational products of natural or engineered gene fusions. Thus, in the yeast *Saccharomyces cerevisiae* for example, ubiquitin is generated exclusively by proteolytic processing of precursors in which ubiquitin is joined either to itself, as in the linear polyubiquitin protein Ubi4, or to unrelated amino acid sequences, as in the hybrid proteins Ubi1–Ubi3. In growing yeast cells, ubiquitin is generated largely from the Ubi1–Ubi3 precursors whose "tails" are specific ribosomal proteins. The polyubiquitin (UB14) gene is dispensable in growing cells but becomes essential (as the main supplier of ubiquitin) during stress. The lack of genes encoding mature ubiquitin, and the fusion structure of ubiquitin precursors in yeast are characteristic of other eukaryotes as well.

Ub-specific, ATP-independent proteases capable of cleaving ubiquitin from its linear or branched conjugates have been detected in all eukaryotes examined but not in bacteria such as *Escherichia coli*, which lack ubiquitin and Ub-specific enzymes. Miller et al. (*Biotechnology* 1: 698–704 (1989)) have cloned a *S. cerevisiae* gene, named YUH1, encoding a Ub-specific protease that cleaves ubiquitin from its relatively short C-terminal extensions but is virtually inactive with larger fusions such as Ub-β-galactosidase (Ub-βgal). Wilkinson et al. (*Science* 246:670–673 (1989)) have also cloned a eDNA encoding a mammalian homolog of the yeast Yuh1 protease. Tobias and Varshavsky (*J. Biol. Chem.* 266:12021–12028 (1991)) reported the cloning and functional analysis of another yeast gene, named UBP1, which encodes a Ub-specific processing protease whose amino acid sequence is dissimilar to those of the Yuh1 protease and other known proteins. Unlike YUH1 and its known homologues in other species, Ubp1 deubiquitinates ubiquitin fusion proteins irrespective of their size or the presence of an N-terminal ubiquitin extension.

SUMMARY OF THE INVENTION

The subject invention relates to a generic class of ubiquitin-specific proteases which specifically cleave at the C-terminus of the ubiquitin moiety in a ubiquitin fusion protein irrespective of the size of the ubiquitin fusion protein. More specifically, the invention relates to ubiquitin-specific proteases of this class which have been isolated from a cell. The invention also relates to isolated DNA sequences encoding the proteases of this class.

One useful property of ubiquitin-specific proteases is that they cleave ubiquitin from its C-terminal extensions irrespective of the identity of the extension's residue abutting the cleavage site. This property of the Ubp proteases make possible the in vivo or in vitro generation of proteins or peptides bearing predetermined N-terminal residues, a method with applications in both basic research and biotechnology.

DETAILED DESCRIPTION OF THE INVENTION

Figure 1:
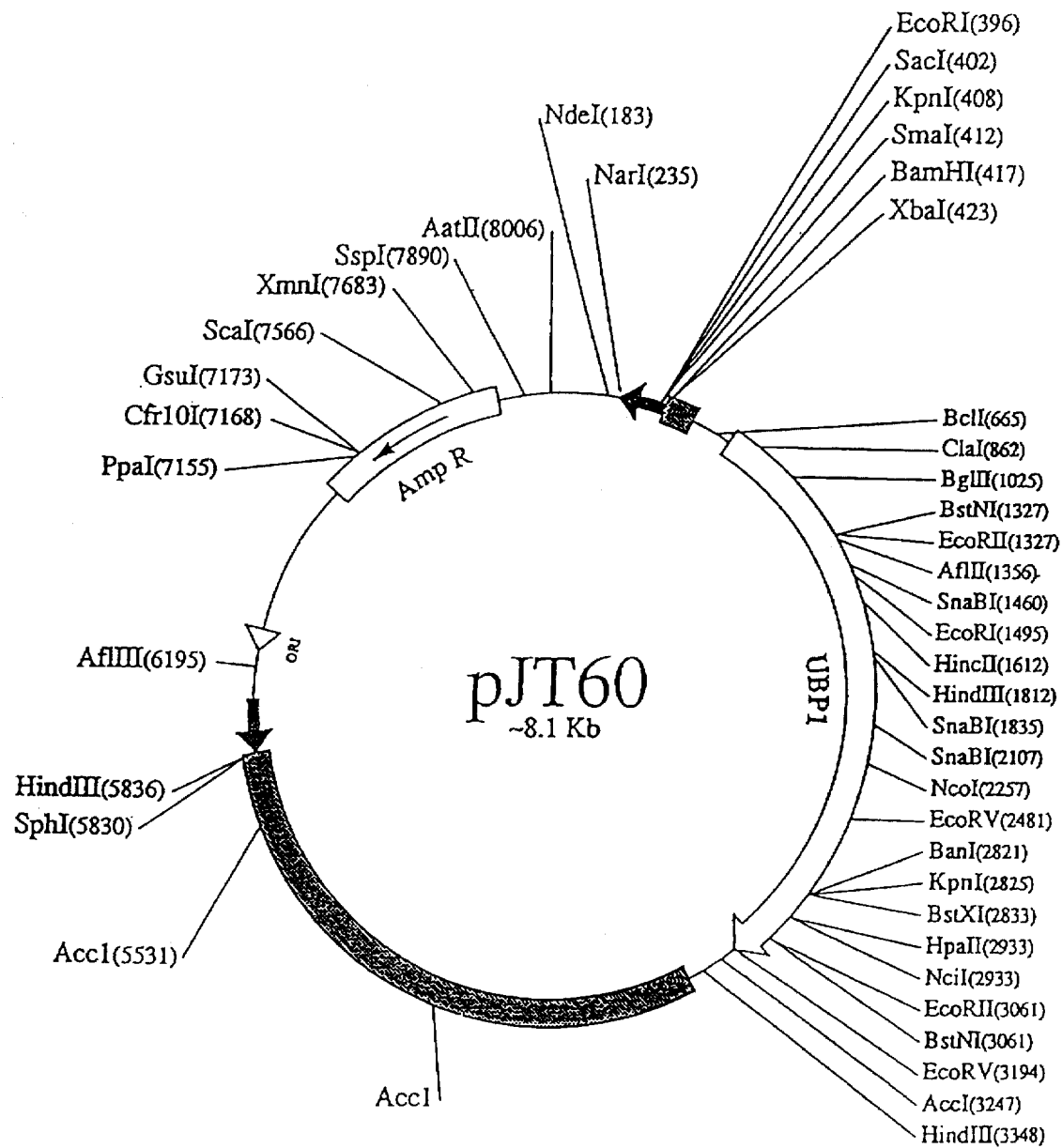
FIG. 1 is a diagram representing the plasmid pJT60.

A ubiquitin fusion protein, as used herein, is defined as a fusion protein comprising ubiquitin or its functional homolog having its C-terminal amino acid residue fused to the N-terminal amino acid residue of a non-ubiquitin protein or peptide. As discussed in the Examples which follow, the ubiquitin fusion protein can be a naturally occurring fusion protein, or a fusion protein produced by recombinant DNA technology. The specific cleavage takes place either in vivo or in vitro, between the C-terminal residue of ubiquitin and the N-terminal residue of the protein or peptide.

In contrast to the class of ubiquitin-specific proteases disclosed herein, the previously isolated YUH1 enzyme cleaves ubiquitin off a ubiquitin fusion protein only if the non-ubiquitin portion of the fusion is relatively short (shorter than about 60 residues). Since, for instance, many of the pharmaceutically important proteins are much longer than 60 residues, the YUH1 protease cannot be used to deubiquitinate fusions of these proteins with ubiquitin. The proteases of the class disclosed herein, however, can be used for this purpose, thereby allowing the generation of desired residues at the N-termini of either large or small proteins, polypeptides or peptides (the terms protein, polypeptide and peptide are often used interchangeably in the art).

Disclosed in the Examples which follow are DNA sequences which encode three of the proteases which are members of the class of ubiquitin-specific proteases to which this invention pertains. These proteases have been designated UBP1, UBP2 and UBP3. The DNA sequences which encode these proteases, and their deduced amino acid sequences, are set forth in Sequence I.D. Numbers 3–4, Sequence I.D. Numbers 5–6 and Sequence I.D. Numbers 7–8, respectively. The DNA sequences which encode the proteases disclosed herein can be isolated by the methods described below, or by using the polymerase chain reaction amplification method. Primer sequences to be used in such an amplification method can be determined by reference to the DNA Sequence Listing below.

The proteases UBP1 and UBP2 demonstrate activity both in vivo and in vitro, whereas the UBP3 protease demonstrates activity only in vivo. Each of these proteases has been shown to specifically cleave a ubiquitin fusion protein having a molecular weight of about 120 kilodaltons (ubiquitin-methionine-β-galactosidase). By contrast, the YUH1 ubiquitin-specific protease is virtually inactive with this ubiquitin fusion either in vitro or in vivo. The DNA sequence encoding this 120 kilodalton fusion protein is represented in Sequence I.D. Number 1. The amino acid sequence is represented in Sequence I.D. Numbers 1-2.

The scope of the invention encompasses an isolated DNA sequence encoding a ubiquitin-specific protease, or a biologically active portion thereof, which is characterized by the ability to hybridize specifically with the DNA sequence represented in Sequence I.D. Number 3, Sequence I.D. Number 5 or Sequence I.D. Number 7, under stringent hybridization conditions. DNA sequences which hybridize to the listed sequences under stringent hybridization conditions are either perfectly complementary, or highly homologous to the listed sequence. Homologous, as used herein, refers to DNA sequences which differ from the listed sequence, but the difference has no substantial effect on the biological activity (i.e., cleavage properties) of the encoded protease. One of the possible sets of stringent hybridization conditions is 50% formamide, 5×SSPE (1×SSPE is 0.15 mNaCl, 1 mM Na-EDTA, 10 mM Na-phosphate, pH 7.0), 5×Denhardt's solution (0.1% polyvinylpyrrolidone, 0.1% Ficoll) at 45° C.

The isolated DNA sequences which fall within the scope of this invention can be used to express the encoded protease in large quantities in either prokaryotic or eukaryotic host cells. For this purpose, the DNA is inserted into a prokaryotic or eukaryotic expression vector, with the appropriate regulatory signals, and used to transform cells. A variety of appropriate vectors and regulatory signals have been previously developed for this purpose and are well known to those skilled in the art.

As discussed in the Examples below, the proteases of this invention have been overexpressed in E. coli to the extent that they represent a substantial proportion of the total cellular protein. The purification of a protein which is expressed at such substantial levels, and for which a simple assay system is established, is a straightforward matter to one skilled in the art.

Isolated UBP1 or UBP2, or a cellular extract containing UBP1 or UBP2 produced from a recombinant DNA expression vector can be used to cleave ubiquitin off ubiquitin fusions in vitro. A cellular extract can be prepared from a culture of host cells expressing a recombinant DNA expression vector by simply concentrating and lysing the cell culture. The lysis can be followed, optionally, by various degrees of purification as described above. The range of conditions appropriate for in vitro cleavage can be determined empirically by one skilled in the art, using no more than routine experimentation, from the information provided in the Examples which follow.

In addition, the UBP1, UBP2 and UBP3 proteases can be used to deubiquitinate fusion proteins in vivo. For example, prokaryotic cells harboring an expression vector encoding the protease can be transformed with an expression vector encoding a ubiquitin fusion protein. Such cells will produce a deubiquitinated product having a predetermined N-terminal amino acid residue. There are many well known advantages to producing recombinant proteins in prokaryotic organisms such as E. coli.

In some fusions of ubiquitin to a non-ubiquitin protein or peptide, the presence of the ubiquitin moiety may inhibit or modify the functional activity of the non-ubiquitin protein or peptide. In this case, ubiquitin can be used as a temporary inhibitor (or modifier) of the functional activity of the non-ubiquitin protein or peptide, with the ability to restore the original functional activity at any desired time, either in vitro or in vivo, by contacting the corresponding ubiquitin fusion with the ubiquitin-specific protease to remove the ubiquitin moiety.

The invention is further illustrated by the following Examples.

EXAMPLES

Example I: Cloning and Analysis of UBP1

Preparation of Yeast Genomic DNA Library and Lysate for Screening

Escherichia coli (strain HB101) transformed with a Saccharomyces cerevisiae genomic library was used for a sib selection strategy. The library, RB237, was produced by partially digesting yeast genomic DNA with Sau3IIA and ligating the fragments into the BamH1 site in the Tet® ene of the yeast/E. coil shuttle vector YCp50. Upon initial analysis, the library contained inserts with an average size of ~19 Kb.

E. coli, transformed with the above library, were plated on agar containing Luria Broth (LB) and ampicillin (amp) (100 µg/ml) at a density of about 40 viable cells per plate. The plates were incubated at 36° C. for 16 hours. The colonies were then replicated onto LB/amp plates. The original plates were stored at 4° C., and their replicas were grown for 24 hours at 36° C. Each replicate was eluted with 1 ml of LB/amp (50 µg/ml) by repeated washing over the surface of the plate until all of the colonies were loosened into the liquid. The entire eluate was then added to 4 ml of LB/amp, and incubated on a roller drum at 36° C. overnight.

The E. coli cells in these overnight (stationary-phase) cultures were then lysed. 1.7 ml of each culture was placed in a microcentrifuge tube on ice, and then centrifuged at 12,000× g for 1 min at 4° C. The cell pellet was resuspended, by vortexing at high speed, in 50 µl of 25% sucrose (w/v), 250 mM Tris-HCl (pH 8.0). 10 µl of freshly made lysozyme solution (10 mg/ml chicken egg-white lysozyme (Sigma) in 0.25 M Tris-HCl (pH 8.0)) was then added, and mixed by light vortexing. The suspension was incubated on ice for 5 minutes, 150 µl of 75. mM EDTA, 0.33 M Tris-HCl (pH 8.0) was then added, mixed by light vortexing, and the tube was incubated on ice for 5 minutes with occasional stirring. 1 µl of 10%. Triton X-100 (Pierce) was then added to each tube, and mixed by pipetting. The cell lysate was centrifuged at 12,000× g for 15 minutes at 4° C. The supernatant was retained on ice, and the pellet was discarded.

Preparation of Labeled Substrate

Cell lysates were assayed for the Ub-specific protease activity using a $^{35}$S-labeled substrate. $^{35}$S-labeled ubiquitin-methionine-dihydrofolate reductase (Ub-Met-DHFR) was prepared as follows: Luria Broth (50 ml) supplemented with 50 µg/ml ampicillin was inoculated with 1 ml of a saturated overnight culture of E. coli strain JM101 containing a plasmid expressing the Ub-Met-DHFR fusion protein from an IPTG-inducible, highly active derivative of the lac promoter. The cells were grown with shaking at 37° C. until they reached an $A_{600}$ of ~0.9. The culture was chilled on ice for 15 minutes, then centrifuged at 3000× g for 5 minutes and washed 2 times with M9 salts at 0° C. The cells were resuspended after the final wash in 25 ml of M9 salts supplemented with 0.2% glucose, 1.8 µg/ml thiamine, 40 µg/ml ampicillin, 1 mM IPTG, 0.0625% (w/v) methionine assay medium (Difco). The suspension was then shaken for 1 hour at 37° C. and the cells were labeled by the addition of 1 mCi of $^{35}$S-Translabel (ICN), followed by a 5-min incubation, with shaking. Unlabeled L-methionine was then added to a final concentration of 0.0032 % (w/v), and the cells were shaken for an additional 10 min. The cells were then harvested (3000× g for 5 minutes) and washed once in cold M9 salts. After the M9 wash, the cell pellet was resuspended in 0.5 ml 25% Sucrose, 50 mM Tris-HCl (pH 8.0), and incubated on ice for 5 minutes. During this time, chicken egg-white lysozyme (Sigma) was dissolved freshly in 250 mM Tris-HCl (pH 8.0) to a concentration of 10 mg/ml. 10 µl of the lysozyme solution was added to the cell suspension, mixed, and incubated for 5 minutes at 0° C. 5 µl of 0.5 M EDTA (pH 8.0) was then added, and the suspension left at 0° C. for 5 minutes, with intermittent mixing. The cell suspension was then added to a centrifuge tube containing 0.975 ml of 65 mM EDTA (pH 8.0), 50 mM-Tris-HCl (pH 8.0) and protease inhibitors antipain, chymostatin, leupeptin, aprotinin and pepstatin, each at 25 µg/ml. 10 µl 10% Triton X-100 (Pierce) was then added, and dispersed by pipetting. The lysate was centrifuged at 39,000× g for 30 minutes. The supernatant was retained, quickly frozen in liquid nitrogen, and stored at −85° C.

To affinity-purify the $^{35}$S-labeled Ub-Met-DHFR, a methotrexate (MTX)-agarose affinity matrix was prepared according to the method of Kaufman (*Meth. Enzymol.* 34:272–281 (1974)). A 0.5 ml bed volume column was filled with the MTX-agarose, and washed with 10 ml of MTX column buffer (20 mM Hepes (pH 7.5), 1 mM EDTA 200 mM NaCl, 0.2 mM dithiothreitol). The $^{35}$S-labeled supernatant of the preceding step was thawed and applied to the MTX-agarose column. The column was washed with 50 ml of MTX column buffer, 50 ml of MTX column buffer containing 2M urea, and again with 50 ml of MTX column buffer. The labeled Ub-Met-DHFR was eluted from the column with folic acid elution buffer (0.2M potassium borate (pH 9.0), 1 M KCl, 1 mM DTT, 1 mM EDTA, 10 mM folic acid). The elution buffer was applied to the column in 1 ml aliquots, and 1 ml fractions were collected. The fractions were assayed for $^{35}$S radioactivity and those fractions that contained the major radioactive peak were pooled. The pooled fractions were dialyzed for ~20 hours against two changes of a storage buffer containing 40 mM Tris-HCl (pH 7.5), 1 mM MgCl$_2$, 0.1 mM EDTA, 50% glycerol. The purified $^{35}$S-labeled Ub-Met-DHFR was assayed by SDS-PAGE, followed by fluorography and found to be greater than 95% pure.

Deubiquitination Assay

The cell lysates were assayed for the Ub-specific protease activity, by combining 9 µl of the cell lysate supernatant with 1 µl of the affinity purified $^{35}$S-labeled Ub-Met-DHFR fusion in a 0:5 ml microcentrifuge tube, and incubated at 36° C. for 3 hr. 5 µl of a 3-fold concentrated electrophoretic sample buffer (30% glycerol, 3 % SDS (w/v), 15 mM EDTA, 0.2M 2-mercaptoethanol, 0.3 µg/ml bromophenol blue, 375 mM Tris-HCl (pH 6.8) was then added, and each tube was placed in a boiling water bath for 3 min. The samples were loaded onto a 12% polyacrylamide-SDS gel, and electrophoresed at 50 V until the bromophenol dye reached the bottom of the gel. Positions of the radioactively labeled proteins in the gel were visualized by fluorography. The gel was washed in 10% acetic acid, 25% methanol for 15 minutes, rinsed in H$_2$O for 15 minutes and incubated with Autofluor (National Diagnostics) for 1 hour. The gel was then dried at 80° C. under vacuum, placed in a light-proof cassette against Kodak XAR-5 film and stored at −85° C. overnight.

The above deubiquitination assay was repeated with lysates from different pools of *E. coli* transformants until the gel analysis revealed a lysate that displayed protcolytic activity acting at the ubiquitin-DHFR junction. This assay indicated that at least one of the ~40 *E. coli* colonies on the original LB/amp plate (from which the pooled lysate had been derived) contained a YCp50-based plasmid having a yeast DNA insert conferring Ub-specific proteolytic activity.

The next step of this sib selection approach to cloning the UBP1 gene was to carry out a similar Ub-Met-DHFR cleavage assay to determine which of the ~40 colonies in a "positive" pool contained the desired plasmid. To do so, a sample of each individual colony on the plate of interest was inoculated into LB/amp and grown overnight. The Ub-Met-DHFR cleavage assay was then repeated exactly as above, but this time each lysate sample was representative of a single clonal *E. coli* transformat rather than a mixture of ~40 such transformants. This analysis revealed a single colony that contained a plasmid which conferred the ability to specifically cleave at the Ub-DHFR junction.

Cloning and DNA Sequence Analysis of UBP1

Analysis of the initially isolated plasmid (pJT55) revealed a ~15 kb insert of yeast genomic DNA in the YCp50 vector. SphI digestion of this plasmid yielded a ~14 kb fragment, which, upon subcloning into the vector pUC19, conferred the same protcolytic activity. This plasmid was called pJT57. The ~14 kb fragment was subcloned further by cutting with SphI and XhoI, isolating the ~5.5 kb of the insert DNA and subcloning it into the pUC19 vector pre-cut with SphI and SalI. This resulted in ~8.1 kb plasmid pJT60 containing the ~5.5 kb yeast DNA insert that conferred the same Ub-specific protcolytic activity as the original plasmid.

A map showing restriction endonuclease recognition sites in plasmid pTT60 is shown in FIG. 1. In the map, base pair positions are indicated by a number in parentheses following a restriction site. The yeast DNA insert in pJT60 contained a KpnI site near its center that divided the insert into two smaller fragments A and B (bases 423 and 5830). In this fragment, the open arrow indicates the Open reading frame (ORF) representing UBP1. The entire ORF, and the thin lines bracketing it, represent the extent of the sequenced DNA shown in Sequence I.D. Number 3. Both fragments were subcloned into pUC19, yielding pJT60A and pJT60B. Fragment A was isolated from pJT57 after cutting with KpnI and SphI. This fragment was subcloned into pUC19 that had been cut with the same restriction endonucleases. Fragment B was isolated from pJT57 that had been cut by KpnI and XhoI; it was subcloned into pUC19 that had been cut by KpnI and SalI. Neither pJT60A nor pJT60B was able to confer Ub-specific proteolytic activity. This result suggested that the gene of interest straddled the KpnI site of the ~5.5 kb insert of pJT60.

To sequence the cloned gene, the inserts of pJT60A and pJT60B were subcloned into the M13mp19 phage vector. Nucleotide sequence was determined (using the chain termination method) in both directions from the internal KpnI site in pJT60. The KpnI site was found to be ensconced within an open reading frame extending from this site in both directions. Unidirectional deletions were then made in the sequencing templates by the methods of Dale et al., (*Plasmid* 13:31–40 (1989)) and the entire open reading frame (ORF) was determined. The 5' end of the ORF was in fragment B and the termination codon was in fragment A. The ORF was 2427 nucleotides long, and encoded an 809-residue protein, with a molecular mass of 93 kD. The sequenced ORF was then isolated on a 2.8 kb fragment by cutting pJT60 with AccI, filling in the 5' overhangs with Klenow PolI, and ligating SalI linkers to the blunt ends. This construct was digested with SalI and BamHI, the 2.8 kb fragment was electrophoretically purified and ligated into pUC19 that had been digested with BamHI and SalI. The resulting plasmid was called pJT70. This plasmid, when transformed into E. coli, was able to confer the Ub-specific proteolytic activity to the same extent as either the original ~15 kb insert in YCp50 or the ~5.5 kb insert of the pJT60 plasmid that includes the ~2.8 kb fragment of pJT70. The plasmid pJT60 has been deposited with the American Type Culture Collection (Rockville, Md.), and has been assigned ATCC designation 68211. The 2.8 kb fragment contained no other ORFs of significant size, indicating that the sequenced ORF shown in Sequence I.D. Number 3 encoded the Ub-specific protease. This new gene has been named UBP1, for Ubiquitin-specific protease.

Substrate Specificity of UBP1

The in vitro substrate specificity of the UBP1 encoded product was examined by testing for cleavage using a variety of substrates. These experiments demonstrated the ability of Ubp1 to deubiquitinate [$^{35}$S]Ub-Met-DHFR and [$^{35}$S]ubiquitin-methionine-β-galactosidase (Ub-Met-βgal). The construction of the [$^{35}$S]Ub-Met-βgal fusion protein has been described previously (Bachmair et al., Science 234:179–186 (1986)). The labeled substrates were employed in a deubiquitination assay as described above. Both fusion proteins were specifically deubiquitinated. Fluorograms of electrophoretic patterns from these deubiquitination experiments revealed deubiquitination reaction products of the expected molecular mass.

The Ubp1 protease was alto shown to deubiquitinate natural ubiquitin fusions to yeast ribosomal proteins (Ubi2 and Ubi3) in vitro. An expression construct encoding Ubi2, a natural ubiquitin-ribosomal protein fusion of S. cerevisiae, was used to transform E. coli. A cellular extract from a culture of the transformed cells was treated with an E. coli extract from cells expressing Ubp1, followed by electrophoresis in a polyacrylamide-SDS-gel, blotting onto polyvinylidene difluoride membrane, and detection using a rabbit anti-ubiquitin antibody, with subsequent application of a secondary goat anti-rabbit antibody linked to alkaline phosphatase, and colorgenic substrates of alkaline phosphatase. These experiments demonstrated that an extract from E. coli expressing the Ubp1 gene product effectively deubiquitinated the natural ubiquitin fusion proteins Ubi2 and Ubi3.

To determine whether a sandwich-type ubiquitin fusion protein in which the ubiquitin moiety had an N-terminal extension was a substrate for Ubp1, a plasmid was constructed that encoded a triple fusion protein consisting of an N-terminal dihydrofolate reductase (DHFR) moiety, a flexible linker region of three glycine residues and a serine, followed by ubiquitin and Met-βgal moieties. The mouse DHFR gene was isolated on a BamHI/HindIII fragment from a plasmid encoding Ub-Met-DHFR (Bachmair and Varshavsky, Cell 56:1019–1032 (1989)). This fragment was treated with Klenow PolI to fill in the ends, and KpnI linkers were ligated. The fragment was then cut with KpnI to yield a 678 bp fragment which was cloned into the KpnI site in a modified Ub-Met-βgal expression vector in which the second codon of the ubiquitin moiety was altered to encode a KpnI site (Gonda et al., J. Biol. Chem. 264:16700–16712 (1989)). This procedure yielded a plasmid that encoded DHFR, ubiquitin (without the initial Met codon) and Met-βgal, with the open reading frames for each moiety not yet aligned into a single open reading frame. To effect the alignment of the open reading frames and to position the initiator codon of DHFR correctly with respect to the GAL promoter in the vector, site-directed mutagenesis was performed at two locations in the plasmid.

The plasmid was cut with BamHI and HindIII, and the ~2.76 kb fragment encoding DHFR, ubiquitin and the first few residues of Met-βgal was cloned into M13mp19 that had been cut with the same enzymes. Oligonucleotide-mediated, site-directed mutagenesis was performed using the single-stranded M13 derivative and standard protocols. The first oligodeoxynucleotide was designed to produce a 20 bp deletion that would bring the initiator codon of DHFR to a proper position relative to the GAL5 promoter of the vector. The second oligodeoxynucleotide was designed to bring together the reading frames of DHFR and ubiquitin, and to introduce the 4-residue spacer (-Gly-Gly-Gly-Ser-) SEQ ID NO:9 between the DHFR and ubiquitin moieties. After mutagenesis, DNA clones were tested for incorporation of both changes by direct nucleotide sequencing using the chain termination method.

Figure 2:
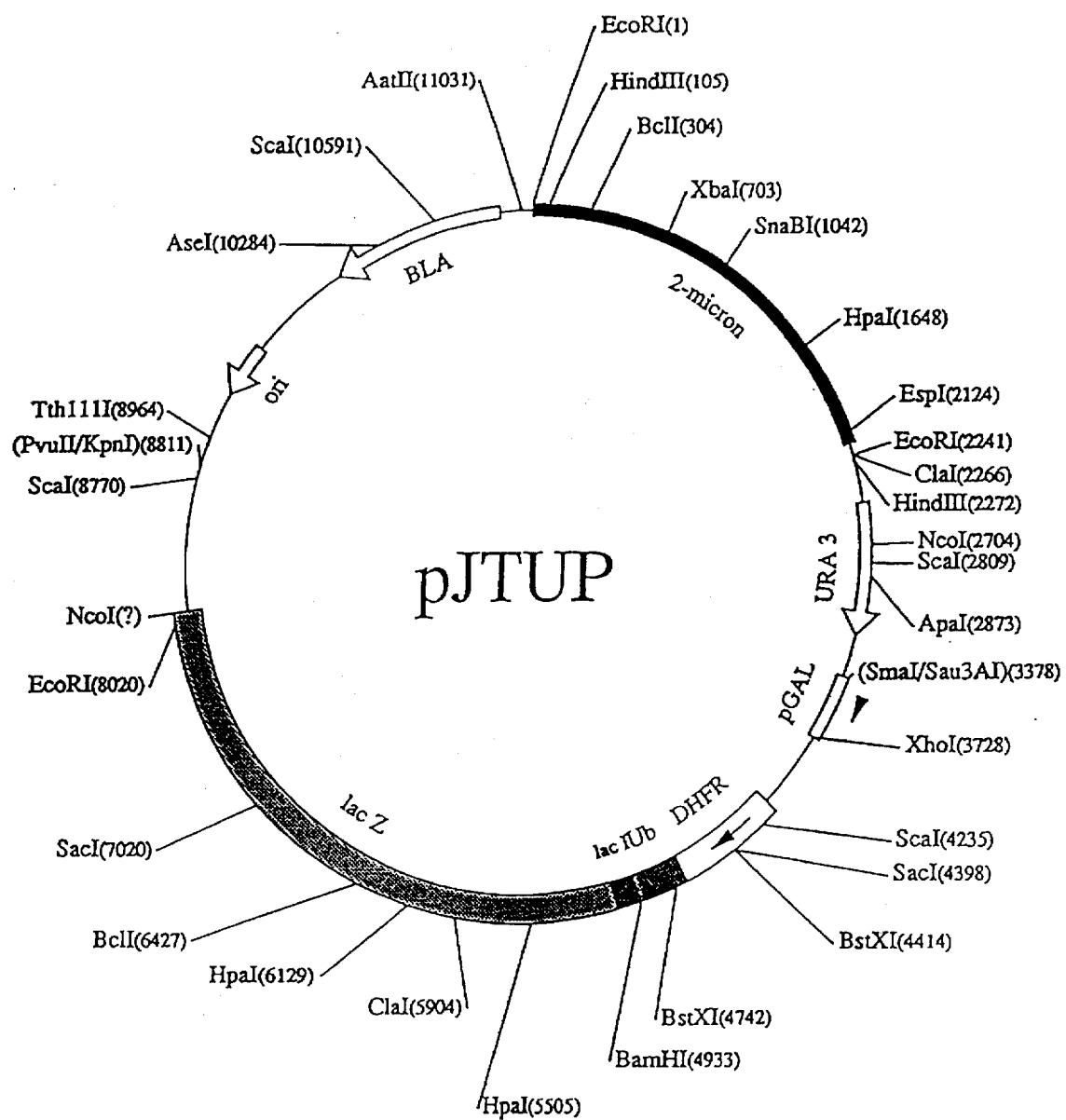
FIG. 2 is a diagram representing the plasmid pJTUP.

Double stranded, replicative form (RF) of the desired M13 clone was isolated and digested with BamHI and XhoI. The resulting ~1.2 kb fragment was cloned into the ~9.87 kb fragment of a Ub-Met-βgal expression vector digested with the same enzymes, replacing the Ub-Met-coding fragment with the DHFR-Ub-Met-coding fragment produced by the site-directed mutagenesis. This last step yielded an expression vector that encoded the triple fusion DHFR-Ub-Met-βgal. The vector was named pTJUP (FIG. 2).

pJTUP was used to test whether a ubiquitin fusion in which the ubiquitin moiety is located between two non-ubiquitin moieties would be a substrate for cleavage by Ubp1. In E. coli metabolically labelled with [$^{35}$S] methionine, the fate of expressed DHFR-Ub-Met-βgal was determined in the presence or absence of Ubp1 using immunoprecipitation with a monoclonal antibody to β-galactosidase, followed by polyacrylamide-SDS gel electrophoresis and fluorography. These experiments demonstrated that UBP1 efficiently cleaves the triple fusion protein.

The ability to cleave such a sandwich construct is particularly useful in situations wherein the first non-ubiquitin moiety confers some desirable property on the sandwich ubiquitin fusion. For example, the first non-ubiquitin moiety may facilitate affinity purification of the ubiquitin fusion protein. In such a case, the fusion protein can be expressed in a cell (e.g., E. coli) that lacks ubiquitin-specific proteases, and a cellular lysate can be passed over an affinity column specific for the first non-ubiquitin moiety. One example of a protein which is useful for affinity purification is streptavidin. Following affinity purification of the fusion protein, the latter is contacted with the ubiquitin-specific protease. The second non-ubiquitin moiety is thereby liberated from the sandwich ubiquitin fusion construct.

Example 2: Cloning and Analysis of UBP2 and UBP3

Cloning Strategy

The strategy employed to clone the genes encoding Ub-specific proteases of S. cerevisiae other than Ubp1 and Yuh 1 took advantage of the fact that bacteria such as E. coli lack ubiquitin and Ub-specific enzymes, and was also based on the recent demonstration that the N-end rule, a relation between the in vivo half-life of a protein and the identity of its N-terminal residue, operates not only in eukaryotes but in E. coli as well. In eukaryotes, ubiquitin fusions to test proteins such as β-galactosidase are deubiquitinated by Ub-specific processing proteases irrespective of the identity of a residue at the Ub-βgal junction, making it possible to expose in vivo different residues at the N-termini of otherwise identical test proteins. This technique, required for detection and analysis of the N-end rule in eukaryotes, has been made applicable in bacteria through the isolation of the yeast UBP1 gene (see Example 1), inasmuch as E. coli transformed with UBP1 acquires the ability to deubiquitinate ubiquitin fusions. The finding that an X-βgal test protein such as Arg-βgal is short-lived in E. coli, whereas Ub-Arg-βgal is long-lived, made possible a new E. coli-based in vivo screen for Ub-specific proteases. E. coli expressing the (long-lived) Ub-Arg-βgal fusion protein form blue colonies on plates containing X-Gat, a chromogenie substrate of βgal. However, if a deubiquitinating activity is present in the cells as well, Ub-Arg-βgal is converted into a short-lived Arg-βgal, whose low steady-state level results in white E. coli colonies on X-Gal plates.

To be clonable by this strategy using a conventional yeast genomic DNA library, a yeast gene must have a promoter that functions in E. coli (a minority of yeast promoters can do so), must lack introns in its coding region (most yeast genes lack introns), and must encode a Ub-specific processing protease that functions as a monomer or a homooligomer. One advantage of this in vivo screen over the previously used in vitro screen that yielded UBP1 is that the former requires a relevant protease to be active in vivo but not necessarily in vitro (in E. coli extracts).

Plasmids Expressing Ubiquitin-Containing Test Proteins

The plasmid pACUb-R-βgal, expressing Ub-Arg-βgal, was constructed by subcloning the ~5 kb ScaI fragment of pUB23-R (Bachmalt et al., Science 234:179–186 (1986)) that contains the Ub-Arg-βgal coding region downstream from the GAL10 promoter, into HincII-digested pACYC 184, whose P 15A origin of replication makes this plasmid compatible with pMB1(ColE1)-based E. coli vectors such as pUC19 and pBR322. pACUb-R-βgal expressed Ub-Arg-βgal in E. coli from the galactose-inducible yeast GAL10 promoter, which functions as a weak constitutive promoter in E. coil. The plasmid pACUb-M-βgal, expressing Ub-Met-βal, was constructed identically to pACUb-R-βgal except that pUB23-M was used instead of pUB23-R. Plasmids pKKUBI2, pKKUBI3 and pUB17 expressed in E. coli the natural yeast ubiquitin fusions (ubiquitin precursors) Ubi2, Ubi3 and Ubi4 (polyubiquitin), respectively (Ozkaynak et al., EMBO J. 6:1429–1439 (1987)), using an isopropylthiogalactoside (IPTG)-inducible promoter in the vector pKK223-3 (Ausubel et al., Current Protocols in Molecular Biology, J. Wiley & Sons, N.Y. (1989)). The plasmids pKKHUb2 and pKKHUb3 that expressed, respectively, the human diubiquitin and triubiquitin (both of which contain the naturally occurring 1-residue C-terminal extension, cysteine), were constructed as follows. A 1.77 kb BamHI fragment containing the human UbB (triubiquitin) gene from the plasmid pB8.3 was ligated into BamHI-digested pUC19 in the orientation that placed the 3' end of UbB adjacent to the SmaI site of the polylinker in pUC19, yielding pUbB. A 1.04 kb DraI/SmaI fragment of pUbB containing the Ub13 coding and 3' flanking regions (the DraI site is located 10 bp upstream of the UbB start codon) was subcloned into the SmaI/HincII-digested pUC19, placing the UbB start codon adjacent to the EcoRI site in the polylinker, and yielding pHUb3. This plasmid was partially digested with SalI, which cleaves once within each Ub-coding repeat (the polylinker's SalI site was removed during the construction of pHUb3); the vector-containing fragment that retained two Ub-coding repeats was isolated and self-ligated, yielding pHUb2. The inserts of pHUb2 and pHUb3 were excised with EcoRI and PstI, and subcloned into the EcoRI/PstI-cut pKK223-3, yielding, respectively, pKKHUb2 and pKKHUb3. The start codon of the Ub-coding region in these plasmids is 36 bp downstream of the Shine-Dalgarno sequence in pKK223-3.

Screening Results

E. coli carrying a plasmid expressing Ub-Arg-βgal were transformed with the S. cerevisiae genomic DNA library RB237 carried in the plasmid YCp50, plated on X-Gal plates containing antibiotics that selected for the presence of both plasmids, and incubated overnight at 37° C. Of ~800 colonies thus screened, six (named pRBW1–pRBW6) were white or pale blue, whereas the other colonies were dark blue (comparable to control colonies of E. coli transformed with the YCp50 vector alone). Three of the six candidate colonies were found to be false positives, two contained plasmids (termed pRBW1 and pRBW6) with overlapping inserts of yeast DNA, while the remaining colony contained a plasmid (termed pRBW2) with a distinct yeast DNA insert. Plasmids pRBW1 and pRBW2 were isolated and retransformed into E. coli expressing either Ub-Arg-βgal or Ub-Met-βgal. Transformants expressing Ub-Arg-βgal formed white colonies on X-Gal plates, confirming the original results, whereas transformants expressing Ub-Met-βgal formed blue colonies on these plates, indicating that the metabolic destabilization of Ub-Arg-βgal by inserts in pRBW1 and pRBW2 was N-end rule-specific. (Arg and Met are, respectively, destabilizing and stabilizing residues in the E. coli N-end rule).

Surprisingly, extracts of E. coli carrying pRBW1 or pRBW2 were inactive in an in vitro deubiquitinating assay with Ub-Met-DHFR, suggesting that Ub-specific proteases encoded by pRBW1 and pRBW2 were either inactivated in cell extracts or, alternatively, could deubiquitinate ubiquitin fusions cotranslationally but not posttranslationally. The Ub-specific protease activities conferred by pRBW1 and pRBW2 on E. coli were therefore assayed in vivo by pulse-chase analyses with Ub-Met-βgal, using a monoclonal antibody to βgal. The results confirmed that pRBW1 and pRBW2 (but not the YCp50 vector alone) did confer deubiquitinating activity on E. coli. Subsequent overexpression of Ub-specific proteases encoded by pRBW1 and pRBW2 made possible their detection in E. coli extracts as well.

Figure 3:
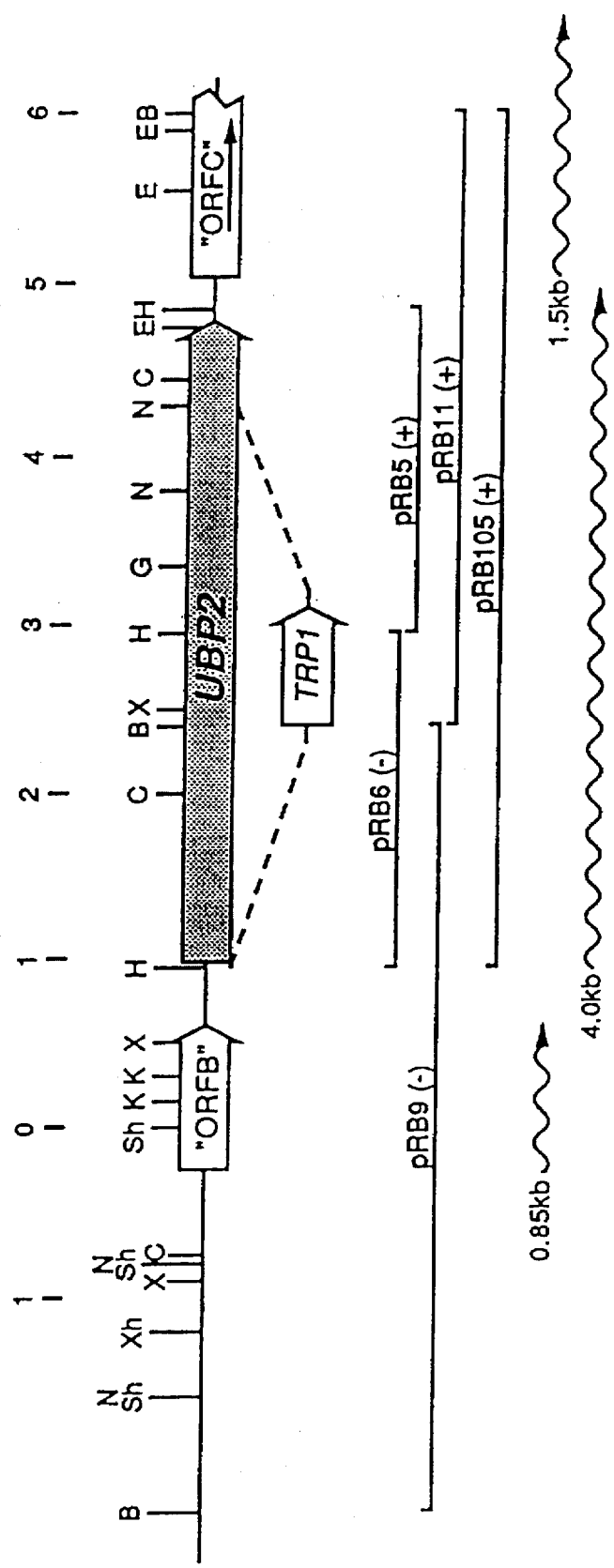
FIG. 3 is a diagram representing a restriction map of UBP2.

The ORF encoding deubiquitinating activity of pRBW2 was identified by subcloning experiments and nucleotide sequencing, and was named the UBP2 gene (FIG. 3 and Sequence I.D. Number 5). The position of the start (ATG) codon in the UBP2 was inferred so as to yield the longest (3715 bp) ORF encoding an acidic (calculated pI of 4.95), 1264-residue (145 kDa) protein.

Figure 4:
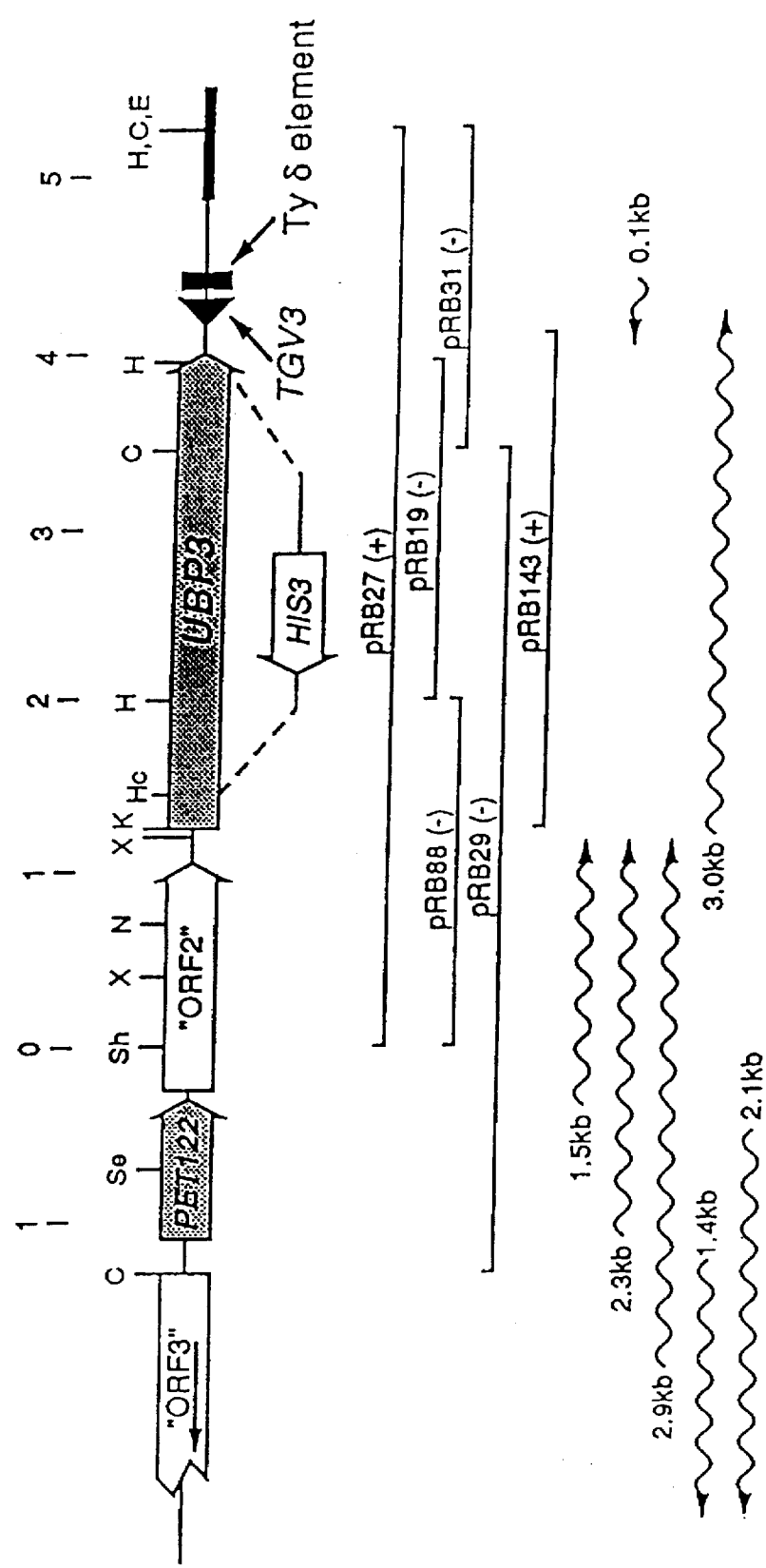
FIG. 4 is a diagram representing a restriction map of UBP3.

The ORF encoding deubiquitinating protease of pRBW1 was identified by subcloning experiments and nucleotide sequencing, and was named the UBP3 gene (FIGS. 4 and Sequence I.D. Number 7). The position of the start (ATG) codon was inferred so as to yield the longest (2736 bp) ORF, which encodes a slightly basic (calculated pI of 7.92), 912-residue (102 kDa) protein. A plasmid (pRB143) containing this ORF downstream of an E. coli promoter conferred deubiquitinating activity on E. coli.

Expression of UBP1, UBP2 and UBP3 in E. coli

The previously constructed plasmids pJT70 (pUC19-based) and pJT184 (pACYC184-based) expressed the yeast UBP1 in E. coli from the yeast UBP1 promoter, which is weakly active in E. coli. Although a 1.9 kb HindIII subclone of pRBW2 conferred deubiquitinating activity on E. coli, it contained only the 3' half of the UBP2ORF. Pilot experiments indicated that the truncated Ubp2 protein yielded variable levels of deubiquitinating activity in *E. coli* extracts. To construct a plasmid that expressed the full-length Ubp2 in *E. coli*, a 5' portion of UBP2, isolated as the 1.56 kb HindIII/XbaI fragment of pRB6 (see FIG. 3), was subcloned into pRS316 (Sikorski and Hieter, Genetics 122: 19–27 (1989)), which contains a polylinker, placing an EcoRI site close to the HindIII site in UBP2. The resulting insert was then excised as the 1.57 kb EcoRI/XbaI fragment. A 3' portion of UBP2 was isolated as the ~3.4 kb XbaI/BamHI fragment from pRB11 (see FIG. 3), and subcloned into pRS316, placing a PstI site close to the BamHI site in UBP2. The resulting insert was then excised as a ~3.4 kb XbaI/PstI fragment. This fragment and the above 1.57 kb EcoRI/XbaI fragment were ligated into the EcoRI/XbaI-cut pKK223-3, yielding (among other products) the plasmid pRB105, which contained UBP2 in the correct orientation, 50 bp downstream from the Shine-Dalgarno sequence of pKK223-3. For experiments requiting the simultaneous presence of two distinct plasmids in *E. coli*, the UBP2/rrnB terminator region of pRB105 was excised as the ~6.4 kb SphI/ScaI fragment, and subcloned into the SphI/EcoRV-cut pACYC184, yielding pRB173.

Since in the initial experiments, the Ub-specific protease activity of Ubp3 could be detected in vivo but not in *E. coli* extracts, a UBP3-overexpressing plasmid was constructed. The ~2.9 kb KpnI/DraI fragment of pRB27 that contained the entire UBP3 gene was subcloned into the KpnI/HincII-cut pUC19, placing the EcoRI and the PstI site of the plasmid near, respectively, the KpnI site and the DraI site of the introduced insert. The insert was then excised with EcoRI/PstI and subcloned into the EcoPJ/PstI-cut pKK223-3, yielding pRB143, which contained UBP3 in the correct orientation, 50 bp downstream form the Shine-Dalgarno sequence of pKK223-3. For experiments requiring the simultaneous presence of two distinct plasmids in *E. coli*, the UBP3/rrnB terminator region of pRB143 was excised as the ~4.2 kb SphI/ScaI fragment and subcloned into the SphI/EcoRV-cut pACYC184, yielding pRB 175.

In more recent experiments, UBP1, UBP2 and UBP3 were overexpressed in *E. coli* from a pKK-based expression vector (Ausubel et al., *Current Protocols in Molecular Biology*, J. Wiley & Sons, N.Y. (1989)). Each of the UBP proteins was expressed to a level where it comprises a substantial proportion (1–5%) of the total cellular protein.

Sequence Comparisons of Ub-specific Proteases

Sequence alignment of the 809-residue Ubp1, 1264-residue Ubp2 and 912-residue Ubp3 demonstrated the lack of overall sequence similarity between these proteins, as well as the presence of two short regions of statistically significant similarity that are spaced a few hundred residues apart in each of the Ubp proteases. The two regions of similarity are centered around a Cys and two His residues. As has been seen with Ubp1, neither Ubp2 nor Ubp3 have significant sequence similarities to the fourth Ub-specific protease of yeast, Yuh1 or its mammalian homologs. The region in Yuh1 and its mammalian homologs that contains a putative active-site Cys residue is not similar to the conserved "Cys" region of Ubp1–Ubp3: apart from the Cys residue, only one other residue position is occupied by an identical residue (Asn) in all six proteins. No such identities are seen in an analogous alignment of the two conserved His residues in Yuh1-like proteases with either of the conserved His residues in Ubp1–Ubp3.

In Vitro Properties of Ub-specific Proteases

The previously characterized Ubp1 protease can efficiently deubiquitinate in vitro a variety of linear ubiquitin fusion proteins, including the natural ubiquitin precursors Ubi1–Ubi3 and engineered fusions such as Ub-X-βgal and Ub-X-DHFR. Similar assays, in which an extract of *E. coli* carrying an overexpression vector-based plasmid expressing either Ubp2 (pRB105), Ubp3 (pRB143), or Yuh1 (pKKYUH1) is incubated with Ub-containing test proteins, were used to analyze in vitro the substrate specificity of these proteases. Extracts of *E. coli* carrying the UBP1-expressing plasmid pJT70 or vector alone, were also used in these assays. The cleavage products were fractionated by SDS-PAGE and visualized by immunoblotting, using anti-Ub antibodies or, with purified, $^{35}$S-labeled test proteins, directly by fluorography.

In these in vitro assays, the Ubp2 protease efficiently deubiquitinated Ub-Met-βgal and Ub-Met-DHFR, as well as Ubi2 and Ubi3, the natural precursors of ubiquitin, in which it is fused to specific ribosomal proteins. Both Ubp1 and Ubp2 released the Cys residue from Ub-Ub-Cys (diubiquitin bearing a one-residue C-terminal extension) but were unable to cleave at the Ub-Ub junction in Ub-Ub-Cys. Ubp1 and Ubp2 were also unable to cleave at the Ub-Ub junctions in the yeast polyubiquitin, a natural ubiquitin precursor containing five head-to-tail ubiquitin repeats as was previously reported for Ubp1. Thus, Ubp1 and Ubp2 efficiently cleaved in vitro after the last (Gly$^{76}$) residue of ubiquitin in all of the tested ubiquitin fusions, the Ub-Ub linkage in polyubiquitins being the single exception. However, as shown below, these proteases are able to cleave polyubiquitin when coexpressed with it *E. coli*.

Although the expression of Ubp3 in *E. coli* from the pKK overexpression vector-based plasmid pRB143 resulted in a substantial overproduction of a protein with the expected molecular mass, extracts of Ubp3-expressing *E. coli* lacked deubiquitinating activity. Since Ubp3 is certainly active in *E. coli* in vivo, it is either inactivated in cell extracts or is able to cleave ubiquitin fusions exclusively during or shortly after their ribosome-mediated synthesis.

In agreement with previously reported findings, extracts of *E. coli* expressing Yuh1 efficiently deubiquitinated short ubiquitin fusions such as Ubi2 and Ubi3. However, Yuh1 was much less active against the larger fusion Ub-Met-DHFR (a 229-residue C-terminal extension of ubiquitin), deubiquitinating at most ~50% of the fusion even after a prolonged incubation, and was virtually inactive against Ub-Met-βgal (Sequence I.D. Numbers 1–2).

In Vivo Properties of Ub-specific Proteases

As expected from their activities in *E. coli* extracts, both Ubp1, Ubp2 and Yuh1 were active in vivo against the natural ubiquitin fusions Ubi2 and Ubi3. Ubp3, which was inactive in *E. coli* extracts, efficiently deubiquitinated Ubi2 and Ubi3 when coexpressed with them in *E. coli* While Ubp1 and Ubp2 were unable to cleave at the Ub-Ub junction in polyubiquitins in vitro, both of them were active against yeast polyubiquitin when coexpressed with it in *E. coli*. In contrast, the Ubp3 protease, while active in vivo against ubiquitin fusions such as Ubi2 and Ubi3, was inactive, under the same conditions, against polyubiquitin. These distinctions among Ub-specific processing proteases indicate subtle differences in their requirements for the conformation of protein domains in the vicinities of Ub-X peptide bonds.

The in vivo deubiquitination of ubiquitin fusions such as Ub-Met-βgal by Ubp2 and Ubp3 was also followed by pulse-chase analysis, in part to confirm the findings of the original X-Gal screen. As expected, both proteases deubiquitinated Ub-Met-βgal in vivo, except that the cleavage by Ubp3 was incomplete, and a significant proportion of pulse-labeled Ub-Met-βgal remained intact 15 min after the pulse.

These results are consistent with the pattern of deubiquitination by Ubp3 that is more strictly cotranslational than that by Ubp2. In a similar pulse-chase assay, Yuh1 was unable to deubiquitinate Ub-Met-βgal in vivo, indicating that an apparently greater susceptibility of the Ub-Met peptide bond in a nascent (as distinguished from mature) Ub-Met-βgal is insufficient to allow its deubiquitination by Yuh1. By contrast, this difference is sufficient to allow a cotranslational (but apparently not posttranslational) deubiquitination of Ub-Met-βgal by Ubp3.

Equivalents

Those skilled in the art will recognize or be able to ascertain, using no more than routine experimentation, many equivalents to the specific embodiments of the invention described herein. Such equivalents are intended to be encompassed by the claims which follow the Sequence Listing.

We claim:

1. An isolated DNA encoding a ubiquitin-specific protease which specifically cleaves a ubiquitin fusion protein having a molecular weight of about 120 kilodaltons, the specific cleavage taking place in vitro between the C-terminal residue of ubiquitin and the N-terminal residue of the protein or peptide, the fusion protein being encoded by the DNA represented in Sequence ID Number 1.

2. An isolated DNA of claim 1 which is characterized by the ability to hybridize specifically with the DNA represented in Sequence I.D. Number 3 under stringent hybridization conditions.

3. An isolated DNA of claim 1 which is characterized by the ability to hybridize specifically with the DNA represented in Sequence I.D. Number 5 under stringent hybridization conditions.

4. An isolated DNA encoding a ubiquitin-specific protease which specifically cleaves a ubiquitin fusion protein having a molecular weight of about 120 kilodaltons, the specific cleavage taking place in a prokaryotic cell between the C-terminal residue of ubiquitin and the N-terminal residue of the protein or peptide, the fusion protein being encoded by the DNA represented in Sequence I.D. Number 1.

5. An isolated DNA of claim 4 which is characterized by the ability to hybridize specifically with the DNA represented in Sequence I.D. Number 3 under stringent hybridization conditions.

6. An isolated DNA of claim 4 which is characterized by the ability to hybridize specifically with the DNA represented in Sequence I.D. Number 5 under stringent hybridization conditions.

7. An isolated DNA of claim 4 which is characterized by the ability to hybridize specifically with the DNA represented in Sequence I.D. Number 7 under stringent hybridization conditions.

8. A cell transformed with:

a) a first DNA expression construct encoding a biologically active ubiquitin-specific protease comprising a DNA sequence selected from the group consisting of Sequence I.D. Number 3, Sequence I.D. Number 5 and Sequence I.D. Number 7, or a portion of these sequences, said portion encoding said protease, in expressible form; and b) a second DNA expression construct encoding ubiquitin joined to a DNA sequence encoding a protein or polypeptide of interest having a predetermined amino acid residue at its amino terminus, the ubiquitin being proteolytically cleavable by a ubiquitin-specific endoprotease at the junction with the amino-terminus of the protein or polypeptide of interest such that cleavage results in the exposure of the predetermined amino-terminal residue of the protein or polypeptide of interest.

9. A cell of claim 8 which is a prokaryotic cell.

10. A cell of claim 8 which is E. coli.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
      ( A ) LENGTH: 3365 base pairs
      ( B ) TYPE: nucleic acid
      ( C ) STRANDEDNESS: double
      ( D ) TOPOLOGY: linear ( i x ) FEATURE:
      ( A ) NAME/KEY: CDS
      ( B ) LOCATION: 1..3363

( x i ) SEQUENCE DESCRIPTION: SEQ ID NO:1:

```
ATG CAG ATT TTC GTC AAG ACT TTG ACC GGT AAA ACC ATA ACA TTG GAA      48
Met Gln Ile Phe Val Lys Thr Leu Thr Gly Lys Thr Ile Thr Leu Glu
 1               5                  10                  15

GTT GAA TCT TCC GAT ACC ATC GAC AAC GTT AAG TCG AAA ATT CAA GAC      96
Val Glu Ser Ser Asp Thr Ile Asp Asn Val Lys Ser Lys Ile Gln Asp
             20                  25                  30

AAG GAA GGT ATC CCT CCA GAT CAA CAA AGA TTG ATC TTT GCC GGT AAG     144
Lys Glu Gly Ile Pro Pro Asp Gln Gln Arg Leu Ile Phe Ala Gly Lys
         35                  40                  45

CAG CTA GAA GAC GGT AGA ACG CTG TCT GAT TAC AAC ATT CAG AAG GAG     192
Gln Leu Glu Asp Gly Arg Thr Leu Ser Asp Tyr Asn Ile Gln Lys Glu
     50                  55                  60

TCC ACC TTA CAT CTT GTG CTA AGG CTA AGA GGT GGT ATG CAC GGA TCC     240
Ser Thr Leu His Leu Val Leu Arg Leu Arg Gly Gly Met His Gly Ser
 65                  70                  75                  80

GGA GCT TGG CTG TTG CCC GTC TCA CTG GTG AAA AGA AAA ACC ACC CTG     288
Gly Ala Trp Leu Leu Pro Val Ser Leu Val Lys Arg Lys Thr Thr Leu
                 85                  90                  95

GCG CCC AAT ACG CAA ACC GCC TCT CCC CGC GCG TTG GCC GAT TCA TTA     336
Ala Pro Asn Thr Gln Thr Ala Ser Pro Arg Ala Leu Ala Asp Ser Leu
            100                 105                 110

ATG CAG CTG GCA CGA CAG GTT TCC CGA CTT AAT CGC CTT GCA GCA CAT     384
Met Gln Leu Ala Arg Gln Val Ser Arg Leu Asn Arg Leu Ala Ala His
        115                 120                 125

CCC CCT TTC GCC AGC TGG CGT AAT AGC GAA GAG GCC CGC ACC GAT CGC     432
Pro Pro Phe Ala Ser Trp Arg Asn Ser Glu Glu Ala Arg Thr Asp Arg
    130                 135                 140

CCT TCC CAA CAG TTG CGC AGC CTG AAT GGC GAA TGG CGC TTT GCC TGG     480
Pro Ser Gln Gln Leu Arg Ser Leu Asn Gly Glu Trp Arg Phe Ala Trp
145                 150                 155                 160

TTT CCG GCA CCA GAA GCG GTG CCG GAA AGC TGG CTG GAG TGC GAT CTT     528
Phe Pro Ala Pro Glu Ala Val Pro Glu Ser Trp Leu Glu Cys Asp Leu
                165                 170                 175

CCT GAG GCC GAT ACT GTC GTC GTC CCC TCA AAC TGG CAG ATG CAC GGT     576
```

```
                Pro Glu Ala Asp Thr Val Val Val Pro Ser Asn Trp Gln Met His Gly
                            180                     185                 190

TAC GAT GCG CCC ATC TAC ACC AAC GTA ACC TAT CCC ATT ACG GTC AAT          624
Tyr Asp Ala Pro Ile Tyr Thr Asn Val Thr Tyr Pro Ile Thr Val Asn
        195                 200                 205

CCG CCG TTT GTT CCC ACG GAG AAT CCG ACG GGT TGT TAC TCG CTC ACA          672
Pro Pro Phe Val Pro Thr Glu Asn Pro Thr Gly Cys Tyr Ser Leu Thr
    210                 215                 220

TTT AAT GTT GAT GAA AGC TGG CTA CAG GAA GGC CAG ACG CGA ATT ATT          720
Phe Asn Val Asp Glu Ser Trp Leu Gln Glu Gly Gln Thr Arg Ile Ile
225             230                 235                     240

TTT GAT GGC GTT AAC TCG GCG TTT CAT CTG TGG TGC AAC GGG CGC TGG          768
Phe Asp Gly Val Asn Ser Ala Phe His Leu Trp Cys Asn Gly Arg Trp
                245                 250                 255

GTC GGT TAC GGC CAG GAC AGT CGT TTG CCG TCT GAA TTT GAC CTG AGC          816
Val Gly Tyr Gly Gln Asp Ser Arg Leu Pro Ser Glu Phe Asp Leu Ser
            260                 265                 270

GCA TTT TTA CGC GCC GGA GAA AAC CGC CTC GCG GTG ATG GTG CTG CGT          864
Ala Phe Leu Arg Ala Gly Glu Asn Arg Leu Ala Val Met Val Leu Arg
        275                 280                 285

TGG AGT GAC GGC AGT TAT CTG GAA GAT CAG GAT ATG TGG CGG ATG AGC          912
Trp Ser Asp Gly Ser Tyr Leu Glu Asp Gln Asp Met Trp Arg Met Ser
    290                 295                 300

GGC ATT TTC CGT GAC GTC TCG TTG CTG CAT AAA CCG ACT ACA CAA ATC          960
Gly Ile Phe Arg Asp Val Ser Leu Leu His Lys Pro Thr Thr Gln Ile
305             310                 315                     320

AGC GAT TTC CAT GTT GCC ACT CGC TTT AAT GAT GAT TTC AGC CGC GCT         1008
Ser Asp Phe His Val Ala Thr Arg Phe Asn Asp Asp Phe Ser Arg Ala
                325                 330                 335

GTA CTG GAG GCT GAA GTT CAG ATG TGC GGC GAG TTG CGT GAC TAC CTA         1056
Val Leu Glu Ala Glu Val Gln Met Cys Gly Glu Leu Arg Asp Tyr Leu
            340                 345                 350

CGG GTA ACA GTT TCT TTA TGG CAG GGT GAA ACG CAG GTC GCC AGC GGC         1104
Arg Val Thr Val Ser Leu Trp Gln Gly Glu Thr Gln Val Ala Ser Gly
        355                 360                 365

ACC GCG CCT TTC GGC GGT GAA ATT ATC GAT GAG CGT GGT GGT TAT GCC         1152
Thr Ala Pro Phe Gly Gly Glu Ile Ile Asp Glu Arg Gly Gly Tyr Ala
    370                 375                 380

GAT CGC GTC ACA CTA CGT CTG AAC GTC GAA AAC CCG AAA CTG TGG AGC         1200
Asp Arg Val Thr Leu Arg Leu Asn Val Glu Asn Pro Lys Leu Trp Ser
385             390                 395                     400

GCC GAA ATC CCG AAT CTC TAT CGT GCG GTG GTT GAA CTG CAC ACC GCC         1248
Ala Glu Ile Pro Asn Leu Tyr Arg Ala Val Val Glu Leu His Thr Ala
                405                 410                 415

GAC GGC ACG CTG ATT GAA GCA GAA GCC TGC GAT GTC GGT TTC CGC GAG         1296
Asp Gly Thr Leu Ile Glu Ala Glu Ala Cys Asp Val Gly Phe Arg Glu
            420                 425                 430

GTG CGG ATT GAA AAT GGT CTG CTG CTG CTG AAC GGC AAG CCG TTG CTG         1344
Val Arg Ile Glu Asn Gly Leu Leu Leu Leu Asn Gly Lys Pro Leu Leu
        435                 440                 445

ATT CGA GGC GTT AAC CGT CAC GAG CAT CAT CCT CTG CAT GGT CAG GTC         1392
Ile Arg Gly Val Asn Arg His Glu His His Pro Leu His Gly Gln Val
    450                 455                 460

ATG GAT GAG CAG ACG ATG GTG CAG GAT ATC CTG CTG ATG AAG CAG AAC         1440
Met Asp Glu Gln Thr Met Val Gln Asp Ile Leu Leu Met Lys Gln Asn
465             470                 475                     480

AAC TTT AAC GCC GTG CGC TGT TCG CAT TAT CCG AAC CAT CCG CTG TGG         1488
Asn Phe Asn Ala Val Arg Cys Ser His Tyr Pro Asn His Pro Leu Trp
                485                 490                 495

TAC ACG CTG TGC GAC CGC TAC GGC CTG TAT GTG GTG GAT GAA GCC AAT         1536
```

```
            Tyr Thr Leu Cys Asp Arg Tyr Gly Leu Tyr Val Val Asp Glu Ala Asn
                        500                 505                 510

ATT GAA ACC CAC GGC ATG GTG CCA ATG AAT CGT CTG ACC GAT GAT CCG   1584
Ile Glu Thr His Gly Met Val Pro Met Asn Arg Leu Thr Asp Asp Pro
            515                 520                 525

CGC TGG CTA CCG GCG ATG AGC GAA CGC GTA ACG CGA ATG GTG CAG CGC   1632
Arg Trp Leu Pro Ala Met Ser Glu Arg Val Thr Arg Met Val Gln Arg
        530                 535                 540

GAT CGT AAT CAC CCG AGT GTG ATC ATC TGG TCG CTG GGG AAT GAA TCA   1680
Asp Arg Asn His Pro Ser Val Ile Ile Trp Ser Leu Gly Asn Glu Ser
545                 550                 555                 560

GGC CAC GGC GCT AAT CAC GAC GCG CTG TAT CGC TGG ATC AAA TCT GTC   1728
Gly His Gly Ala Asn His Asp Ala Leu Tyr Arg Trp Ile Lys Ser Val
                565                 570                 575

GAT CCT TCC CGC CCG GTG CAG TAT GAA GGC GGC GGA GCC GAC ACC ACG   1776
Asp Pro Ser Arg Pro Val Gln Tyr Glu Gly Gly Gly Ala Asp Thr Thr
            580                 585                 590

GCC ACC GAT ATT ATT TGC CCG ATG TAC GCG CGC GTG GAT GAA GAC CAG   1824
Ala Thr Asp Ile Ile Cys Pro Met Tyr Ala Arg Val Asp Glu Asp Gln
        595                 600                 605

CCC TTC CCG GCT GTG CCG AAA TGG TCC ATC AAA AAA TGG CTT TCG CTA   1872
Pro Phe Pro Ala Val Pro Lys Trp Ser Ile Lys Lys Trp Leu Ser Leu
610                 615                 620

CCT GGA GAG ACG CGC CCG CTG ATC CTT TGC GAA TAC GCC CAC GCG ATG   1920
Pro Gly Glu Thr Arg Pro Leu Ile Leu Cys Glu Tyr Ala His Ala Met
625                 630                 635                 640

GGT AAC AGT CTT GGC GGT TTC GCT AAA TAC TGG CAG GCG TTT CGT CAG   1968
Gly Asn Ser Leu Gly Gly Phe Ala Lys Tyr Trp Gln Ala Phe Arg Gln
                645                 650                 655

TAT CCC CGT TTA CAG GGC GGC TTC GTC TGG GAC TGG GTG GAT CAG TCG   2016
Tyr Pro Arg Leu Gln Gly Gly Phe Val Trp Asp Trp Val Asp Gln Ser
            660                 665                 670

CTG ATT AAA TAT GAT GAA AAC GGC AAC CCG TGG TCG GCT TAC GGC GGT   2064
Leu Ile Lys Tyr Asp Glu Asn Gly Asn Pro Trp Ser Ala Tyr Gly Gly
        675                 680                 685

GAT TTT GGC GAT ACG CCG AAC GAT CGC CAG TTC TGT ATG AAC GGT CTG   2112
Asp Phe Gly Asp Thr Pro Asn Asp Arg Gln Phe Cys Met Asn Gly Leu
690                 695                 700

GTC TTT GCC GAC CGC ACG CCG CAT CCA GCG CTG ACG GAA GCA AAA CAC   2160
Val Phe Ala Asp Arg Thr Pro His Pro Ala Leu Thr Glu Ala Lys His
705                 710                 715                 720

CAG CAG CAG TTT TTC CAG TTC CGT TTA TCC GGG CAA ACC ATC GAA GTG   2208
Gln Gln Gln Phe Phe Gln Phe Arg Leu Ser Gly Gln Thr Ile Glu Val
                725                 730                 735

ACC AGC GAA TAC CTG TTC CGT CAT AGC GAT AAC GAG CTC CTG CAC TGG   2256
Thr Ser Glu Tyr Leu Phe Arg His Ser Asp Asn Glu Leu Leu His Trp
            740                 745                 750

ATG GTG GCG CTG GAT GGT AAG CCG CTG GCA AGC GGT GAA GTG CCT CTG   2304
Met Val Ala Leu Asp Gly Lys Pro Leu Ala Ser Gly Glu Val Pro Leu
        755                 760                 765

GAT GTC GCT CCA CAA GGT AAA CAG TTG ATT GAA CTG CCT GAA CTA CCG   2352
Asp Val Ala Pro Gln Gly Lys Gln Leu Ile Glu Leu Pro Glu Leu Pro
770                 775                 780

CAG CCG GAG AGC GCC GGG CAA CTC TGG CTC ACA GTA CGC GTA GTG CAA   2400
Gln Pro Glu Ser Ala Gly Gln Leu Trp Leu Thr Val Arg Val Val Gln
785                 790                 795                 800

CCG AAC GCG ACC GCA TGG TCA GAA GCC GGG CAC ATC AGC GCC TGG CAG   2448
Pro Asn Ala Thr Ala Trp Ser Glu Ala Gly His Ile Ser Ala Trp Gln
                805                 810                 815

CAG TGG CGT CTG GCG GAA AAC CTC AGT GTG ACG CTC CCC GCC GCG TCC   2496
```

-continued

```
         Gln  Trp  Arg  Leu  Ala  Glu  Asn  Leu  Ser  Val  Thr  Leu  Pro  Ala  Ala  Ser
                        820                 825                      830

CAC GCC ATC CCG CAT CTG ACC ACC AGC GAA ATG GAT TTT TGC ATC GAG              2544
His Ala Ile Pro His Leu Thr Thr Ser Glu Met Asp Phe Cys Ile Glu
        835                 840                 845

CTG GGT AAT AAG CGT TGG CAA TTT AAC CGC CAG TCA GGC TTT CTT TCA              2592
Leu Gly Asn Lys Arg Trp Gln Phe Asn Arg Gln Ser Gly Phe Leu Ser
850                 855                 860

CAG ATG TGG ATT GGC GAT AAA AAA CAA CTG CTG ACG CCG CTG CGC GAT              2640
Gln Met Trp Ile Gly Asp Lys Lys Gln Leu Leu Thr Pro Leu Arg Asp
865                 870                 875                 880

CAG TTC ACC CGT GCA CCG CTG GAT AAC GAC ATT GGC GTA AGT GAA GCG              2688
Gln Phe Thr Arg Ala Pro Leu Asp Asn Asp Ile Gly Val Ser Glu Ala
                885                 890                 895

ACC CGC ATT GAC CCT AAC GCC TGG GTC GAA CGC TGG AAG GCG GCG GGC              2736
Thr Arg Ile Asp Pro Asn Ala Trp Val Glu Arg Trp Lys Ala Ala Gly
            900                 905                 910

CAT TAC CAG GCC GAA GCA GCG TTG TTG CAG TGC ACG GCA GAT ACA CTT              2784
His Tyr Gln Ala Glu Ala Ala Leu Leu Gln Cys Thr Ala Asp Thr Leu
        915                 920                 925

GCT GAT GCG GTG CTG ATT ACG ACC GCT CAC GCG TGG CAG CAT CAG GGG              2832
Ala Asp Ala Val Leu Ile Thr Thr Ala His Ala Trp Gln His Gln Gly
930                 935                 940

AAA ACC TTA TTT ATC AGC CGG AAA ACC TAC CGG ATT GAT GGT AGT GGT              2880
Lys Thr Leu Phe Ile Ser Arg Lys Thr Tyr Arg Ile Asp Gly Ser Gly
945                 950                 955                 960

CAA ATG GCG ATT ACC GTT GAT GTT GAA GTG GCG AGC GAT ACA CCG CAT              2928
Gln Met Ala Ile Thr Val Asp Val Glu Val Ala Ser Asp Thr Pro His
                965                 970                 975

CCG GCG CGG ATT GGC CTG AAC TGC CAG CTG GCG CAG GTA GCA GAG CGG              2976
Pro Ala Arg Ile Gly Leu Asn Cys Gln Leu Ala Gln Val Ala Glu Arg
            980                 985                 990

GTA AAC TGG CTC GGA TTA GGG CCG CAA GAA AAC TAT CCC GAC CGC CTT              3024
Val Asn Trp Leu Gly Leu Gly Pro Gln Glu Asn Tyr Pro Asp Arg Leu
        995                1000                1005

ACT GCC GCC TGT TTT GAC CGC TGG GAT CTG CCA TTG TCA GAC ATG TAT              3072
Thr Ala Ala Cys Phe Asp Arg Trp Asp Leu Pro Leu Ser Asp Met Tyr
1010                1015                1020

ACC CCG TAC GTC TTC CCG AGC GAA AAC GGT CTG CGC TGC GGG ACG CGC              3120
Thr Pro Tyr Val Phe Pro Ser Glu Asn Gly Leu Arg Cys Gly Thr Arg
1025                1030                1035                1040

GAA TTG AAT TAT GGC CCA CAC CAG TGG CGC GGC GAC TTC CAG TTC AAC              3168
Glu Leu Asn Tyr Gly Pro His Gln Trp Arg Gly Asp Phe Gln Phe Asn
                1045                1050                1055

ATC AGC CGC TAC AGT CAA CAG CAA CTG ATG GAA ACC AGC CAT CGC CAT              3216
Ile Ser Arg Tyr Ser Gln Gln Gln Leu Met Glu Thr Ser His Arg His
            1060                1065                1070

CTG CTG CAC GCG GAA GAA GGC ACA TGG CTG AAT ATC GAC GGT TTC CAT              3264
Leu Leu His Ala Glu Glu Gly Thr Trp Leu Asn Ile Asp Gly Phe His
        1075                1080                1085

ATG GGG ATT GGT GGC GAC GAC TCC TGG AGC CCG TCA GTA TCG GCG GAA              3312
Met Gly Ile Gly Gly Asp Asp Ser Trp Ser Pro Ser Val Ser Ala Glu
1090                1095                1100

TTC CAG CTG AGC GCC GGT CGC TAC CAT TAC CAG TTG GTC TGG TGT CAA              3360
Phe Gln Leu Ser Ala Gly Arg Tyr His Tyr Gln Leu Val Trp Cys Gln
1105                1110                1115                1120

AAA TA                                                                       3365
Lys
```

( 2 ) INFORMATION FOR SEQ ID NO:2:

(i) SEQUENCE CHARACTERISTICS:
   (A) LENGTH: 1121 amino acids
   (B) TYPE: amino acid
   (D) TOPOLOGY: linear (ii) MOLECULE TYPE: protein (xi) SEQUENCE DESCRIPTION: SEQ ID NO:2:

```
Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met His Gly Ser
65                  70                  75                  80

Gly Ala Trp Leu Leu Pro Val Ser Leu Val Lys Arg Lys Thr Thr Leu
                85                  90                  95

Ala Pro Asn Thr Gln Thr Ala Ser Pro Arg Ala Leu Ala Asp Ser Leu
            100                 105                 110

Met Gln Leu Ala Arg Gln Val Ser Arg Leu Asn Arg Leu Ala Ala His
        115                 120                 125

Pro Pro Phe Ala Ser Trp Arg Asn Ser Glu Glu Ala Arg Thr Asp Arg
130                 135                 140

Pro Ser Gln Gln Leu Arg Ser Leu Asn Gly Glu Trp Arg Phe Ala Trp
145                 150                 155                 160

Phe Pro Ala Pro Glu Ala Val Pro Glu Ser Trp Leu Glu Cys Asp Leu
                165                 170                 175

Pro Glu Ala Asp Thr Val Val Val Pro Ser Asn Trp Gln Met His Gly
            180                 185                 190

Tyr Asp Ala Pro Ile Tyr Thr Asn Val Thr Tyr Pro Ile Thr Val Asn
        195                 200                 205

Pro Pro Phe Val Pro Thr Glu Asn Pro Thr Gly Cys Tyr Ser Leu Thr
210                 215                 220

Phe Asn Val Asp Glu Ser Trp Leu Gln Glu Gly Gln Thr Arg Ile Ile
225                 230                 235                 240

Phe Asp Gly Val Asn Ser Ala Phe His Leu Trp Cys Asn Gly Arg Trp
                245                 250                 255

Val Gly Tyr Gly Gln Asp Ser Arg Leu Pro Ser Glu Phe Asp Leu Ser
            260                 265                 270

Ala Phe Leu Arg Ala Gly Glu Asn Arg Leu Ala Val Met Val Leu Arg
        275                 280                 285

Trp Ser Asp Gly Ser Tyr Leu Glu Asp Gln Asp Met Trp Arg Met Ser
290                 295                 300

Gly Ile Phe Arg Asp Val Ser Leu Leu His Lys Pro Thr Thr Gln Ile
305                 310                 315                 320

Ser Asp Phe His Val Ala Thr Arg Phe Asn Asp Asp Phe Ser Arg Ala
                325                 330                 335

Val Leu Glu Ala Glu Val Gln Met Cys Gly Glu Leu Arg Asp Tyr Leu
            340                 345                 350

Arg Val Thr Val Ser Leu Trp Gln Gly Glu Thr Gln Val Ala Ser Gly
        355                 360                 365

Thr Ala Pro Phe Gly Gly Glu Ile Ile Asp Glu Arg Gly Gly Tyr Ala
```

-continued

```
              370                          375                          380
Asp  Arg  Val  Thr  Leu  Arg  Leu  Asn  Val  Glu  Asn  Pro  Lys  Leu  Trp  Ser
385                      390                      395                      400

Ala  Glu  Ile  Pro  Asn  Leu  Tyr  Arg  Ala  Val  Val  Glu  Leu  His  Thr  Ala
                    405                      410                      415

Asp  Gly  Thr  Leu  Ile  Glu  Ala  Glu  Ala  Cys  Asp  Val  Gly  Phe  Arg  Glu
                    420                      425                      430

Val  Arg  Ile  Glu  Asn  Gly  Leu  Leu  Leu  Leu  Asn  Gly  Lys  Pro  Leu  Leu
               435                      440                      445

Ile  Arg  Gly  Val  Asn  Arg  His  Glu  His  His  Pro  Leu  His  Gly  Gln  Val
     450                      455                      460

Met  Asp  Glu  Gln  Thr  Met  Val  Gln  Asp  Ile  Leu  Leu  Met  Lys  Gln  Asn
465                      470                      475                      480

Asn  Phe  Asn  Ala  Val  Arg  Cys  Ser  His  Tyr  Pro  Asn  His  Pro  Leu  Trp
                    485                      490                      495

Tyr  Thr  Leu  Cys  Asp  Arg  Tyr  Gly  Leu  Tyr  Val  Val  Asp  Glu  Ala  Asn
                    500                      505                      510

Ile  Glu  Thr  His  Gly  Met  Val  Pro  Met  Asn  Arg  Leu  Thr  Asp  Asp  Pro
               515                      520                      525

Arg  Trp  Leu  Pro  Ala  Met  Ser  Glu  Arg  Val  Thr  Arg  Met  Val  Gln  Arg
530                      535                      540

Asp  Arg  Asn  His  Pro  Ser  Val  Ile  Ile  Trp  Ser  Leu  Gly  Asn  Glu  Ser
545                      550                      555                      560

Gly  His  Gly  Ala  Asn  His  Asp  Ala  Leu  Tyr  Arg  Trp  Ile  Lys  Ser  Val
                    565                      570                      575

Asp  Pro  Ser  Arg  Pro  Val  Gln  Tyr  Glu  Gly  Gly  Gly  Ala  Asp  Thr  Thr
               580                      585                      590

Ala  Thr  Asp  Ile  Ile  Cys  Pro  Met  Tyr  Ala  Arg  Val  Asp  Glu  Asp  Gln
          595                      600                      605

Pro  Phe  Pro  Ala  Val  Pro  Lys  Trp  Ser  Ile  Lys  Lys  Trp  Leu  Ser  Leu
     610                      615                      620

Pro  Gly  Glu  Thr  Arg  Pro  Leu  Ile  Leu  Cys  Glu  Tyr  Ala  His  Ala  Met
625                      630                      635                      640

Gly  Asn  Ser  Leu  Gly  Gly  Phe  Ala  Lys  Tyr  Trp  Gln  Ala  Phe  Arg  Gln
                    645                      650                      655

Tyr  Pro  Arg  Leu  Gln  Gly  Gly  Phe  Val  Trp  Asp  Trp  Val  Asp  Gln  Ser
               660                      665                      670

Leu  Ile  Lys  Tyr  Asp  Glu  Asn  Gly  Asn  Pro  Trp  Ser  Ala  Tyr  Gly  Gly
          675                      680                      685

Asp  Phe  Gly  Asp  Thr  Pro  Asn  Asp  Arg  Gln  Phe  Cys  Met  Asn  Gly  Leu
     690                      695                      700

Val  Phe  Ala  Asp  Arg  Thr  Pro  His  Pro  Ala  Leu  Thr  Glu  Ala  Lys  His
705                      710                      715                      720

Gln  Gln  Gln  Phe  Phe  Gln  Phe  Arg  Leu  Ser  Gly  Gln  Thr  Ile  Glu  Val
                    725                      730                      735

Thr  Ser  Glu  Tyr  Leu  Phe  Arg  His  Ser  Asp  Asn  Glu  Leu  Leu  His  Trp
                    740                      745                      750

Met  Val  Ala  Leu  Asp  Gly  Lys  Pro  Leu  Ala  Ser  Gly  Glu  Val  Pro  Leu
               755                      760                      765

Asp  Val  Ala  Pro  Gln  Gly  Lys  Gln  Leu  Ile  Glu  Leu  Pro  Glu  Leu  Pro
     770                      775                      780

Gln  Pro  Glu  Ser  Ala  Gly  Gln  Leu  Trp  Leu  Thr  Val  Arg  Val  Val  Gln
785                      790                      795                      800
```

|       |       |       |       |       |       |       |       |       |       |       |       |       |       |       |
|-------|-------|-------|-------|-------|-------|-------|-------|-------|-------|-------|-------|-------|-------|-------|
| Pro   | Asn   | Ala   | Thr   | Ala   | Trp   | Ser   | Glu   | Ala   | Gly   | His   | Ile   | Ser   | Ala   | Trp   | Gln   |
|       |       |       |       | 805   |       |       |       |       | 810   |       |       |       |       | 815   |       |

Gln Trp Arg Leu Ala Glu Asn Leu Ser Val Thr Leu Pro Ala Ala Ser
    820              825             830

His Ala Ile Pro His Leu Thr Thr Ser Glu Met Asp Phe Cys Ile Glu
    835             840             845

Leu Gly Asn Lys Arg Trp Gln Phe Asn Arg Gln Ser Gly Phe Leu Ser
850              855              860

Gln Met Trp Ile Gly Asp Lys Lys Gln Leu Leu Thr Pro Leu Arg Asp
865              870              875              880

Gln Phe Thr Arg Ala Pro Leu Asp Asn Asp Ile Gly Val Ser Glu Ala
              885              890              895

Thr Arg Ile Asp Pro Asn Ala Trp Val Glu Arg Trp Lys Ala Ala Gly
              900              905              910

His Tyr Gln Ala Glu Ala Ala Leu Leu Gln Cys Thr Ala Asp Thr Leu
         915              920              925

Ala Asp Ala Val Leu Ile Thr Thr Ala His Ala Trp Gln His Gln Gly
    930              935              940

Lys Thr Leu Phe Ile Ser Arg Lys Thr Tyr Arg Ile Asp Gly Ser Gly
945              950              955              960

Gln Met Ala Ile Thr Val Asp Val Glu Val Ala Ser Asp Thr Pro His
              965              970              975

Pro Ala Arg Ile Gly Leu Asn Cys Gln Leu Ala Gln Val Ala Glu Arg
              980              985              990

Val Asn Trp Leu Gly Leu Gly Pro Gln Glu Asn Tyr Pro Asp Arg Leu
         995              1000             1005

Thr Ala Ala Cys Phe Asp Arg Trp Asp Leu Pro Leu Ser Asp Met Tyr
    1010             1015             1020

Thr Pro Tyr Val Phe Pro Ser Glu Asn Gly Leu Arg Cys Gly Thr Arg
1025             1030             1035             1040

Glu Leu Asn Tyr Gly Pro His Gln Trp Arg Gly Asp Phe Gln Phe Asn
              1045             1050             1055

Ile Ser Arg Tyr Ser Gln Gln Gln Leu Met Glu Thr Ser His Arg His
              1060             1065             1070

Leu Leu His Ala Glu Glu Gly Thr Trp Leu Asn Ile Asp Gly Phe His
         1075             1080             1085

Met Gly Ile Gly Gly Asp Asp Ser Trp Ser Pro Ser Val Ser Ala Glu
    1090             1095             1100

Phe Gln Leu Ser Ala Gly Arg Tyr His Tyr Gln Leu Val Trp Cys Gln
1105             1110             1115             1120

Lys ( 2 ) INFORMATION FOR SEQ ID NO:3:

( i ) SEQUENCE CHARACTERISTICS:
        ( A ) LENGTH: 2845 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 193..2619

( x i ) SEQUENCE DESCRIPTION: SEQ ID NO:3:

TGTGATCTGC GTCCTTTTTT TCTCAGGAAA AAAAAATTTT ATAGACATTC AAAGAATAGA   60

AGCGATTGTC AAAATTCGCT TCTCCTTTCT TTTCCATTAT AACGTCTGAT CATTTTACGT  120

-continued

| | |
|---|---|
| CTTCAGTGCC CTCCCTTGTT CGAAACTAGA TACTTTCGAA CACTTCTCCC CTTTTAATCT | 180 |

```
ACAAAATTTT GT ATG GAT TTG TTT ATT GAA AGC AAG ATA AAC AGT TTA        228
              Met Asp Leu Phe Ile Glu Ser Lys Ile Asn Ser Leu
              1               5                   10

TTA CAA TTT TTA TTT GGT TCC CGA CAG GAT TTT TTG AGA AAT TTT AAA      276
Leu Gln Phe Leu Phe Gly Ser Arg Gln Asp Phe Leu Arg Asn Phe Lys
            15                  20                  25

ACT TGG AGT AAC AAC AAT AAC AAT CTA TCG ATT TAT TTA TTA ATT TTT      324
Thr Trp Ser Asn Asn Asn Asn Asn Leu Ser Ile Tyr Leu Leu Ile Phe
        30                  35                  40

GGC ATA GTA GTA TTT TTT TAT AAA AAA CCA GAC CAT CTA AAC TAC ATT      372
Gly Ile Val Val Phe Phe Tyr Lys Lys Pro Asp His Leu Asn Tyr Ile
45              50                  55                  60

GTT GAG AGC GTT AGT GAA ATG ACA ACA AAC TTC AGA AAT AAT AAT AGC      420
Val Glu Ser Val Ser Glu Met Thr Thr Asn Phe Arg Asn Asn Asn Ser
                65                  70                  75

CTT AGC CGT TGG TTG CCC AGA AGT AAG TTT ACC CAC TTA GAC GAA GAG      468
Leu Ser Arg Trp Leu Pro Arg Ser Lys Phe Thr His Leu Asp Glu Glu
            80                  85                  90

ATC TTG AAA AGA GGT GGT TTC ATT GCT GGT TTA GTT AAT GAT GGT AAC      516
Ile Leu Lys Arg Gly Gly Phe Ile Ala Gly Leu Val Asn Asp Gly Asn
        95                  100                 105

ACT TGT TTT ATG AAC TCT GTT TTG CAA TCA TTG GCA TCA TCC AGA GAA      564
Thr Cys Phe Met Asn Ser Val Leu Gln Ser Leu Ala Ser Ser Arg Glu
    110                 115                 120

TTA ATG GAG TTC TTG GAC AAT AAT GTC ATA AGG ACC TAT GAG GAG ATA      612
Leu Met Glu Phe Leu Asp Asn Asn Val Ile Arg Thr Tyr Glu Glu Ile
125                 130                 135                 140

GAA CAA AAT GAA CAC AAT GAA GAA GGA AAC GGG CAA GAA TCT GCT CAA      660
Glu Gln Asn Glu His Asn Glu Glu Gly Asn Gly Gln Glu Ser Ala Gln
                145                 150                 155

GAT GAA GCC ACT CAT AAG AAA AAC ACT CGT AAG GGT GGC AAA GTT TAT      708
Asp Glu Ala Thr His Lys Lys Asn Thr Arg Lys Gly Gly Lys Val Tyr
            160                 165                 170

GGT AAG CAT AAG AAG AAA TTG AAT AGG AAG TCA AGT TCG AAA GAA GAC      756
Gly Lys His Lys Lys Lys Leu Asn Arg Lys Ser Ser Ser Lys Glu Asp
        175                 180                 185

GAA GAA AAG AGC CAG GAG CCA GAT ATC ACT TTC AGT GTC GCC TTA AGG      804
Glu Glu Lys Ser Gln Glu Pro Asp Ile Thr Phe Ser Val Ala Leu Arg
190                 195                 200

GAT CTA CTT TCT GCC TTA AAT GCG AAG TAT TAT CGG GAT AAA CCC TAT      852
Asp Leu Leu Ser Ala Leu Asn Ala Lys Tyr Tyr Arg Asp Lys Pro Tyr
205                 210                 215                 220

TTC AAA ACC AAT AGT TTA TTG AAA GCA ATG TCC AAA TCT CCA AGA AAA      900
Phe Lys Thr Asn Ser Leu Leu Lys Ala Met Ser Lys Ser Pro Arg Lys
                225                 230                 235

AAT ATT CTT CTT GGC TAC GAC CAA GAG GAC GCG CAA GAA TTC TTC CAG      948
Asn Ile Leu Leu Gly Tyr Asp Gln Glu Asp Ala Gln Glu Phe Phe Gln
            240                 245                 250

AAC ATA CTA GCC GAG TTG GAA AGT AAC GTT AAA TCA TTG AAT ACT GAA      996
Asn Ile Leu Ala Glu Leu Glu Ser Asn Val Lys Ser Leu Asn Thr Glu
        255                 260                 265

AAA CTA GAT ACC ACT CCA GTT GCG AAA TCA GAA TTA CCC GAT GAT GCT     1044
Lys Leu Asp Thr Thr Pro Val Ala Lys Ser Glu Leu Pro Asp Asp Ala
270                 275                 280

TTA GTA GGT CAA CTT AAC CTT GGT GAA GTT GGC ACT GTT TAC ATT CCA     1092
Leu Val Gly Gln Leu Asn Leu Gly Glu Val Gly Thr Val Tyr Ile Pro
285                 290                 295                 300

ACT GAA CAG ATT GAT CCT AAC TCT ATA CTA CAT GAC AAG TCC ATT CAA     1140
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Thr | Glu | Gln | Ile | Asp | Pro | Asn | Ser | Ile | Leu | His | Asp | Lys | Ser | Ile | Gln |      |
|     |     |     |     | 305 |     |     |     |     | 310 |     |     |     |     | 315 |     |      |
| AAT | TTC | ACA | CCT | TTC | AAA | CTA | ATG | ACT | CCT | TTA | GAT | GGT | ATC | ACG | GCA | 1188 |
| Asn | Phe | Thr | Pro | Phe | Lys | Leu | Met | Thr | Pro | Leu | Asp | Gly | Ile | Thr | Ala |      |
|     |     |     | 320 |     |     |     |     | 325 |     |     |     |     | 330 |     |     |      |
| GAA | AGA | ATT | GGT | TGT | TTA | CAG | TGT | GGT | GAG | AAC | GGT | GGC | ATA | AGA | TAT | 1236 |
| Glu | Arg | Ile | Gly | Cys | Leu | Gln | Cys | Gly | Glu | Asn | Gly | Gly | Ile | Arg | Tyr |      |
|     |     | 335 |     |     |     |     | 340 |     |     |     |     | 345 |     |     |     |      |
| TCC | GTA | TTT | TCG | GGA | TTA | AGC | TTA | AAT | TTA | CCG | AAC | GAG | AAT | ATT | GGT | 1284 |
| Ser | Val | Phe | Ser | Gly | Leu | Ser | Leu | Asn | Leu | Pro | Asn | Glu | Asn | Ile | Gly |      |
|     | 350 |     |     |     |     | 355 |     |     |     |     | 360 |     |     |     |     |      |
| TCC | ACT | TTA | AAA | TTA | TCT | CAG | TTA | TTA | AGC | GAC | TGG | AGT | AAA | CCT | GAA | 1332 |
| Ser | Thr | Leu | Lys | Leu | Ser | Gln | Leu | Leu | Ser | Asp | Trp | Ser | Lys | Pro | Glu |      |
| 365 |     |     |     |     | 370 |     |     |     |     | 375 |     |     |     |     | 380 |      |
| ATC | ATC | GAA | GGC | GTA | GAA | TGT | AAC | CGT | TGT | GCC | CTC | ACA | GCA | GCG | CAC | 1380 |
| Ile | Ile | Glu | Gly | Val | Glu | Cys | Asn | Arg | Cys | Ala | Leu | Thr | Ala | Ala | His |      |
|     |     |     |     | 385 |     |     |     |     | 390 |     |     |     |     | 395 |     |      |
| TCT | CAT | TTA | TTT | GGT | CAG | TTG | AAA | GAA | TTT | GAA | AAA | AAA | CCT | GAG | GGT | 1428 |
| Ser | His | Leu | Phe | Gly | Gln | Leu | Lys | Glu | Phe | Glu | Lys | Lys | Pro | Glu | Gly |      |
|     |     |     | 400 |     |     |     |     | 405 |     |     |     |     | 410 |     |     |      |
| TCG | ATC | CCA | GAA | AAG | CCA | ATT | AAC | GCT | GTA | AAA | GAT | AGG | GTC | CAT | CAA | 1476 |
| Ser | Ile | Pro | Glu | Lys | Pro | Ile | Asn | Ala | Val | Lys | Asp | Arg | Val | His | Gln |      |
|     |     | 415 |     |     |     |     | 420 |     |     |     |     | 425 |     |     |     |      |
| ATC | GAA | GAA | GTT | CTT | GCC | AAA | CCA | GTT | ATT | GAC | GAT | GAA | GAT | TAT | AAG | 1524 |
| Ile | Glu | Glu | Val | Leu | Ala | Lys | Pro | Val | Ile | Asp | Asp | Glu | Asp | Tyr | Lys |      |
|     | 430 |     |     |     |     | 435 |     |     |     |     | 440 |     |     |     |     |      |
| AAG | TTG | CAT | ACA | GCA | AAT | ATG | GTA | CGT | AAA | TGC | TCT | AAA | TCT | AAG | CAG | 1572 |
| Lys | Leu | His | Thr | Ala | Asn | Met | Val | Arg | Lys | Cys | Ser | Lys | Ser | Lys | Gln |      |
| 445 |     |     |     |     | 450 |     |     |     |     | 455 |     |     |     |     | 460 |      |
| ATT | TTA | ATA | TCA | AGA | CCT | CCA | CCA | TTA | TTA | TCC | ATT | CAT | ATC | AAC | AGA | 1620 |
| Ile | Leu | Ile | Ser | Arg | Pro | Pro | Pro | Leu | Leu | Ser | Ile | His | Ile | Asn | Arg |      |
|     |     |     |     | 465 |     |     |     |     | 470 |     |     |     |     | 475 |     |      |
| TCC | GTA | TTT | GAT | CCA | AGA | ACG | TAC | ATG | ATT | AGA | AAA | AAT | AAC | TCG | AAA | 1668 |
| Ser | Val | Phe | Asp | Pro | Arg | Thr | Tyr | Met | Ile | Arg | Lys | Asn | Asn | Ser | Lys |      |
|     |     |     | 480 |     |     |     |     | 485 |     |     |     |     | 490 |     |     |      |
| GTA | TTG | TTT | AAG | TCA | AGG | TTG | AAT | CTT | GCC | CCA | TGG | TGT | TGT | GAT | ATT | 1716 |
| Val | Leu | Phe | Lys | Ser | Arg | Leu | Asn | Leu | Ala | Pro | Trp | Cys | Cys | Asp | Ile |      |
|     |     | 495 |     |     |     |     | 500 |     |     |     |     | 505 |     |     |     |      |
| AAT | GAA | ATC | AAT | TTG | GAT | GCT | CGT | TTG | CCA | ATG | TCA | AAA | AAG | GAA | AAA | 1764 |
| Asn | Glu | Ile | Asn | Leu | Asp | Ala | Arg | Leu | Pro | Met | Ser | Lys | Lys | Glu | Lys |      |
| 510 |     |     |     |     | 515 |     |     |     |     | 520 |     |     |     |     |     |      |
| GCT | GCG | CAA | CAA | GAT | TCA | AGT | GAA | GAT | GAA | AAC | ATT | GGC | GGT | GAA | TAC | 1812 |
| Ala | Ala | Gln | Gln | Asp | Ser | Ser | Glu | Asp | Glu | Asn | Ile | Gly | Gly | Glu | Tyr |      |
| 525 |     |     |     |     | 530 |     |     |     |     | 535 |     |     |     |     | 540 |      |
| TAT | ACG | AAA | TTA | CAT | GAA | CGC | TTC | GAG | CAG | GAA | TTT | GAA | GAC | AGC | GAG | 1860 |
| Tyr | Thr | Lys | Leu | His | Glu | Arg | Phe | Glu | Gln | Glu | Phe | Glu | Asp | Ser | Glu |      |
|     |     |     |     | 545 |     |     |     |     | 550 |     |     |     |     | 555 |     |      |
| GAA | GAA | AAA | GAA | TAC | GAT | GAC | GCA | GAG | GGG | AAC | TAT | GCG | TCT | CAT | TAC | 1908 |
| Glu | Glu | Lys | Glu | Tyr | Asp | Asp | Ala | Glu | Gly | Asn | Tyr | Ala | Ser | His | Tyr |      |
|     |     |     | 560 |     |     |     |     | 565 |     |     |     |     | 570 |     |     |      |
| AAT | CAT | ACC | AAG | GAT | ATC | AGT | AAC | TAT | GAT | CCC | CTA | AAC | GGT | GAA | GTC | 1956 |
| Asn | His | Thr | Lys | Asp | Ile | Ser | Asn | Tyr | Asp | Pro | Leu | Asn | Gly | Glu | Val |      |
|     |     | 575 |     |     |     |     | 580 |     |     |     |     | 585 |     |     |     |      |
| GAT | GGC | GTG | ACA | TCC | GAT | GAT | GAA | GAT | GAG | TAC | ATT | GAA | GAA | ACC | GAT | 2004 |
| Asp | Gly | Val | Thr | Ser | Asp | Asp | Glu | Asp | Glu | Tyr | Ile | Glu | Glu | Thr | Asp |      |
|     | 590 |     |     |     |     | 595 |     |     |     |     | 600 |     |     |     |     |      |
| GCT | TTA | GGG | AAT | ACA | ATC | AAA | AAA | AGG | ATC | ATA | GAA | CAT | TCT | GAT | GTT | 2052 |
| Ala | Leu | Gly | Asn | Thr | Ile | Lys | Lys | Arg | Ile | Ile | Glu | His | Ser | Asp | Val |      |
| 605 |     |     |     |     | 610 |     |     |     |     | 615 |     |     |     |     | 620 |      |
| GAA | AAC | GAG | AAT | GTA | AAA | GAT | AAT | GAA | GAA | CTG | CAA | GAA | ATC | GAC | AAT | 2100 |

| | | | | | | | | | | | | | | |
|---|---|---|---|---|---|---|---|---|---|---|---|---|---|---|
| Glu | Asn | Glu | Asn | Val 625 | Lys | Asp | Asn | Glu 630 | Leu | Gln | Glu | Ile | Asn 635 | |

| | | | | | | | | | | | | | | | |
|---|---|---|---|---|---|---|---|---|---|---|---|---|---|---|---|
| GTG | AGC | CTT | GAC | GAA | CCA | AAG | ATC | AAT | GTT | GAA | GAT | CAA | CTA | GAA | ACA |
| Val | Ser | Leu | Asp 640 | Glu | Pro | Lys | Ile | Asn 645 | Val | Glu | Asp | Gln | Leu 650 | Glu | Thr |

2148

| TCA | TCT | GAT | GAG | GAA | GAT | GTT | ATA | CCA | GCT | CCA | CCT | ATC | AAT | TAT | GCT |
|---|---|---|---|---|---|---|---|---|---|---|---|---|---|---|---|
| Ser | Ser | Asp 655 | Glu | Glu | Asp | Val | Ile 660 | Pro | Ala | Pro | Pro | Ile 665 | Asn | Tyr | Ala |

2196

| AGG | TCA | TTT | TCC | ACA | GTT | CCA | GCC | ACT | CCA | TTG | ACA | TAT | TCA | TTG | CGC |
|---|---|---|---|---|---|---|---|---|---|---|---|---|---|---|---|
| Arg | Ser 670 | Phe | Ser | Thr | Val | Pro 675 | Ala | Thr | Pro | Leu | Thr 680 | Tyr | Ser | Leu | Arg |

2244

| TCT | GTC | ATT | GTT | CAC | TAC | GGT | ACC | CAT | AAT | TAT | GGT | CAT | TAC | ATT | GCA |
|---|---|---|---|---|---|---|---|---|---|---|---|---|---|---|---|
| Ser 685 | Val | Ile | Val | His | Tyr 690 | Gly | Thr | His | Asn | Tyr 695 | Gly | His | Tyr | Ile | Ala 700 |

2292

| TTT | AGA | AAA | TAC | AGG | GGT | TGT | TGG | TGG | AGA | ATA | TCT | GAT | GAG | ACT | GTG |
|---|---|---|---|---|---|---|---|---|---|---|---|---|---|---|---|
| Phe | Arg | Lys | Tyr | Arg 705 | Gly | Cys | Trp | Trp | Arg 710 | Ile | Ser | Asp | Glu | Thr 715 | Val |

2340

| TAC | GTT | GTG | GAC | GAA | GCT | GAA | GTC | CTT | TCA | ACA | CCC | GGT | GTA | TTT | ATG |
|---|---|---|---|---|---|---|---|---|---|---|---|---|---|---|---|
| Tyr | Val | Val | Asp 720 | Glu | Ala | Glu | Val | Leu 725 | Ser | Thr | Pro | Gly | Val 730 | Phe | Met |

2388

| TTA | TTT | TAC | GAA | TAT | GAC | TTT | GAT | GAA | GAA | ACT | GGG | AAG | ATG | AAG | GAT |
|---|---|---|---|---|---|---|---|---|---|---|---|---|---|---|---|
| Leu | Phe | Tyr 735 | Glu | Tyr | Asp | Phe | Asp 740 | Glu | Glu | Thr | Gly | Lys 745 | Met | Lys | Asp |

2436

| GAT | TTG | GAA | GCT | ATT | CAG | AGT | AAT | AAT | GAA | GAA | GAT | GAT | GAA | AAA | GAG |
|---|---|---|---|---|---|---|---|---|---|---|---|---|---|---|---|
| Asp | Leu 750 | Glu | Ala | Ile | Gln | Ser 755 | Asn | Asn | Glu | Glu | Asp 760 | Asp | Glu | Lys | Glu |

2484

| CAG | GAG | CAA | AAA | GGA | GTC | CAG | GAG | CCA | AAG | GAA | AGC | CAA | GAG | CAA | GGA |
|---|---|---|---|---|---|---|---|---|---|---|---|---|---|---|---|
| Gln | Glu 765 | Gln | Lys | Gly | Val 770 | Gln | Glu | Pro | Lys | Glu 775 | Ser | Gln | Glu | Gln | Gly 780 |

2532

| GAA | GGT | GAA | GAG | CAA | GAG | GAA | GGT | CAA | GAG | CAG | ATG | AAG | TTC | GAG | AGA |
|---|---|---|---|---|---|---|---|---|---|---|---|---|---|---|---|
| Glu | Gly | Glu | Glu | Gln 785 | Glu | Glu | Gly | Gln | Glu 790 | Gln | Met | Lys | Phe | Glu 795 | Arg |

2580

| ACA | GAA | GAC | CAT | AGA | GAT | ATT | TCT | GGT | AAA | GAT | GTA | AAC | TAAGTTATAA | | |
|---|---|---|---|---|---|---|---|---|---|---|---|---|---|---|---|
| Thr | Glu | Asp | His 800 | Arg | Asp | Ile | Ser | Gly 805 | Lys | Asp | Val | Asn | | | |

2629

| | | | | |
|---|---|---|---|---|
| ATACGATATC | CGTAATTGTG | TAAATAACAA | TAACTATAAT | TAAATTGAAT AATTAAAAGT | 2689 |
| CTACGTTATT | CGTAAATCA | ATTGTTAGC | TAGTTACGAA | TGTCTAAAGT TTTTGTAGGA | 2749 |
| CAATTGCAAA | AATCACTTCC | ATTATTATAC | AAATCCTTCT | AAGCTTCATT TTTCTTACCA | 2809 |
| TTGTACTTCT | TCAACTTTTT | CTCTTCTCTT | CTCTCC | | 2845 |

(2) INFORMATION FOR SEQ ID NO:4:

(i) SEQUENCE CHARACTERISTICS:
        (A) LENGTH: 809 amino acids
        (B) TYPE: amino acid
        (D) TOPOLOGY: linear (ii) MOLECULE TYPE: protein (xi) SEQUENCE DESCRIPTION: SEQ ID NO:4:

| Met 1 | Asp | Leu | Phe | Ile 5 | Glu | Ser | Lys | Ile | Asn 10 | Ser | Leu | Leu | Gln | Phe 15 | Leu |
|---|---|---|---|---|---|---|---|---|---|---|---|---|---|---|---|
| Phe | Gly | Ser | Arg 20 | Gln | Asp | Phe | Leu | Arg 25 | Asn | Phe | Lys | Thr | Trp 30 | Ser | Asn |
| Asn | Asn | Asn 35 | Asn | Leu | Ser | Ile | Tyr 40 | Leu | Leu | Ile | Phe | Gly 45 | Ile | Val | Val |
| Phe | Phe 50 | Tyr | Lys | Lys | Pro | Asp 55 | His | Leu | Asn | Tyr | Ile 60 | Val | Glu | Ser | Val |
| Ser | Glu | Met | Thr | Thr | Asn | Phe | Arg | Asn | Asn | Asn | Ser | Leu | Ser | Arg | Trp |

|  65 | | | | | 70 | | | | | 75 | | | | 80 |
|---|---|---|---|---|---|---|---|---|---|---|---|---|---|---|
| Leu | Pro | Arg | Ser | Lys 85 | Phe | Thr | His | Leu | Asp 90 | Glu | Glu | Ile | Leu 95 | Lys | Arg |

Gly Gly Phe Ile Ala Gly Leu Val Asn Asp Gly Asn Thr Cys Phe Met
           100                 105                110

Asn Ser Val Leu Gln Ser Leu Ala Ser Ser Arg Glu Leu Met Glu Phe
       115                120                125

Leu Asp Asn Asn Val Ile Arg Thr Tyr Glu Glu Ile Glu Gln Asn Glu
130                 135                140

His Asn Glu Glu Gly Asn Gly Gln Glu Ser Ala Gln Asp Glu Ala Thr
145                 150              155              160

His Lys Lys Asn Thr Arg Lys Gly Gly Lys Val Tyr Gly Lys His Lys
               165              170              175

Lys Lys Leu Asn Arg Lys Ser Ser Lys Glu Asp Glu Glu Lys Ser
         180                185              190

Gln Glu Pro Asp Ile Thr Phe Ser Val Ala Leu Arg Asp Leu Leu Ser
       195                200              205

Ala Leu Asn Ala Lys Tyr Tyr Arg Asp Lys Pro Tyr Phe Lys Thr Asn
210                 215                220

Ser Leu Leu Lys Ala Met Ser Lys Ser Pro Arg Lys Asn Ile Leu Leu
225                 230              235              240

Gly Tyr Asp Gln Glu Asp Ala Gln Glu Phe Phe Gln Asn Ile Leu Ala
            245               250              255

Glu Leu Glu Ser Asn Val Lys Ser Leu Asn Thr Glu Lys Leu Asp Thr
         260                265              270

Thr Pro Val Ala Lys Ser Glu Leu Pro Asp Asp Ala Leu Val Gly Gln
       275                280              285

Leu Asn Leu Gly Glu Val Gly Thr Val Tyr Ile Pro Thr Glu Gln Ile
290                 295                300

Asp Pro Asn Ser Ile Leu His Asp Lys Ser Ile Gln Asn Phe Thr Pro
305                 310              315              320

Phe Lys Leu Met Thr Pro Leu Asp Gly Ile Thr Ala Glu Arg Ile Gly
            325               330              335

Cys Leu Gln Cys Gly Glu Asn Gly Gly Ile Arg Tyr Ser Val Phe Ser
         340                345              350

Gly Leu Ser Leu Asn Leu Pro Asn Glu Asn Ile Gly Ser Thr Leu Lys
       355                360              365

Leu Ser Gln Leu Leu Ser Asp Trp Ser Lys Pro Glu Ile Ile Glu Gly
     370                375              380

Val Glu Cys Asn Arg Cys Ala Leu Thr Ala Ala His Ser His Leu Phe
385                 390              395              400

Gly Gln Leu Lys Glu Phe Glu Lys Lys Pro Glu Gly Ser Ile Pro Glu
            405               410              415

Lys Pro Ile Asn Ala Val Lys Asp Arg Val His Gln Ile Glu Glu Val
         420                425              430

Leu Ala Lys Pro Val Ile Asp Asp Glu Asp Tyr Lys Lys Leu His Thr
       435                440              445

Ala Asn Met Val Arg Lys Cys Ser Lys Ser Lys Gln Ile Leu Ile Ser
450                 455              460

Arg Pro Pro Pro Leu Leu Ser Ile His Ile Asn Arg Ser Val Phe Asp
465                 470              475              480

Pro Arg Thr Tyr Met Ile Arg Lys Asn Asn Ser Lys Val Leu Phe Lys
            485               490              495

```
Ser  Arg  Leu  Asn  Leu  Ala  Pro  Trp  Cys  Cys  Asp  Ile  Asn  Glu  Ile  Asn
          500                           505                      510

Leu  Asp  Ala  Arg  Leu  Pro  Met  Ser  Lys  Lys  Glu  Lys  Ala  Ala  Gln  Gln
               515                      520                      525

Asp  Ser  Ser  Glu  Asp  Glu  Asn  Ile  Gly  Gly  Glu  Tyr  Tyr  Thr  Lys  Leu
          530                      535                      540

His  Glu  Arg  Phe  Glu  Gln  Glu  Phe  Glu  Asp  Ser  Glu  Glu  Glu  Lys  Glu
545                      550                      555                           560

Tyr  Asp  Asp  Ala  Glu  Gly  Asn  Tyr  Ala  Ser  His  Tyr  Asn  His  Thr  Lys
                    565                      570                      575

Asp  Ile  Ser  Asn  Tyr  Asp  Pro  Leu  Asn  Gly  Glu  Val  Asp  Gly  Val  Thr
               580                      585                      590

Ser  Asp  Asp  Glu  Asp  Glu  Tyr  Ile  Glu  Glu  Thr  Asp  Ala  Leu  Gly  Asn
          595                      600                      605

Thr  Ile  Lys  Lys  Arg  Ile  Ile  Glu  His  Ser  Asp  Val  Glu  Asn  Glu  Asn
     610                      615                      620

Val  Lys  Asp  Asn  Glu  Glu  Leu  Gln  Glu  Ile  Asp  Asn  Val  Ser  Leu  Asp
625                      630                      635                           640

Glu  Pro  Lys  Ile  Asn  Val  Glu  Asp  Gln  Leu  Glu  Thr  Ser  Ser  Asp  Glu
                    645                      650                      655

Glu  Asp  Val  Ile  Pro  Ala  Pro  Pro  Ile  Asn  Tyr  Ala  Arg  Ser  Phe  Ser
                    660                      665                      670

Thr  Val  Pro  Ala  Thr  Pro  Leu  Thr  Tyr  Ser  Leu  Arg  Ser  Val  Ile  Val
               675                      680                      685

His  Tyr  Gly  Thr  His  Asn  Tyr  Gly  His  Tyr  Ile  Ala  Phe  Arg  Lys  Tyr
     690                      695                      700

Arg  Gly  Cys  Trp  Trp  Arg  Ile  Ser  Asp  Glu  Thr  Val  Tyr  Val  Val  Asp
705                      710                      715                           720

Glu  Ala  Glu  Val  Leu  Ser  Thr  Pro  Gly  Val  Phe  Met  Leu  Phe  Tyr  Glu
                    725                      730                      735

Tyr  Asp  Phe  Asp  Glu  Glu  Thr  Gly  Lys  Met  Lys  Asp  Asp  Leu  Glu  Ala
               740                      745                      750

Ile  Gln  Ser  Asn  Asn  Glu  Glu  Asp  Asp  Glu  Lys  Glu  Gln  Glu  Gln  Lys
          755                      760                      765

Gly  Val  Gln  Glu  Pro  Lys  Glu  Ser  Gln  Glu  Gln  Gly  Glu  Gly  Glu  Glu
     770                      775                      780

Gln  Glu  Glu  Gly  Gln  Glu  Gln  Met  Lys  Phe  Glu  Arg  Thr  Glu  Asp  His
785                      790                      795                           800

Arg  Asp  Ile  Ser  Gly  Lys  Asp  Val  Asn
                    805
```

( 2 ) INFORMATION FOR SEQ ID NO:5:

( i ) SEQUENCE CHARACTERISTICS:
        ( A ) LENGTH: 6008 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 983..4774

( x i ) SEQUENCE DESCRIPTION: SEQ ID NO:5:

```
GCATGCTCCC AAGTGTCAGA ATTTATCAGA TGCTCAGGCT GCATTTTGG ACCGTGTTAT        60

TCGTGTAGAT CAAGCTGGCG AATTAGGTGC AGACTACATC TACGCTGGCC AGTACTTCGT      120

GTTGGCTCAT AGGTACCCTC ACTTGAAACC TGTGCTAAAG CACATATGGG ACCAGGAGAT      180
```

| | | | | | |
|---|---|---|---|---|---|
| ACATCATCAT | AATACTTTTA | ACAATTTGCA | ATTGAAAAGG | AGAGTCAGGC | CTTCCTTATT | 240
| AACGCCTTTG | TGGAAGGCAG | GAGCCTTTGC | AATGGGGGCT | GGTACCGCAT | TGATTTCTCC | 300
| AGAAGCAGCT | ATGGCTTGTA | CTGAAGCTGT | CGAGACAGTA | ATCGGAGGGC | ACTACAATGG | 360
| CCAATTGCGA | AACTTGGCCA | ATCAATTCAA | TTTAGAAAGA | ACAGATGGAA | CAAAGGGTCC | 420
| AAGTGAGGAA | ATCAAATCCT | TAACTTCTAC | TATCCAACAG | TTCAGGGATG | ACGAGCTAGA | 480
| GCATCTAGAC | ACCGCTATCA | AGCATGATTC | GTATATGGCA | GTTCCATATA | CAGTTATCAC | 540
| TGAAGGTATT | AAAACGATTT | GCAGAGTAGC | TATATGGAGT | GCCGAAAGAA | TTTAACCACC | 600
| AGAAAGTGGC | ATACATCAGT | CGCGTTATGC | CAGAAAAGGA | GAATTGAAAG | GAAAACGGTT | 660
| TGATAAATGT | CCTAATTAAA | CTATCATGTA | TAAAATTATG | TATCATCCTT | ACGCATTTTA | 720
| ACGCTATATG | ACCAATATGA | CAGGAATAGA | TACACTGTCT | ATAATTATGT | AAATGGGGTA | 780
| TGGGTTCATA | GTCTAAGGGT | GAGTACAAAC | TGGATCTTTA | ACAAGAGTAA | CAGTTAATTA | 840
| GAGCAAAACT | ATAGTACATA | TAGCTTGAAA | AAAACAAGCG | GCTTGCCATT | GGAAGAACAT | 900
| TGCATAAAAA | CGGGGCCACT | GCTAATAATA | AAGTGGTAAT | TAAAAGAAA | GCTTTTGTTC | 960
| AAGGTTAAGA | AGGTATAAGG | AA ATG CCG AAC GAA GAT AAT GAA CTT CAA AAA | | | 1012
| | | Met Pro Asn Glu Asp Asn Glu Leu Gln Lys | | |
| | | 1      5          10 | | |

```
GCA ATT GAG AAC CAT CAT AAT CAA CTA CTA AAC CAG GAT AAA GAA AAT        1060
Ala Ile Glu Asn His His Asn Gln Leu Leu Asn Gln Asp Lys Glu Asn
             15                  20                  25

GCT GAC AGA AAT GGG TCT GTT ATA GAA GAC CTC CCA TTA TAC GGG ACA        1108
Ala Asp Arg Asn Gly Ser Val Ile Glu Asp Leu Pro Leu Tyr Gly Thr
         30                  35                  40

AGT ATA AAC CAG CAG TCT ACC CCT GGA GAT GTT GAC GAT GGA AAA CAC        1156
Ser Ile Asn Gln Gln Ser Thr Pro Gly Asp Val Asp Asp Gly Lys His
             45                  50                  55

TTA CTG TAT CCA GAT ATT GCC ACC AAC CTA CCA CTG AAG ACT TCT GAC        1204
Leu Leu Tyr Pro Asp Ile Ala Thr Asn Leu Pro Leu Lys Thr Ser Asp
         60                  65                  70

AGA CTT TTG GAC GAT ATA CTT TGC GAT ACT ATT TTT CTC AAT TCT ACA        1252
Arg Leu Leu Asp Asp Ile Leu Cys Asp Thr Ile Phe Leu Asn Ser Thr
 75                  80                  85                  90

GAC CCG AAG GTC ATG CAA AAG GGC CTG CAA TCG AGG GGT ATT TTA AAA        1300
Asp Pro Lys Val Met Gln Lys Gly Leu Gln Ser Arg Gly Ile Leu Lys
             95                 100                 105

GAG TCT ATG CTT TCT TAC TCA ACT TTC AGA AGT AGT ATT CGC CCT AAC        1348
Glu Ser Met Leu Ser Tyr Ser Thr Phe Arg Ser Ser Ile Arg Pro Asn
         110                 115                 120

TGC TTG GGT TCA TTA ACT GAT CAA GTG GTT TTT CAA ACA AAA TCC GAG        1396
Cys Leu Gly Ser Leu Thr Asp Gln Val Val Phe Gln Thr Lys Ser Glu
             125                 130                 135

TAT GAT TCC ATT TCA TGC CCA AAA TAT AAT AAA ATA CAT GTA TTT CAG        1444
Tyr Asp Ser Ile Ser Cys Pro Lys Tyr Asn Lys Ile His Val Phe Gln
 140                 145                 150

GCG GTC ATC TTT AAT CCA TCA CTG GCA GAA CAG CAA ATT TCA ACT TTT        1492
Ala Val Ile Phe Asn Pro Ser Leu Ala Glu Gln Gln Ile Ser Thr Phe
155                 160                 165                 170

GAT GAT ATT GTT AAA ATT CCT ATT TAT CAT CTT AAG GTT AGC GTA AAA        1540
Asp Asp Ile Val Lys Ile Pro Ile Tyr His Leu Lys Val Ser Val Lys
             175                 180                 185

GTC CGC CAA GAA CTG GAG CGG TTG AAG AAG CAT GTC GGT GTT ACT CAA        1588
Val Arg Gln Glu Leu Glu Arg Leu Lys Lys His Val Gly Val Thr Gln
         190                 195                 200

TTC CAC TCA CTA GAT CAT TTG CAC GAA TAC GAT CGA GTA GAC CTT TCG        1636
```

-continued

| | | | | | | | | | | | | | | | |
|---|---|---|---|---|---|---|---|---|---|---|---|---|---|---|---|
| Phe | His | Ser | Leu | Asp | His | Leu | His | Glu | Tyr | Asp | Arg | Val | Asp | Leu | Ser |
| | | 205 | | | | 210 | | | | | 215 | | | | |

| ACT | TTT | GAT | TCT | TCC | GAT | CCT | AAT | TTG | TTG | GAT | TAC | GGT | ATT | TAC | GTT | 1684 |
|---|---|---|---|---|---|---|---|---|---|---|---|---|---|---|---|---|
| Thr | Phe | Asp | Ser | Ser | Asp | Pro | Asn | Leu | Leu | Asp | Tyr | Gly | Ile | Tyr | Val | |
| | 220 | | | | 225 | | | | | | 230 | | | | | |

| TCT | GAT | GAT | ACT | AAC | AAA | CTG | ATC | TTG | ATT | GAA | ATT | TTT | AAA | CCC | GAG | 1732 |
|---|---|---|---|---|---|---|---|---|---|---|---|---|---|---|---|---|
| Ser | Asp | Asp | Thr | Asn | Lys | Leu | Ile | Leu | Ile | Glu | Ile | Phe | Lys | Pro | Glu | |
| 235 | | | | | 240 | | | | | 245 | | | | | 250 | |

| TTT | AAT | TCA | CCT | GAA | GAG | CAT | GAG | AGT | TTT | ACT | GCC | GAC | GCA | ATT | AAG | 1780 |
|---|---|---|---|---|---|---|---|---|---|---|---|---|---|---|---|---|
| Phe | Asn | Ser | Pro | Glu | Glu | His | Glu | Ser | Phe | Thr | Ala | Asp | Ala | Ile | Lys | |
| | | | | | 255 | | | | | 260 | | | | | 265 | |

| AAG | AGA | TAC | AAT | GCT | ATG | TGT | GTA | AAA | AAT | GAA | TCA | CTA | GAT | AAA | AGC | 1828 |
|---|---|---|---|---|---|---|---|---|---|---|---|---|---|---|---|---|
| Lys | Arg | Tyr | Asn | Ala | Met | Cys | Val | Lys | Asn | Glu | Ser | Leu | Asp | Lys | Ser | |
| | | | 270 | | | | 275 | | | | | 280 | | | | |

| GAG | ACG | CCA | TCT | CAA | GTT | GAC | TGT | TTT | TAC | ACA | CTT | TTT | AAA | ATT | TTT | 1876 |
|---|---|---|---|---|---|---|---|---|---|---|---|---|---|---|---|---|
| Glu | Thr | Pro | Ser | Gln | Val | Asp | Cys | Phe | Tyr | Thr | Leu | Phe | Lys | Ile | Phe | |
| | | 285 | | | | | 290 | | | | | 295 | | | | |

| AAA | GGG | CCT | TTG | ACG | AGG | AAA | AGT | AAA | GCG | GAA | CCT | ACA | AAG | ACA | ATT | 1924 |
|---|---|---|---|---|---|---|---|---|---|---|---|---|---|---|---|---|
| Lys | Gly | Pro | Leu | Thr | Arg | Lys | Ser | Lys | Ala | Glu | Pro | Thr | Lys | Thr | Ile | |
| | 300 | | | | | 305 | | | | | 310 | | | | | |

| GAT | TCT | GGA | AAT | TTG | GCC | CTT | AAC | ACT | CAC | CTG | AAT | CCT | GAA | TGG | TTA | 1972 |
|---|---|---|---|---|---|---|---|---|---|---|---|---|---|---|---|---|
| Asp | Ser | Gly | Asn | Leu | Ala | Leu | Asn | Thr | His | Leu | Asn | Pro | Glu | Trp | Leu | |
| 315 | | | | | 320 | | | | | 325 | | | | | 330 | |

| ACG | TCC | AAG | TAT | GGA | TTT | CAA | GCA | AGC | TCA | GAA | ATC | GAT | GAG | GAA | ACT | 2020 |
|---|---|---|---|---|---|---|---|---|---|---|---|---|---|---|---|---|
| Thr | Ser | Lys | Tyr | Gly | Phe | Gln | Ala | Ser | Ser | Glu | Ile | Asp | Glu | Glu | Thr | |
| | | | | 335 | | | | | 340 | | | | | 345 | | |

| AAT | GAG | ATA | TTT | ACT | GAA | TAC | GTC | CCT | CCA | GAT | ATG | GTG | GAC | TAT | GTA | 2068 |
|---|---|---|---|---|---|---|---|---|---|---|---|---|---|---|---|---|
| Asn | Glu | Ile | Phe | Thr | Glu | Tyr | Val | Pro | Pro | Asp | Met | Val | Asp | Tyr | Val | |
| | | | 350 | | | | | 355 | | | | | 360 | | | |

| AAC | GAT | TTG | GAG | ACA | AGA | AAA | ATT | CGA | GAA | TCG | TTT | GTG | AGG | AAG | TGT | 2116 |
|---|---|---|---|---|---|---|---|---|---|---|---|---|---|---|---|---|
| Asn | Asp | Leu | Glu | Thr | Arg | Lys | Ile | Arg | Glu | Ser | Phe | Val | Arg | Lys | Cys | |
| | | 365 | | | | | 370 | | | | | 375 | | | | |

| TTA | CAA | CTG | ATA | TTT | TGG | GGT | CAA | CTA | TCT | ACC | TCA | TTA | CTG | GCA | CCT | 2164 |
|---|---|---|---|---|---|---|---|---|---|---|---|---|---|---|---|---|
| Leu | Gln | Leu | Ile | Phe | Trp | Gly | Gln | Leu | Ser | Thr | Ser | Leu | Leu | Ala | Pro | |
| 380 | | | | | 385 | | | | | 390 | | | | | | |

| AAT | TCT | CCC | TTG | AAA | AAT | ACG | AAA | AGC | GTA | AAG | GGA | ATG | TCT | TCA | TTA | 2212 |
|---|---|---|---|---|---|---|---|---|---|---|---|---|---|---|---|---|
| Asn | Ser | Pro | Leu | Lys | Asn | Thr | Lys | Ser | Val | Lys | Gly | Met | Ser | Ser | Leu | |
| 395 | | | | | 400 | | | | | 405 | | | | | 410 | |

| CAA | ACT | TCT | TTC | TCA | ACA | CTA | CCT | TGG | TTC | CAT | TTA | TTG | GGA | GAA | TCC | 2260 |
|---|---|---|---|---|---|---|---|---|---|---|---|---|---|---|---|---|
| Gln | Thr | Ser | Phe | Ser | Thr | Leu | Pro | Trp | Phe | His | Leu | Leu | Gly | Glu | Ser | |
| | | | | 415 | | | | | 420 | | | | | 425 | | |

| AGA | GCA | AGG | ATT | CTA | TTA | AAT | TCC | AAT | GAG | CAA | ACT | CAT | TCT | CCT | TTG | 2308 |
|---|---|---|---|---|---|---|---|---|---|---|---|---|---|---|---|---|
| Arg | Ala | Arg | Ile | Leu | Leu | Asn | Ser | Asn | Glu | Gln | Thr | His | Ser | Pro | Leu | |
| | | | 430 | | | | | 435 | | | | | 440 | | | |

| GAC | GCA | GAA | CCT | CAT | TTT | ATT | AAT | CTT | TCC | GTT | TCG | CAT | TAT | TAT | ACC | 2356 |
|---|---|---|---|---|---|---|---|---|---|---|---|---|---|---|---|---|
| Asp | Ala | Glu | Pro | His | Phe | Ile | Asn | Leu | Ser | Val | Ser | His | Tyr | Tyr | Thr | |
| | | 445 | | | | | 450 | | | | | 455 | | | | |

| GAT | AGA | GAT | ATA | ATC | AGA | AAC | TAC | GAA | TCT | TTG | TCT | TCT | TTG | GAT | CCT | 2404 |
|---|---|---|---|---|---|---|---|---|---|---|---|---|---|---|---|---|
| Asp | Arg | Asp | Ile | Ile | Arg | Asn | Tyr | Glu | Ser | Leu | Ser | Ser | Leu | Asp | Pro | |
| | 460 | | | | | 465 | | | | | 470 | | | | | |

| GAA | AAT | ATT | GGG | CTG | TAT | TTT | GAC | GCA | CTG | ACA | TAC | ATT | GCA | AAT | AGG | 2452 |
|---|---|---|---|---|---|---|---|---|---|---|---|---|---|---|---|---|
| Glu | Asn | Ile | Gly | Leu | Tyr | Phe | Asp | Ala | Leu | Thr | Tyr | Ile | Ala | Asn | Arg | |
| 475 | | | | | 480 | | | | | 485 | | | | | 490 | |

| AAG | GGG | GCA | TAT | CAA | TTG | ATT | GCT | TAC | TGT | GGA | AAA | CAG | GAC | ATT | ATA | 2500 |
|---|---|---|---|---|---|---|---|---|---|---|---|---|---|---|---|---|
| Lys | Gly | Ala | Tyr | Gln | Leu | Ile | Ala | Tyr | Cys | Gly | Lys | Gln | Asp | Ile | Ile | |
| | | | | 495 | | | | | 500 | | | | | 505 | | |

| GGC | CAA | GAA | GCT | CTA | GAA | AAT | GCT | TTG | TTA | ATG | TTT | AAA | ATT | AAC | CCT | 2548 |
|---|---|---|---|---|---|---|---|---|---|---|---|---|---|---|---|---|
| Gly | Gln | Glu | Ala | Leu | Glu | Asn | Ala | Leu | Leu | Met | Phe | Lys | Ile | Asn | Pro | |
| | | | 510 | | | | | 515 | | | | | 520 | | | |

| AAA | GAG | TGT | AAC | ATC | TCC | GAA | TTA | AAT | GAG | GCG | ACT | TTG | CTA | TCT | ATT | 2596 |

| | | | | | | | | | | | | | | | | |
|---|---|---|---|---|---|---|---|---|---|---|---|---|---|---|---|---|
| Lys | Glu | Cys | Asn | Ile | Ser | Glu | Leu | Asn | Glu | Ala | Thr | Leu | Leu | Ser | Ile | |
| | | 525 | | | | 530 | | | | | | 535 | | | | |
| TAC | AAA | TAT | GAA | ACA | TCA | AAT | AAG | AGC | CAA | GTA | ACC | TCT | AAT | CAC | CTA | 2644 |
| Tyr | Lys | Tyr | Glu | Thr | Ser | Asn | Lys | Ser | Gln | Val | Thr | Ser | Asn | His | Leu | |
| | 540 | | | | | 545 | | | | | 550 | | | | | |
| ACA | AAT | TTG | AAA | AAT | GCT | CTA | AGA | TTG | TTG | GCC | AAA | TAT | ACC | AAA | TCT | 2692 |
| Thr | Asn | Leu | Lys | Asn | Ala | Leu | Arg | Leu | Leu | Ala | Lys | Tyr | Thr | Lys | Ser | |
| 555 | | | | | 560 | | | | | 565 | | | | | 570 | |
| GAC | AAA | CTA | AAA | TTT | TAC | GTC | GAT | CAT | GAG | CCC | TAC | AGA | GCT | TTA | TCC | 2740 |
| Asp | Lys | Leu | Lys | Phe | Tyr | Val | Asp | His | Glu | Pro | Tyr | Arg | Ala | Leu | Ser | |
| | | | | 575 | | | | | 580 | | | | | 585 | | |
| CAG | GCA | TAC | GAC | ACA | CTT | TCA | ATT | GAC | GAG | TCT | GTT | GAT | GAA | GAC | ATT | 2788 |
| Gln | Ala | Tyr | Asp | Thr | Leu | Ser | Ile | Asp | Glu | Ser | Val | Asp | Glu | Asp | Ile | |
| | | | 590 | | | | | 595 | | | | | 600 | | | |
| ATA | AAA | ACT | GCA | TAT | TCG | GTC | AAG | ATT | AAC | GAC | TCT | CCC | GGA | TTA | AAG | 2836 |
| Ile | Lys | Thr | Ala | Tyr | Ser | Val | Lys | Ile | Asn | Asp | Ser | Pro | Gly | Leu | Lys | |
| | | 605 | | | | | 610 | | | | | 615 | | | | |
| TTG | GAT | TGT | GAT | AGA | GCA | CTT | TAC | ACC | ATT | GCT | ATC | AGT | AAA | AGA | AGC | 2884 |
| Leu | Asp | Cys | Asp | Arg | Ala | Leu | Tyr | Thr | Ile | Ala | Ile | Ser | Lys | Arg | Ser | |
| 620 | | | | | 625 | | | | | 630 | | | | | | |
| CTT | GAT | TTG | TTC | AAT | TTT | TTA | ACA | GAG | GAA | TGC | CCA | CAG | TTT | TCC | AAC | 2932 |
| Leu | Asp | Leu | Phe | Asn | Phe | Leu | Thr | Glu | Glu | Cys | Pro | Gln | Phe | Ser | Asn | |
| 635 | | | | | 640 | | | | | 645 | | | | | 650 | |
| TAT | TAT | GGT | CCA | GAG | AAG | CTT | CTT | CAA | GTG | AAT | GAA | AAT | GCC | TCT | GAC | 2980 |
| Tyr | Tyr | Gly | Pro | Glu | Lys | Leu | Leu | Gln | Val | Asn | Glu | Asn | Ala | Ser | Asp | |
| | | | | 655 | | | | | 660 | | | | | 665 | | |
| GAA | ACC | ATT | TTG | AAA | ATC | TTT | AAA | CAA | AAG | TGG | TTT | GAT | GAA | AAC | GTT | 3028 |
| Glu | Thr | Ile | Leu | Lys | Ile | Phe | Lys | Gln | Lys | Trp | Phe | Asp | Glu | Asn | Val | |
| | | | 670 | | | | | 675 | | | | | 680 | | | |
| TAT | GAG | CCT | GAC | CAA | TTT | CTT | ATT | TTG | AGG | GCA | GCA | TTG | ACC | AAA | ATC | 3076 |
| Tyr | Glu | Pro | Asp | Gln | Phe | Leu | Ile | Leu | Arg | Ala | Ala | Leu | Thr | Lys | Ile | |
| | | | 685 | | | | | 690 | | | | | 695 | | | |
| AGT | ATA | GAA | AGA | AAT | TCA | ACT | TTA | ATC | ACC | AAC | TTC | TTA | CTA | ACT | GGT | 3124 |
| Ser | Ile | Glu | Arg | Asn | Ser | Thr | Leu | Ile | Thr | Asn | Phe | Leu | Leu | Thr | Gly | |
| | 700 | | | | | 705 | | | | | 710 | | | | | |
| ACG | ATA | GAT | CCA | AAT | TCC | TTG | CCG | CCA | GAA | AAT | TGG | CCA | ACT | GGC | ATT | 3172 |
| Thr | Ile | Asp | Pro | Asn | Ser | Leu | Pro | Pro | Glu | Asn | Trp | Pro | Thr | Gly | Ile | |
| 715 | | | | | 720 | | | | | 725 | | | | | 730 | |
| AAT | AAT | ATC | GGG | AAC | ACC | TGT | TAC | CTA | AAT | TCT | TTA | TTA | CAA | TAT | TAC | 3220 |
| Asn | Asn | Ile | Gly | Asn | Thr | Cys | Tyr | Leu | Asn | Ser | Leu | Leu | Gln | Tyr | Tyr | |
| | | | | 735 | | | | | 740 | | | | | 745 | | |
| TTT | TCC | ATT | GCG | CCA | CTA | AGA | AGA | TAT | GTA | TTG | GAA | TAT | CAA | AAA | ACG | 3268 |
| Phe | Ser | Ile | Ala | Pro | Leu | Arg | Arg | Tyr | Val | Leu | Glu | Tyr | Gln | Lys | Thr | |
| | | | 750 | | | | | 755 | | | | | 760 | | | |
| GTA | GAA | AAT | TTC | AAT | GAC | CAC | CTC | TCT | AAT | AGT | GGG | CAT | ATT | AGA | AGA | 3316 |
| Val | Glu | Asn | Phe | Asn | Asp | His | Leu | Ser | Asn | Ser | Gly | His | Ile | Arg | Arg | |
| | 765 | | | | | 770 | | | | | 775 | | | | | |
| ATT | GGT | GGA | AGA | GAA | ATT | AGT | AGA | GGC | GAA | GTG | GAA | AGA | TCT | ATT | CAA | 3364 |
| Ile | Gly | Gly | Arg | Glu | Ile | Ser | Arg | Gly | Glu | Val | Glu | Arg | Ser | Ile | Gln | |
| 780 | | | | | 785 | | | | | 790 | | | | | | |
| TTC | ATA | TAC | CAA | CTT | CGC | AAC | CTT | TTC | TAT | GCG | ATG | GTT | CAT | ACA | AGA | 3412 |
| Phe | Ile | Tyr | Gln | Leu | Arg | Asn | Leu | Phe | Tyr | Ala | Met | Val | His | Thr | Arg | |
| 795 | | | | | 800 | | | | | 805 | | | | | 810 | |
| GAA | AGA | TGT | GTA | ACA | CCC | TCA | AAA | GAG | CTA | GCA | TAT | TTG | GCA | TTT | GCT | 3460 |
| Glu | Arg | Cys | Val | Thr | Pro | Ser | Lys | Glu | Leu | Ala | Tyr | Leu | Ala | Phe | Ala | |
| | | | | 815 | | | | | 820 | | | | | 825 | | |
| CCA | AGT | AAT | GTT | GAA | GTA | GAA | TTT | GAA | GTG | GAA | GGC | AAT | AAA | GTA | GTT | 3508 |
| Pro | Ser | Asn | Val | Glu | Val | Glu | Phe | Glu | Val | Glu | Gly | Asn | Lys | Val | Val | |
| | | | 830 | | | | | 835 | | | | | 840 | | | |
| GAT | CAA | ACA | GGA | GTT | CTT | TCG | GAT | TCA | AAG | AAG | GAA | ACA | ACG | GAT | GAC | 3556 |

```
Asp Gln Thr Gly Val Leu Ser Asp Ser Lys Lys Glu Thr Thr Asp Asp
    845             850             855

GCA TTT ACT ACA AAA ATA AAG GAT ACA AGC CTG ATT GAT TTA GAA ATG    3604
Ala Phe Thr Thr Lys Ile Lys Asp Thr Ser Leu Ile Asp Leu Glu Met
    860             865             870

GAA GAT GGC CTT AAT GGC GAT GTT GGT ACA GAT GCG AAC AGA AAA AAA    3652
Glu Asp Gly Leu Asn Gly Asp Val Gly Thr Asp Ala Asn Arg Lys Lys
875             880             885             890

AAT GAA TCG AAT GAT GCT GAA GTA AGT GAG AAC GAA GAT ACA ACA GGA    3700
Asn Glu Ser Asn Asp Ala Glu Val Ser Glu Asn Glu Asp Thr Thr Gly
                895             900             905

TTA ACT TCA CCT ACG CGT GTG GCA AAA ATC AGT TCT GAT CAA TTA GAA    3748
Leu Thr Ser Pro Thr Arg Val Ala Lys Ile Ser Ser Asp Gln Leu Glu
            910             915             920

AAT GCT TTG GAA ATG GGT AGG CAA CAA GAT GTT ACT GAA TGC ATA GGA    3796
Asn Ala Leu Glu Met Gly Arg Gln Gln Asp Val Thr Glu Cys Ile Gly
        925             930             935

AAC GTG TTA TTT CAG ATA GAA AGC GGT TCA GAG CCT ATC CGA TAT GAT    3844
Asn Val Leu Phe Gln Ile Glu Ser Gly Ser Glu Pro Ile Arg Tyr Asp
    940             945             950

GAA GAC AAC GAG CAA TAT GAC TTG GTT AAG CAA CTA TTT TAT GGT ACT    3892
Glu Asp Asn Glu Gln Tyr Asp Leu Val Lys Gln Leu Phe Tyr Gly Thr
955             960             965             970

ACT AAA CAA AGT ATT GTT CCT TTG TCC GCA ACA AAT AAA GTC CGT ACG    3940
Thr Lys Gln Ser Ile Val Pro Leu Ser Ala Thr Asn Lys Val Arg Thr
                975             980             985

AAA GTT GAA AGA TTC CTA TCG TTA CTG ATA AAT ATT GGC GAT CAT CCT    3988
Lys Val Glu Arg Phe Leu Ser Leu Leu Ile Asn Ile Gly Asp His Pro
            990             995             1000

AAA GAT ATT TAT GAT GCG TTT GAT TCT TAT TTT AAA GAC GAA TAT CTG    4036
Lys Asp Ile Tyr Asp Ala Phe Asp Ser Tyr Phe Lys Asp Glu Tyr Leu
        1005            1010            1015

ACA ATG GAA GAG TAT GGT GAT GTT ATA CGT ACC GTT GCT GTT ACA ACT    4084
Thr Met Glu Glu Tyr Gly Asp Val Ile Arg Thr Val Ala Val Thr Thr
    1020            1025            1030

TTT CCT ACT ATT TTG CAG GTA CAA ATC CAA AGA GTT TAT TAC GAT CGT    4132
Phe Pro Thr Ile Leu Gln Val Gln Ile Gln Arg Val Tyr Tyr Asp Arg
1035            1040            1045            1050

GAA AGA TTA ATG CCG TTT AAA TCC ATT GAG CCC TTA CCA TTC AAA GAA    4180
Glu Arg Leu Met Pro Phe Lys Ser Ile Glu Pro Leu Pro Phe Lys Glu
                1055            1060            1065

GTT ATT TAC ATG GAC AGA TAC GCG GAT ACA GAG AAC CCT TTA TTG TTG    4228
Val Ile Tyr Met Asp Arg Tyr Ala Asp Thr Glu Asn Pro Leu Leu Leu
            1070            1075            1080

GCA AAA AAG AAA GAA ACA GAA GAA ATG AAG CAA AAG TTG AAG GTA ATG    4276
Ala Lys Lys Lys Glu Thr Glu Glu Met Lys Gln Lys Leu Lys Val Met
        1085            1090            1095

AAA AAT AGA CAA AGA GAG CTT TTG AGT CGT GAT GAT TCA GGG CTT ACA    4324
Lys Asn Arg Gln Arg Glu Leu Leu Ser Arg Asp Asp Ser Gly Leu Thr
    1100            1105            1110

AGG AAG GAT GCA TTT TTG GAG AGT ATC AAG CTA TTG GAA TCG GAT ACC    4372
Arg Lys Asp Ala Phe Leu Glu Ser Ile Lys Leu Leu Glu Ser Asp Thr
1115            1120            1125            1130

ATA AAG AAA ACT CCT TTA AAA ATT GAG GCT GCT AAT GAT GTG ATA AAG    4420
Ile Lys Lys Thr Pro Leu Lys Ile Glu Ala Ala Asn Asp Val Ile Lys
                1135            1140            1145

ACG CTG AGA AAC AAC GTT CAA AAT ATC GAT AAT GAA TTG ATG AAA TTA    4468
Thr Leu Arg Asn Asn Val Gln Asn Ile Asp Asn Glu Leu Met Lys Leu
            1150            1155            1160

TAC AAT GAT ATC AAC AGT TTG GAA GAG AAA ATA AGC CAT CAA TTT GAC    4516
```

```
Tyr Asn Asp Ile Asn Ser Leu Glu Glu Lys Ile Ser His Gln Phe Asp
    1165                1170                1175

GAT TTC AAG GAA TAT GGT TAC TCA CTG TTT TCG GTT TTT ATT CAT CGC        4564
Asp Phe Lys Glu Tyr Gly Tyr Ser Leu Phe Ser Val Phe Ile His Arg
    1180                1185                1190

GGC GAG GCC AGT TAT GGT CAC TAT TGG ATA TAT ATC AAG GAC AGA AAT        4612
Gly Glu Ala Ser Tyr Gly His Tyr Trp Ile Tyr Ile Lys Asp Arg Asn
1195                1200                1205                1210

CGC AAT GGA ATT TGG AGG AAG TAC AAT GAT GAA ACC ATC AGC GAG GTC        4660
Arg Asn Gly Ile Trp Arg Lys Tyr Asn Asp Glu Thr Ile Ser Glu Val
                1215                1220                1225

CAG GAA GAG GAG GTC TTC AAT TTC AAT GAG GGT AAC ACT GCA ACT CCA        4708
Gln Glu Glu Glu Val Phe Asn Phe Asn Glu Gly Asn Thr Ala Thr Pro
            1230                1235                1240

TAT TTC CTA GTA TAT GTC AAA CAA GGA CAA GAA GGT GAT ATT GAG CCA        4756
Tyr Phe Leu Val Tyr Val Lys Gln Gly Gln Glu Gly Asp Ile Glu Pro
        1245                1250                1255

TTG AAA AGA ATT CTA AAG TAGTCTTAGT CAATGAAGAG TTTATGTAAA               4804
Leu Lys Arg Ile Leu Lys
    1260

ATGTCACTAT TGCCATAAGT ACCATTATTA TGTAAAAAGC TTTGCCATAT TCAATGTTAC      4864

GGGTGACTAT CTGCTACGTA AAGAAAAACG AAAAAACAAA AAAAAAAGA ACAAGCTCAT       4924

AGAAGTGAAT ACGAAAGCTG AAGAAAGTCG TTAAGTAGAT AGGTTGCGTA AACTAGGTGC      4984

GTCCAATCAA AGTAATCCAA TTAGATATAC TGGACTATAA TTAAGATGTC ATCTGAAAGC      5044

CCACAGGATC AACCACAGAA GGAGCAAATC AGCAATAACG TCGGCGTTAC CACCAATAGT      5104

ACAAGCAATG AGGAAACAAG CCGCTCTCAA GATGATAATG TCAAGGAAGT CAATGGAAAT      5164

GATGATACTA AGAAGAGGA ACAAGAAGAA GACGCAGAAC TAGATGATTT ATTTGGAGAT       5224

GACAATGATG ACGATGATGA TGATGATGTT AAAAAATCGG AGACTGAAAA AAGTGATAGT      5284

GATAGTGATG AAGACGACGA GGGAGAGAAT ATCAACCATA GAAGTCGTCA TAGAGAAAGT      5344

CTCGGGTTAG ATGATGATGA AGCAGAGGAG CAAGCCATGT ACACCCGAAA ATTTTATGGT     5404

GAGGATGCTA ATAACTTTTC TGATCTTGAT GAGACTACTC ACACTTTTAA AGAGGAAAAT    5464

GTAGAGCTTG TCAGACATAT TATTCCAAGT AAAGCTAATG TGAATGAAAC GGCGTCTCAC    5524

AACGAAATTT TCTATGCTAG AATTCCCAAC TTTTTAACTA TCGATCCAAT TCCTTTCGAC    5584

CCTCCAAGTT TTGAGGCCAA AGTAAACGAA AGGGCAAGCA ATTCAGCTTC TAGGGAGGAT    5644

CAACTGGACG ACCGCCTGAT TGATGAAAAC ACTGTTAGAT GGAGATACTC TCGTGACAAA    5704

GACCAACATG TCTTTAAAGA ATCAAATACA CAAATAGTGC AGTGGTCAGA CGGTACATAT    5764

TCGCTAAAAG TTGGTGAAGA GTGTACAGAT ATATTGGTCA ACGATACGAG CAACACTTTT    5824

TTGACAGTAT CGCATGACCA ACAAGAGTTG ATCCAGTGTT ACGAAGGGGG TGAAATAAAA    5884

AAGACGTTGA TGTTTATTCC AACTTCGACG AATTCAAAAA TACATCAAAA ACTAAGTAAA    5944

GCTGTTATAA GAAGGAACCA AAGACAAAGC AAGGGTCCTG GAAATACATT GTAAGTATGG    6004

ATCC                                                                   6008
```

( 2 ) INFORMATION FOR SEQ ID NO:6:

( i ) SEQUENCE CHARACTERISTICS:
        ( A ) LENGTH: 1264 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

-continued

```
Met Pro Asn Glu Asp Asn Glu Leu Gln Lys Ala Ile Glu Asn His His
 1               5                  10                      15

Asn Gln Leu Leu Asn Gln Asp Lys Glu Asn Ala Asp Arg Asn Gly Ser
            20                  25                  30

Val Ile Glu Asp Leu Pro Leu Tyr Gly Thr Ser Ile Asn Gln Gln Ser
            35                  40                  45

Thr Pro Gly Asp Val Asp Asp Gly Lys His Leu Leu Tyr Pro Asp Ile
     50                  55                      60

Ala Thr Asn Leu Pro Leu Lys Thr Ser Asp Arg Leu Leu Asp Asp Ile
 65              70                  75                      80

Leu Cys Asp Thr Ile Phe Leu Asn Ser Thr Asp Pro Lys Val Met Gln
                 85                  90                      95

Lys Gly Leu Gln Ser Arg Gly Ile Leu Lys Glu Ser Met Leu Ser Tyr
            100                 105                 110

Ser Thr Phe Arg Ser Ser Ile Arg Pro Asn Cys Leu Gly Ser Leu Thr
            115                 120                 125

Asp Gln Val Val Phe Gln Thr Lys Ser Glu Tyr Asp Ser Ile Ser Cys
    130                 135                 140

Pro Lys Tyr Asn Lys Ile His Val Phe Gln Ala Val Ile Phe Asn Pro
145                 150                 155                 160

Ser Leu Ala Glu Gln Gln Ile Ser Thr Phe Asp Asp Ile Val Lys Ile
                165                 170                 175

Pro Ile Tyr His Leu Lys Val Ser Val Lys Val Arg Gln Glu Leu Glu
            180                 185                 190

Arg Leu Lys Lys His Val Gly Val Thr Gln Phe His Ser Leu Asp His
            195                 200                 205

Leu His Glu Tyr Asp Arg Val Asp Leu Ser Thr Phe Asp Ser Ser Asp
    210                 215                 220

Pro Asn Leu Leu Asp Tyr Gly Ile Tyr Val Ser Asp Asp Thr Asn Lys
225                 230                 235                 240

Leu Ile Leu Ile Glu Ile Phe Lys Pro Glu Phe Asn Ser Pro Glu Glu
                245                 250                 255

His Glu Ser Phe Thr Ala Asp Ala Ile Lys Lys Arg Tyr Asn Ala Met
            260                 265                 270

Cys Val Lys Asn Glu Ser Leu Asp Lys Ser Glu Thr Pro Ser Gln Val
        275                 280                 285

Asp Cys Phe Tyr Thr Leu Phe Lys Ile Phe Lys Gly Pro Leu Thr Arg
    290                 295                 300

Lys Ser Lys Ala Glu Pro Thr Lys Thr Ile Asp Ser Gly Asn Leu Ala
305                 310                 315                 320

Leu Asn Thr His Leu Asn Pro Glu Trp Leu Thr Ser Lys Tyr Gly Phe
                325                 330                 335

Gln Ala Ser Ser Glu Ile Asp Glu Glu Thr Asn Glu Ile Phe Thr Glu
            340                 345                 350

Tyr Val Pro Pro Asp Met Val Asp Tyr Val Asn Asp Leu Glu Thr Arg
            355                 360                 365

Lys Ile Arg Glu Ser Phe Val Arg Lys Cys Leu Gln Leu Ile Phe Trp
    370                 375                 380

Gly Gln Leu Ser Thr Ser Leu Leu Ala Pro Asn Ser Pro Leu Lys Asn
385                 390                 395                 400

Thr Lys Ser Val Lys Gly Met Ser Ser Leu Gln Thr Ser Phe Ser Thr
                405                 410                 415

Leu Pro Trp Phe His Leu Leu Gly Glu Ser Arg Ala Arg Ile Leu Leu
```

|  |  |  | 420 |  |  |  | 425 |  |  |  | 430 |  |  |
|--|--|--|--|--|--|--|--|--|--|--|--|--|--|

Asn Ser Asn Glu Gln Thr His Ser Pro Leu Asp Ala Glu Pro His Phe
        435             440             445

Ile Asn Leu Ser Val Ser His Tyr Tyr Thr Asp Arg Asp Ile Ile Arg
    450             455             460

Asn Tyr Glu Ser Leu Ser Ser Leu Asp Pro Glu Asn Ile Gly Leu Tyr
465             470             475                         480

Phe Asp Ala Leu Thr Tyr Ile Ala Asn Arg Lys Gly Ala Tyr Gln Leu
                485             490                     495

Ile Ala Tyr Cys Gly Lys Gln Asp Ile Ile Gly Gln Glu Ala Leu Glu
            500             505                     510

Asn Ala Leu Leu Met Phe Lys Ile Asn Pro Lys Glu Cys Asn Ile Ser
        515             520             525

Glu Leu Asn Glu Ala Thr Leu Leu Ser Ile Tyr Lys Tyr Glu Thr Ser
    530             535             540

Asn Lys Ser Gln Val Thr Ser Asn His Leu Thr Asn Leu Lys Asn Ala
545             550             555                         560

Leu Arg Leu Leu Ala Lys Tyr Thr Lys Ser Asp Lys Leu Lys Phe Tyr
                565             570                     575

Val Asp His Glu Pro Tyr Arg Ala Leu Ser Gln Ala Tyr Asp Thr Leu
            580             585                     590

Ser Ile Asp Glu Ser Val Asp Glu Asp Ile Ile Lys Thr Ala Tyr Ser
        595             600             605

Val Lys Ile Asn Asp Ser Pro Gly Leu Lys Leu Asp Cys Asp Arg Ala
    610             615             620

Leu Tyr Thr Ile Ala Ile Ser Lys Arg Ser Leu Asp Leu Phe Asn Phe
625             630             635                         640

Leu Thr Glu Glu Cys Pro Gln Phe Ser Asn Tyr Tyr Gly Pro Glu Lys
                645             650                     655

Leu Leu Gln Val Asn Glu Asn Ala Ser Asp Glu Thr Ile Leu Lys Ile
            660             665                     670

Phe Lys Gln Lys Trp Phe Asp Glu Asn Val Tyr Glu Pro Asp Gln Phe
        675             680             685

Leu Ile Leu Arg Ala Ala Leu Thr Lys Ile Ser Ile Glu Arg Asn Ser
690             695             700

Thr Leu Ile Thr Asn Phe Leu Leu Thr Gly Thr Ile Asp Pro Asn Ser
705             710             715                         720

Leu Pro Pro Glu Asn Trp Pro Thr Gly Ile Asn Asn Ile Gly Asn Thr
                725             730                     735

Cys Tyr Leu Asn Ser Leu Leu Gln Tyr Tyr Phe Ser Ile Ala Pro Leu
            740             745                     750

Arg Arg Tyr Val Leu Glu Tyr Gln Lys Thr Val Glu Asn Phe Asn Asp
        755             760             765

His Leu Ser Asn Ser Gly His Ile Arg Arg Ile Gly Gly Arg Glu Ile
770             775             780

Ser Arg Gly Glu Val Glu Arg Ser Ile Gln Phe Ile Tyr Gln Leu Arg
785             790             795                         800

Asn Leu Phe Tyr Ala Met Val His Thr Arg Glu Arg Cys Val Thr Pro
                805             810                     815

Ser Lys Glu Leu Ala Tyr Leu Ala Phe Ala Pro Ser Asn Val Glu Val
            820             825                     830

Glu Phe Glu Val Glu Gly Asn Lys Val Val Asp Gln Thr Gly Val Leu
        835             840             845

```
Ser  Asp  Ser  Lys  Lys  Glu  Thr  Thr  Asp  Asp  Ala  Phe  Thr  Thr  Lys  Ile
     850                      855                 860

Lys  Asp  Thr  Ser  Leu  Ile  Asp  Leu  Glu  Met  Glu  Asp  Gly  Leu  Asn  Gly
865                      870                      875                      880

Asp  Val  Gly  Thr  Asp  Ala  Asn  Arg  Lys  Lys  Asn  Glu  Ser  Asn  Asp  Ala
               885                      890                           895

Glu  Val  Ser  Glu  Asn  Glu  Asp  Thr  Thr  Gly  Leu  Thr  Ser  Pro  Thr  Arg
               900                 905                      910

Val  Ala  Lys  Ile  Ser  Ser  Asp  Gln  Leu  Glu  Asn  Ala  Leu  Glu  Met  Gly
          915                 920                      925

Arg  Gln  Gln  Asp  Val  Thr  Glu  Cys  Ile  Gly  Asn  Val  Leu  Phe  Gln  Ile
930                      935                      940

Glu  Ser  Gly  Ser  Glu  Pro  Ile  Arg  Tyr  Asp  Glu  Asp  Asn  Glu  Gln  Tyr
945                 950                      955                           960

Asp  Leu  Val  Lys  Gln  Leu  Phe  Tyr  Gly  Thr  Thr  Lys  Gln  Ser  Ile  Val
               965                      970                      975

Pro  Leu  Ser  Ala  Thr  Asn  Lys  Val  Arg  Thr  Lys  Val  Glu  Arg  Phe  Leu
               980                 985                      990

Ser  Leu  Leu  Ile  Asn  Ile  Gly  Asp  His  Pro  Lys  Asp  Ile  Tyr  Asp  Ala
          995                 1000                     1005

Phe  Asp  Ser  Tyr  Phe  Lys  Asp  Glu  Tyr  Leu  Thr  Met  Glu  Glu  Tyr  Gly
     1010                     1015                     1020

Asp  Val  Ile  Arg  Thr  Val  Ala  Val  Thr  Thr  Phe  Pro  Thr  Ile  Leu  Gln
1025                     1030                     1035                     1040

Val  Gln  Ile  Gln  Arg  Val  Tyr  Tyr  Asp  Arg  Glu  Arg  Leu  Met  Pro  Phe
                    1045                     1050                     1055

Lys  Ser  Ile  Glu  Pro  Leu  Pro  Phe  Lys  Glu  Val  Ile  Tyr  Met  Asp  Arg
               1060                     1065                     1070

Tyr  Ala  Asp  Thr  Glu  Asn  Pro  Leu  Leu  Leu  Ala  Lys  Lys  Lys  Glu  Thr
               1075                     1080                     1085

Glu  Glu  Met  Lys  Gln  Lys  Leu  Lys  Val  Met  Lys  Asn  Arg  Gln  Arg  Glu
     1090                     1095                     1100

Leu  Leu  Ser  Arg  Asp  Asp  Ser  Gly  Leu  Thr  Arg  Lys  Asp  Ala  Phe  Leu
1105                     1110                     1115                     1120

Glu  Ser  Ile  Lys  Leu  Leu  Glu  Ser  Asp  Thr  Ile  Lys  Lys  Thr  Pro  Leu
               1125                     1130                     1135

Lys  Ile  Glu  Ala  Ala  Asn  Asp  Val  Ile  Lys  Thr  Leu  Arg  Asn  Asn  Val
               1140                     1145                     1150

Gln  Asn  Ile  Asp  Asn  Glu  Leu  Met  Lys  Leu  Tyr  Asn  Asp  Ile  Asn  Ser
               1155                     1160                     1165

Leu  Glu  Glu  Lys  Ile  Ser  His  Gln  Phe  Asp  Asp  Phe  Lys  Glu  Tyr  Gly
     1170                     1175                     1180

Tyr  Ser  Leu  Phe  Ser  Val  Phe  Ile  His  Arg  Gly  Glu  Ala  Ser  Tyr  Gly
1185                     1190                     1195                     1200

His  Tyr  Trp  Ile  Tyr  Ile  Lys  Asp  Arg  Asn  Arg  Asn  Gly  Ile  Trp  Arg
                    1205                     1210                     1215

Lys  Tyr  Asn  Asp  Glu  Thr  Ile  Ser  Glu  Val  Gln  Glu  Glu  Val  Phe
               1220                     1225                     1230

Asn  Phe  Asn  Glu  Gly  Asn  Thr  Ala  Thr  Pro  Tyr  Phe  Leu  Val  Tyr  Val
     1235                     1240                     1245

Lys  Gln  Gly  Gln  Glu  Gly  Asp  Ile  Glu  Pro  Leu  Lys  Arg  Ile  Leu  Lys
     1250                     1255                     1260
```

(2) INFORMATION FOR SEQ ID NO:7:

( i ) SEQUENCE CHARACTERISTICS:
    ( A ) LENGTH: 4887 base pairs
    ( B ) TYPE: nucleic acid
    ( C ) STRANDEDNESS: double
    ( D ) TOPOLOGY: linear ( i x ) FEATURE:
    ( A ) NAME/KEY: CDS
    ( B ) LOCATION: 1278..4013

( x i ) SEQUENCE DESCRIPTION: SEQ ID NO:7:

```
GCATGCTGAA CATCCTTCTG CAAACAACCT TGCCACATAA CGGGTATACC AGGCAGGCGT      60
TCATCATCAC GCCAACATAT TTCTTGATCA ACAATTGCTT CACAGATGCG GGATTCAAGG     120
GGAAAATGAC CGCCATCAAC GAGCAGGGCC ACGACTCGAT TGATTTCGAG TCGTTGATTT     180
CTGCCCTTGA GCAGCACGAG GCGGAGCCGC AGCCCCATAG TACCACAGAG ATGATTCAGG     240
GGCCAAAGTT GACCAAGAAG GTCTACAGGT ACGTTATGTA CTGCATCCCG ACGTTTGCAA     300
ACCCATCGGG AAACACATAC TCGCTTGAGA CCAGACGCAG ACTTATCGAC ATCGCTCGGA     360
AGTACGACAT GCTGATAATC ACTGATGACG TGTACGATAT TCTAGATTAC ACGACGCCCT     420
CAGATGAGCT GCCCTCTCCG CCCCTAAGGA TGGTGCACAT AGACAGAAGT ACAGCGCCCT     480
CCGGTGAGGA CTCGTTCGGG AATACAGTGT CCAACGCAAC TTTCTCCAAG CTGATCGCCC     540
CTGGGCTCAG ATTTGGATAC CATGAGTCAA TCAACGCGAA TCTCGCCAGA CAGCTATCTA     600
AAGGTGGTGC AAACGTCTCT GGCGGAACTC CCTCACAACT GAACTCCATG ATCGTGGGTG     660
AGATGCTGCG TAGTGGTGCC GCCCAGAGAT GCATTGCACA TCTGAGATCC GTATACTCCG     720
AGAGGGCCAC TGTCTTGACC TCGGCGCTTA AGAAATACAT GCCCCATGGA ACCGAGATTA     780
TGCCATTGAA GGGCGGCTAT TTTACTTGGA TCACTCTCCC ACCAGCGTAC AATGCCATGG     840
AGATATCCAC TATTCTTGCC AAGAAATTTA ATGTCATCCT TGCCGACGGC TCCAATTTCG     900
AGGTCATCGG CGATGAGAAA AACTGGGGTC AGTCATGCTT TAGGCTTTCT ATTAGTTTCT     960
TAGAAGTTGA TGATATCGAC AGGGGCATTG AGCTGTTTGG AGCTGTTTGC AAATCTCATG    1020
CGATCACCAA TAACATAACT ATGTAGAAGG AATACGTATA TAGGTGAACG GTAATAAGAG    1080
GGTAATTTTT CTACGGGCAA AGGCAAGGAA GAAAAGAAA AAGAAGGAAA AAAATATAAT     1140
GTGATAAAAC AAACAAGCAG CGAAAAAGCG AAAGGGAAGA GAAGTGTTCT AGAGAAGAAA    1200
GTCATTTTAA TAGTAAGTCA GACTCGTCTG CTACCATCAT CCAGGTACCG CTTTCCTTTC    1260
CATCATCATT AAAAAAA ATG AAC ATG CAA GAC GCT AAC AAA GAA GAG TCG       1310
                   Met Asn Met Gln Asp Ala Asn Lys Glu Glu Ser
                    1               5                  10

TAC TCG ATG TAC CCG AAA ACC TCT TCT CCA CCA CCA CCT ACG CCA ACC      1358
Tyr Ser Met Tyr Pro Lys Thr Ser Ser Pro Pro Pro Pro Thr Pro Thr
             15                  20                  25

AAT ATG CAG ATT CCT ATT TAT CAA GCG CCT TTG CAG ATG TAC GGC TAC      1406
Asn Met Gln Ile Pro Ile Tyr Gln Ala Pro Leu Gln Met Tyr Gly Tyr
         30                  35                  40

ACT CAG GCC CCA TAT CTA TAC CCC ACA CAA ATA CCT GCC TAT TCG TTT      1454
Thr Gln Ala Pro Tyr Leu Tyr Pro Thr Gln Ile Pro Ala Tyr Ser Phe
         45                  50                  55

AAT ATG GTC AAC CAA AAC CAG CCA ATC TAC CAT CAA AGT GGC AGC CCA      1502
Asn Met Val Asn Gln Asn Gln Pro Ile Tyr His Gln Ser Gly Ser Pro
60                   65                  70                  75

CAT CAC TTG CCT CCG CAA AAC AAT ATT AAC GGC GGA AGC ACT ACC AAT      1550
His His Leu Pro Pro Gln Asn Asn Ile Asn Gly Gly Ser Thr Thr Asn
                 80                  85                  90

AAC AAC AAC ATT AAC AAG AAG AAG TGG CAC TCT AAT GGC ATT ACC AAT      1598
```

|     |     |     |     |     |     |     |     |     |     |     |     |     |     |     |     |
| --- | --- | --- | --- | --- | --- | --- | --- | --- | --- | --- | --- | --- | --- | --- | --- |
| Asn | Asn | Asn | Ile | Asn | Lys | Lys | Lys | Trp | His | Ser | Asn | Gly | Ile | Thr | Asn |
|     |     |     | 95  |     |     |     | 100 |     |     |     |     |     | 105 |     |     |

| AAC | AAT | GGA | AGC | AGC | GGT | AAT | CAA | GGC | GCC | AAC | TCT | AGC | GGT | AGC | GGC | 1646 |
| --- | --- | --- | --- | --- | --- | --- | --- | --- | --- | --- | --- | --- | --- | --- | --- | --- |
| Asn | Asn | Gly | Ser | Ser | Gly | Asn | Gln | Gly | Ala | Asn | Ser | Ser | Gly | Ser | Gly |      |
|     |     | 110 |     |     |     |     | 115 |     |     |     |     | 120 |     |     |     |      |

| ATG | AGC | TAC | AAC | AAA | TCC | CAC | ACC | TAC | CAT | CAC | AAT | TAC | TCT | AAC | AAT | 1694 |
| --- | --- | --- | --- | --- | --- | --- | --- | --- | --- | --- | --- | --- | --- | --- | --- | --- |
| Met | Ser | Tyr | Asn | Lys | Ser | His | Thr | Tyr | His | His | Asn | Tyr | Ser | Asn | Asn |      |
|     | 125 |     |     |     |     | 130 |     |     |     |     | 135 |     |     |     |     |      |

| CAT | ATC | CCC | ATG | ATG | GCC | TCT | CCA | AAC | AGT | GGC | AGC | AAT | GCG | GGC | ATG | 1742 |
| --- | --- | --- | --- | --- | --- | --- | --- | --- | --- | --- | --- | --- | --- | --- | --- | --- |
| His | Ile | Pro | Met | Met | Ala | Ser | Pro | Asn | Ser | Gly | Ser | Asn | Ala | Gly | Met |      |
| 140 |     |     |     | 145 |     |     |     |     | 150 |     |     |     |     |     | 155 |      |

| AAA | AAA | CAG | ACC | AAC | TCT | TCC | AAC | GGC | AAC | GGT | TCT | TCG | GCT | ACT | TCA | 1790 |
| --- | --- | --- | --- | --- | --- | --- | --- | --- | --- | --- | --- | --- | --- | --- | --- | --- |
| Lys | Lys | Gln | Thr | Asn | Ser | Ser | Asn | Gly | Asn | Gly | Ser | Ser | Ala | Thr | Ser |      |
|     |     |     |     | 160 |     |     |     |     | 165 |     |     |     |     | 170 |     |      |

| CCA | TCG | TAC | TCT | TCC | TAC | AAC | TCT | TCT | TCA | CAG | TAT | GAT | TTA | TAC | AAG | 1838 |
| --- | --- | --- | --- | --- | --- | --- | --- | --- | --- | --- | --- | --- | --- | --- | --- | --- |
| Pro | Ser | Tyr | Ser | Ser | Tyr | Asn | Ser | Ser | Ser | Gln | Tyr | Asp | Leu | Tyr | Lys |      |
|     |     |     | 175 |     |     |     |     | 180 |     |     |     |     | 185 |     |     |      |

| TTT | GAT | GTC | ACT | AAA | TTA | AAG | AAT | CTC | AAG | GAA | AAT | TCA | TCA | AAC | TTG | 1886 |
| --- | --- | --- | --- | --- | --- | --- | --- | --- | --- | --- | --- | --- | --- | --- | --- | --- |
| Phe | Asp | Val | Thr | Lys | Leu | Lys | Asn | Leu | Lys | Glu | Asn | Ser | Ser | Asn | Leu |      |
|     |     | 190 |     |     |     |     | 195 |     |     |     |     | 200 |     |     |     |      |

| ATT | CAA | TTG | CCA | CTG | TTC | ATA | AAC | ACT | ACG | GAA | GCA | GAA | TTT | GCT | GCG | 1934 |
| --- | --- | --- | --- | --- | --- | --- | --- | --- | --- | --- | --- | --- | --- | --- | --- | --- |
| Ile | Gln | Leu | Pro | Leu | Phe | Ile | Asn | Thr | Thr | Glu | Ala | Glu | Phe | Ala | Ala |      |
|     | 205 |     |     |     |     | 210 |     |     |     |     | 215 |     |     |     |     |      |

| GCA | AGT | GTC | CAA | AGG | TAC | GAA | TTA | AAC | ATG | AAG | GCT | TTG | AAC | CTA | AAC | 1982 |
| --- | --- | --- | --- | --- | --- | --- | --- | --- | --- | --- | --- | --- | --- | --- | --- | --- |
| Ala | Ser | Val | Gln | Arg | Tyr | Glu | Leu | Asn | Met | Lys | Ala | Leu | Asn | Leu | Asn |      |
| 220 |     |     |     |     | 225 |     |     |     |     | 230 |     |     |     |     | 235 |      |

| TCT | GAA | AGC | TTA | GAG | AAC | TCA | TCT | GTA | GAA | AAG | AGC | TCT | GCC | CAT | CAT | 2030 |
| --- | --- | --- | --- | --- | --- | --- | --- | --- | --- | --- | --- | --- | --- | --- | --- | --- |
| Ser | Glu | Ser | Leu | Glu | Asn | Ser | Ser | Val | Glu | Lys | Ser | Ser | Ala | His | His |      |
|     |     |     |     | 240 |     |     |     |     | 245 |     |     |     |     | 250 |     |      |

| CAC | ACA | AAA | AGC | CAT | AGT | ATA | CCA | AAG | CAT | AAT | GAG | GAA | GTA | AAG | ACA | 2078 |
| --- | --- | --- | --- | --- | --- | --- | --- | --- | --- | --- | --- | --- | --- | --- | --- | --- |
| His | Thr | Lys | Ser | His | Ser | Ile | Pro | Lys | His | Asn | Glu | Glu | Val | Lys | Thr |      |
|     |     |     | 255 |     |     |     |     | 260 |     |     |     |     | 265 |     |     |      |

| GAA | ACA | CAT | GGG | GAA | GAA | GAA | GAT | GCT | CAT | GAT | AAA | AAA | CCA | CAT | GCG | 2126 |
| --- | --- | --- | --- | --- | --- | --- | --- | --- | --- | --- | --- | --- | --- | --- | --- | --- |
| Glu | Thr | His | Gly | Glu | Glu | Glu | Asp | Ala | His | Asp | Lys | Lys | Pro | His | Ala |      |
|     |     | 270 |     |     |     |     | 275 |     |     |     |     | 280 |     |     |     |      |

| AGC | AAA | GAT | GCG | CAC | GAG | CTT | AAA | AAG | AAA | ACT | GAA | GTA | AAG | AAA | GAG | 2174 |
| --- | --- | --- | --- | --- | --- | --- | --- | --- | --- | --- | --- | --- | --- | --- | --- | --- |
| Ser | Lys | Asp | Ala | His | Glu | Leu | Lys | Lys | Lys | Thr | Glu | Val | Lys | Lys | Glu |      |
|     | 285 |     |     |     |     | 290 |     |     |     |     | 295 |     |     |     |     |      |

| GAT | GCT | AAG | CAA | GAC | CGT | AAC | GAA | AAA | GTT | ATA | CAG | GAA | CCT | CAA | GCT | 2222 |
| --- | --- | --- | --- | --- | --- | --- | --- | --- | --- | --- | --- | --- | --- | --- | --- | --- |
| Asp | Ala | Lys | Gln | Asp | Arg | Asn | Glu | Lys | Val | Ile | Gln | Glu | Pro | Gln | Ala |      |
| 300 |     |     |     |     | 305 |     |     |     |     | 310 |     |     |     |     | 315 |      |

| ACT | GTT | TTA | CCT | GTA | GTG | GAT | AAG | AAG | GAA | CCA | GAG | GAA | TCT | GTT | GAA | 2270 |
| --- | --- | --- | --- | --- | --- | --- | --- | --- | --- | --- | --- | --- | --- | --- | --- | --- |
| Thr | Val | Leu | Pro | Val | Val | Asp | Lys | Lys | Glu | Pro | Glu | Glu | Ser | Val | Glu |      |
|     |     |     |     | 320 |     |     |     |     | 325 |     |     |     |     | 330 |     |      |

| GAA | AAT | ACT | TCC | AAG | ACA | TCT | TCA | CCT | TCA | CCA | TCT | CCT | CCA | GCA | GCA | 2318 |
| --- | --- | --- | --- | --- | --- | --- | --- | --- | --- | --- | --- | --- | --- | --- | --- | --- |
| Glu | Asn | Thr | Ser | Lys | Thr | Ser | Ser | Pro | Ser | Pro | Ser | Pro | Pro | Ala | Ala |      |
|     |     |     | 335 |     |     |     |     | 340 |     |     |     |     | 345 |     |     |      |

| AAA | TCC | TGG | TCC | GCC | ATA | GCA | TCA | GAT | GCG | ATT | AAA | AGT | AGA | CAA | GCT | 2366 |
| --- | --- | --- | --- | --- | --- | --- | --- | --- | --- | --- | --- | --- | --- | --- | --- | --- |
| Lys | Ser | Trp | Ser | Ala | Ile | Ala | Ser | Asp | Ala | Ile | Lys | Ser | Arg | Gln | Ala |      |
|     |     | 350 |     |     |     |     | 355 |     |     |     |     | 360 |     |     |     |      |

| AGT | AAC | AAA | ACA | GTC | TCC | GGA | TCG | ATG | GTC | ACT | AAA | ACA | CCA | ATT | TCT | 2414 |
| --- | --- | --- | --- | --- | --- | --- | --- | --- | --- | --- | --- | --- | --- | --- | --- | --- |
| Ser | Asn | Lys | Thr | Val | Ser | Gly | Ser | Met | Val | Thr | Lys | Thr | Pro | Ile | Ser |      |
|     | 365 |     |     |     |     | 370 |     |     |     |     | 375 |     |     |     |     |      |

| GGT | ACG | ACC | GCA | GGC | GTT | TCA | TCA | ACA | AAC | ATG | GCT | GCG | GCG | ACT | ATA | 2462 |
| --- | --- | --- | --- | --- | --- | --- | --- | --- | --- | --- | --- | --- | --- | --- | --- | --- |
| Gly | Thr | Thr | Ala | Gly | Val | Ser | Ser | Thr | Asn | Met | Ala | Ala | Ala | Thr | Ile |      |
| 380 |     |     |     |     | 385 |     |     |     |     | 390 |     |     |     |     | 395 |      |

| GGT | AAA | TCC | AGC | TCT | CCC | CTG | TTG | TCC | AAG | CAG | CCT | CAG | AAA | AAG | GAT | 2510 |
| --- | --- | --- | --- | --- | --- | --- | --- | --- | --- | --- | --- | --- | --- | --- | --- | --- |
| Gly | Lys | Ser | Ser | Ser | Pro | Leu | Leu | Ser | Lys | Gln | Pro | Gln | Lys | Lys | Asp |      |
|     |     |     |     | 400 |     |     |     |     | 405 |     |     |     |     | 410 |     |      |

| AAA | AAA | TAC | GTT | CCA | CCT | TCT | ACA | AAG | GGT | ATT | GAG | CCA | CTG | GGT | TCG | 2558 |
| --- | --- | --- | --- | --- | --- | --- | --- | --- | --- | --- | --- | --- | --- | --- | --- | --- |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Lys | Lys | Tyr | Val<br>415 | Pro | Pro | Ser | Thr | Lys<br>420 | Gly | Ile | Glu | Pro | Leu<br>425 | Gly | Ser |      |
| ATT | GCG | TTA | AGA | ATG | TGT | TTT | GAT | CCC | GAT | TTC | ATT | AGT | TAC | GTT | TTA | 2606 |
| Ile | Ala | Leu<br>430 | Arg | Met | Cys | Phe | Asp<br>435 | Pro | Asp | Phe | Ile | Ser<br>440 | Tyr | Val | Leu |      |
| CGG | AAT | AAA | GAT | GTT | GAA | AAC | AAA | ATA | CCA | GTC | CAT | TCC | ATT | ATT | CCA | 2654 |
| Arg | Asn<br>445 | Lys | Asp | Val | Glu | Asn<br>450 | Lys | Ile | Pro | Val | His<br>455 | Ser | Ile | Ile | Pro |      |
| AGA | GGC | ATA | ATT | AAC | AGA | GCC | AAC | ATT | TGT | TTT | ATG | AGT | TCT | GTG | TTA | 2702 |
| Arg<br>460 | Gly | Ile | Ile | Asn | Arg<br>465 | Ala | Asn | Ile | Cys | Phe<br>470 | Met | Ser | Ser | Val | Leu<br>475 |      |
| CAA | GTG | TTA | CTC | TAC | TGT | AAG | CCA | TTT | ATT | GAT | GTA | ATT | AAC | GTT | CTC | 2750 |
| Gln | Val | Leu | Leu | Tyr<br>480 | Cys | Lys | Pro | Phe | Ile<br>485 | Asp | Val | Ile | Asn | Val<br>490 | Leu |      |
| AGT | ACA | CGG | AAT | ACC | AAT | TCA | AGA | GTC | GGC | ACA | TCA | TCC | TGT | AAA | TTA | 2798 |
| Ser | Thr | Arg | Asn<br>495 | Thr | Asn | Ser | Arg | Val<br>500 | Gly | Thr | Ser | Ser<br>505 | Cys | Lys | Leu |      |
| TTA | GAT | GCT | TGT | TTG | ACT | ATG | TAT | AAG | CAA | TTC | GAT | AAG | GAA | ACC | TAT | 2846 |
| Leu | Asp | Ala<br>510 | Cys | Leu | Thr | Met | Tyr<br>515 | Lys | Gln | Phe | Asp | Lys<br>520 | Glu | Thr | Tyr |      |
| GAG | AAA | AAA | TTC | CTA | GAG | AAT | GCT | GAT | GAT | GCT | GAA | AAA | ACC | ACG | GAA | 2894 |
| Glu | Lys<br>525 | Lys | Phe | Leu | Glu | Asn<br>530 | Ala | Asp | Asp | Ala | Glu<br>535 | Lys | Thr | Thr | Glu |      |
| AGT | GAT | GCA | AAA | AAA | TCA | TCA | AAA | TCC | AAG | AGT | TTC | CAA | CAC | TGC | GCC | 2942 |
| Ser<br>540 | Asp | Ala | Lys | Lys | Ser<br>545 | Ser | Lys | Ser | Lys | Ser<br>550 | Phe | Gln | His | Cys | Ala<br>555 |      |
| ACT | GCC | GAT | GCT | GTC | AAA | CCT | GAC | GAA | TTT | TAC | AAA | ACT | TTG | TCT | ACT | 2990 |
| Thr | Ala | Asp | Ala | Val<br>560 | Lys | Pro | Asp | Glu | Phe<br>565 | Tyr | Lys | Thr | Leu | Ser<br>570 | Thr |      |
| ATA | CCG | AAG | TTC | AAA | GAC | TTG | CAA | TGG | GGC | CAT | CAG | GAA | GAC | GCA | GAA | 3038 |
| Ile | Pro | Lys | Phe<br>575 | Lys | Asp | Leu | Gln | Trp<br>580 | Gly | His | Gln | Glu | Asp<br>585 | Ala | Glu |      |
| GAA | TTT | TTG | ACC | CAC | TTA | TTG | GAC | CAA | TTA | CAC | GAG | GAA | TTA | ATT | TCT | 3086 |
| Glu | Phe | Leu<br>590 | Thr | His | Leu | Leu | Asp<br>595 | Gln | Leu | His | Glu | Glu<br>600 | Leu | Ile | Ser |      |
| GCA | ATT | GAT | GGC | TTA | ACC | GAT | AAT | GAA | ATT | CAA | AAT | ATG | CTG | CAA | AGT | 3134 |
| Ala | Ile | Asp<br>605 | Gly | Leu | Thr | Asp | Asn<br>610 | Glu | Ile | Gln | Asn | Met<br>615 | Leu | Gln | Ser |      |
| ATT | AAT | GAT | GAA | CAA | TTG | AAA | GTT | TTC | TTT | ATT | AGA | AAT | TTG | TCA | CGT | 3182 |
| Ile | Asn | Asp<br>620 | Glu | Gln | Leu | Lys<br>625 | Val | Phe | Phe | Ile | Arg<br>630 | Asn | Leu | Ser | Arg<br>635 |      |
| TAT | GGA | AAA | GCA | GAG | TTT | ATC | AAA | AAT | GCT | AGT | CCT | AGA | CTG | AAG | GAG | 3230 |
| Tyr | Gly | Lys | Ala | Glu<br>640 | Phe | Ile | Lys | Asn | Ala<br>645 | Ser | Pro | Arg | Leu | Lys<br>650 | Glu |      |
| TTG | ATA | GAA | AAA | TAT | GGC | GTG | ATC | AAT | GAT | GAC | TCT | ACC | GAA | GAA | AAT | 3278 |
| Leu | Ile | Glu | Lys<br>655 | Tyr | Gly | Val | Ile | Asn<br>640 | Asp | Asp | Ser | Thr | Glu<br>665 | Glu | Asn |      |
| GGT | TGG | CAT | GAA | GTG | AGC | GGA | TCT | AGC | AAA | AGA | GGC | AAG | AAA | ACT | AAG | 3326 |
| Gly | Trp | His<br>670 | Glu | Val | Ser | Gly | Ser<br>675 | Ser | Lys | Arg | Gly | Lys<br>680 | Lys | Thr | Lys |      |
| ACC | GCT | GCC | AAG | AGG | ACT | GTC | GAG | ATT | GTT | CCA | TCA | CCA | ATC | TCC | AAA | 3374 |
| Thr | Ala<br>685 | Ala | Lys | Arg | Thr | Val<br>690 | Glu | Ile | Val | Pro | Ser<br>695 | Pro | Ile | Ser | Lys |      |
| CTT | TTC | GGT | GGC | CAG | TTC | AGA | TCT | GTG | TTA | GAT | ATA | CCG | AAC | AAT | AAG | 3422 |
| Leu | Phe | Gly | Gly | Gln<br>705 | Phe | Arg | Ser | Val | Leu<br>710 | Asp | Ile | Pro | Asn | Asn<br>715 | Lys |      |
| Leu<br>700 |     |     |     |     |     |     |     |     |     |     |     |     |     |     |     |      |
| GAA | TCT | CAA | TCG | ATT | ACA | CTC | GAT | CCG | TTC | CAA | ACA | ATT | CAA | TTG | GAC | 3470 |
| Glu | Ser | Gln | Ser | Ile<br>720 | Thr | Leu | Asp | Pro | Phe<br>725 | Gln | Thr | Ile | Gln | Leu<br>730 | Asp |      |
| ATT | TCA | GAT | GCT | GGT | GTG | AAT | GAT | CTA | GAA | ACT | GCA | TTC | AAA | AAA | TTT | 3518 |

|  |  |  |  |  |  |  |  |  |  |  |  |  |  |  |  |
|--|--|--|--|--|--|--|--|--|--|--|--|--|--|--|--|
| Ile | Ser | Asp | Ala<br>735 | Gly | Val | Asn | Asp | Leu<br>740 | Glu | Thr | Ala | Phe | Lys<br>745 | Lys | Phe |

| AGT | GAA | TAC | GAA | TTG | CTA | CCC | TTT | AAG | TCC | TCG | TCA | GGG | AAT | GAT | GTC | 3566 |
|--|--|--|--|--|--|--|--|--|--|--|--|--|--|--|--|--|
| Ser | Glu | Tyr<br>750 | Glu | Leu | Leu | Pro | Phe<br>755 | Lys | Ser | Ser | Ser | Gly<br>760 | Asn | Asp | Val |  |

| GAG | GCC | AAG | AAG | CAG | ACT | TTT | ATT | GAT | AAA | TTG | CCG | CAA | GTT | CTT | TTA | 3614 |
|--|--|--|--|--|--|--|--|--|--|--|--|--|--|--|--|--|
| Glu | Ala<br>765 | Lys | Lys | Gln | Thr | Phe<br>770 | Ile | Asp | Lys | Leu | Pro<br>775 | Gln | Val | Leu | Leu |  |

| ATC | CAA | TTC | AAA | AGA | TTC | TCA | TTC | ATA | AAT | AAT | GTG | AAC | AAA | GAC | AAC | 3662 |
|--|--|--|--|--|--|--|--|--|--|--|--|--|--|--|--|--|
| Ile<br>780 | Gln | Phe | Lys | Arg | Phe<br>785 | Ser | Phe | Ile | Asn | Asn<br>790 | Val | Asn | Lys | Asp | Asn<br>795 |  |

| GCA | ATG | ACG | AAC | TAT | AAC | GCG | TAC | AAT | GGA | CGT | ATT | GAG | AAG | ATC | AGG | 3710 |
|--|--|--|--|--|--|--|--|--|--|--|--|--|--|--|--|--|
| Ala | Met | Thr | Asn | Tyr<br>800 | Asn | Ala | Tyr | Asn | Gly<br>805 | Arg | Ile | Glu | Lys | Ile<br>810 | Arg |  |

| AAA | AAA | ATT | AAA | TAT | GGT | CAC | GAG | TTA | ATC | ATA | CCT | GAA | GAA | TCA | ATG | 3758 |
|--|--|--|--|--|--|--|--|--|--|--|--|--|--|--|--|--|
| Lys | Lys | Ile | Lys<br>815 | Tyr | Gly | His | Glu | Leu<br>820 | Ile | Ile | Pro | Glu | Glu<br>825 | Ser | Met |  |

| TCT | TCC | ATA | ACA | TTG | AAA | AAC | AAC | ACC | TCA | GGG | ATT | GAT | GAT | AGA | AGA | 3806 |
|--|--|--|--|--|--|--|--|--|--|--|--|--|--|--|--|--|
| Ser | Ser | Ile<br>830 | Thr | Leu | Lys | Asn | Asn<br>835 | Thr | Ser | Gly | Ile | Asp<br>840 | Asp | Arg | Arg |  |

| TAT | AAG | CTA | ACC | GGA | GTT | ATA | TAC | CAT | CAT | GGG | GTA | AGT | TCC | GAT | GGC | 3854 |
|--|--|--|--|--|--|--|--|--|--|--|--|--|--|--|--|--|
| Tyr | Lys<br>845 | Leu | Thr | Gly | Val | Ile<br>850 | Tyr | His | His | Gly | Val<br>855 | Ser | Ser | Asp | Gly |  |

| GGT | CAT | TAC | ACA | GCG | GAT | GTT | TAT | CAT | AGC | GAG | CAC | AAC | AAA | TGG | TAT | 3902 |
|--|--|--|--|--|--|--|--|--|--|--|--|--|--|--|--|--|
| Gly<br>860 | His | Tyr | Thr | Ala | Asp<br>865 | Val | Tyr | His | Ser | Glu<br>870 | His | Asn | Lys | Trp | Tyr<br>875 |  |

| AGA | ATA | GAT | GAT | GTA | AAT | ATT | ACC | GAA | CTA | GAG | GAC | GAT | GAC | GTT | TTG | 3950 |
|--|--|--|--|--|--|--|--|--|--|--|--|--|--|--|--|--|
| Arg | Ile | Asp | Asp | Val<br>880 | Asn | Ile | Thr | Glu | Leu<br>885 | Glu | Asp | Asp | Asp | Val<br>890 | Leu |  |

| AAA | GGT | GGC | GAA | GAA | GCT | TCT | GAT | TCG | AGG | ACT | GCC | TAT | ATT | TTA | ATG | 3998 |
|--|--|--|--|--|--|--|--|--|--|--|--|--|--|--|--|--|
| Lys | Gly | Gly | Glu<br>895 | Glu | Ala | Ser | Asp | Ser<br>900 | Arg | Thr | Ala | Tyr | Ile<br>905 | Leu | Met |  |

| TAT | CAA | AAG | AGA | AAT | TAAGACGGGG | GGTGGTATTA | TAGACAAAAT | ACATAAAAAA | 4053 |
|--|--|--|--|--|--|--|--|--|--|
| Tyr | Gln | Lys<br>910 | Arg | Asn |  |  |  |  |  |

| TAATATAGCA | ATAATACAAT | ACAATACAAT | ACAATACGAT | AGTGAGCACG | ATTTTAAAAA | 4113 |
|--|--|--|--|--|--|--|
| AGAAATAGAG | ACAGACAGAG | AAACAGAGTT | ACACTTTATG | CTTGGCATAT | TTAAAAAATG | 4173 |
| ATTTCGCCCA | GGATCGAACT | GGGGACGTTC | TGCGTGTTAA | GCAGATGCCA | TAACCGACTA | 4233 |
| GACCACGAAA | CCAATTATTT | CTTGGAGATG | AACATTTAAG | AAACAAATAC | CTTGTAGAAG | 4293 |
| GAATGTGAAT | TTCAAAATAT | TATGGCCTTT | GGCAACAATG | GAATCACAAC | AATTATCACA | 4353 |
| AAACTCATAC | ATCTCTTAAG | ATTCATTTCT | TACTTTAAGT | AATCATCCAA | ATTTAGCCAA | 4413 |
| AGTTTGATTT | TACCTAAAAA | AAGCAGAGGA | TTCCCGATTT | CAATCATATG | TGCACAGACG | 4473 |
| ATGAGTCCAA | CACGTTATCG | TTAACATAGT | GCTCAATATT | GCCACTGCGC | TTCGCAGGAG | 4533 |
| CATATTTCGT | ATACGCCAAG | CCCAAGGAGG | GTTTGTCAT | TAAGCAGCTT | ACGCCAATTA | 4593 |
| AGTGCTAACC | TCGAAGCACC | ATACTTTATC | TCAGGATTTA | CAAACTCCCT | ATTGCACAAC | 4653 |
| GGCAAACAAC | ATAATCATGA | CCAAATGGGT | AAAAAGATG | AGCTGTGAAA | AAGCCAAAAA | 4713 |
| AAAAAAGGAA | GAACTAGAAT | TACATTTATT | ATTCTACACA | CAAAAAGAAA | AAATAGTTTC | 4773 |
| TTTATTTAAA | TGATTTGAAG | AAAAAGAACT | ATAACGACTA | CATCGAAGAA | TACAATATTA | 4833 |
| GTAAAAAACA | CATGTCCTGT | TTAAAATAAG | TCTCTAGTTA | AAGACTATTC | GATC | 4887 |

( 2 ) INFORMATION FOR SEQ ID NO:8:

( i ) SEQUENCE CHARACTERISTICS:
        ( A ) LENGTH: 912 amino acids (B) TYPE: amino acid
(D) TOPOLOGY: linear (ii) MOLECULE TYPE: protein (xi) SEQUENCE DESCRIPTION: SEQ ID NO:8:

```
Met Asn Met Gln Asp Ala Asn Lys Glu Glu Ser Tyr Ser Met Tyr Pro
  1               5                  10                  15
Lys Thr Ser Ser Pro Pro Pro Thr Pro Thr Asn Met Gln Ile Pro
             20                  25                  30
Ile Tyr Gln Ala Pro Leu Gln Met Tyr Gly Tyr Thr Gln Ala Pro Tyr
         35                  40                  45
Leu Tyr Pro Thr Gln Ile Pro Ala Tyr Ser Phe Asn Met Val Asn Gln
         50                  55                  60
Asn Gln Pro Ile Tyr His Gln Ser Gly Ser Pro His His Leu Pro Pro
 65                  70                  75                  80
Gln Asn Asn Ile Asn Gly Gly Ser Thr Thr Asn Asn Asn Asn Ile Asn
                 85                  90                  95
Lys Lys Lys Trp His Ser Asn Gly Ile Thr Asn Asn Asn Gly Ser Ser
                100                 105                 110
Gly Asn Gln Gly Ala Asn Ser Ser Gly Ser Gly Met Ser Tyr Asn Lys
            115                 120                 125
Ser His Thr Tyr His His Asn Tyr Ser Asn Asn His Ile Pro Met Met
    130                 135                 140
Ala Ser Pro Asn Ser Gly Ser Asn Ala Gly Met Lys Lys Gln Thr Asn
145                 150                 155                 160
Ser Ser Asn Gly Asn Gly Ser Ser Ala Thr Ser Pro Ser Tyr Ser Ser
                165                 170                 175
Tyr Asn Ser Ser Ser Gln Tyr Asp Leu Tyr Lys Phe Asp Val Thr Lys
                180                 185                 190
Leu Lys Asn Leu Lys Glu Asn Ser Ser Asn Leu Ile Gln Leu Pro Leu
            195                 200                 205
Phe Ile Asn Thr Thr Glu Ala Glu Phe Ala Ala Ala Ser Val Gln Arg
    210                 215                 220
Tyr Glu Leu Asn Met Lys Ala Leu Asn Leu Asn Ser Glu Ser Leu Glu
225                 230                 235                 240
Asn Ser Ser Val Glu Lys Ser Ser Ala His His His Thr Lys Ser His
                245                 250                 255
Ser Ile Pro Lys His Asn Glu Glu Val Lys Thr Glu Thr His Gly Glu
            260                 265                 270
Glu Glu Asp Ala His Asp Lys Lys Pro His Ala Ser Lys Asp Ala His
    275                 280                 285
Glu Leu Lys Lys Lys Thr Glu Val Lys Lys Glu Asp Ala Lys Gln Asp
290                 295                 300
Arg Asn Glu Lys Val Ile Gln Glu Pro Gln Ala Thr Val Leu Pro Val
305                 310                 315                 320
Val Asp Lys Lys Glu Pro Glu Glu Ser Val Glu Glu Asn Thr Ser Lys
                325                 330                 335
Thr Ser Ser Pro Ser Pro Ser Pro Pro Ala Ala Lys Ser Trp Ser Ala
            340                 345                 350
Ile Ala Ser Asp Ala Ile Lys Ser Arg Gln Ala Ser Asn Lys Thr Val
    355                 360                 365
Ser Gly Ser Met Val Thr Lys Thr Pro Ile Ser Gly Thr Thr Ala Gly
    370                 375                 380
Val Ser Ser Thr Asn Met Ala Ala Ala Thr Ile Gly Lys Ser Ser Ser
```

```
                385                     390                     395                     400
Pro  Leu  Leu  Ser  Lys  Gln  Pro  Gln  Lys  Lys  Asp  Lys  Lys  Tyr  Val  Pro
               405                     410                     415
Pro  Ser  Thr  Lys  Gly  Ile  Glu  Pro  Leu  Gly  Ser  Ile  Ala  Leu  Arg  Met
               420                     425                     430
Cys  Phe  Asp  Pro  Asp  Phe  Ile  Ser  Tyr  Val  Leu  Arg  Asn  Lys  Asp  Val
               435                     440                     445
Glu  Asn  Lys  Ile  Pro  Val  His  Ser  Ile  Ile  Pro  Arg  Gly  Ile  Ile  Asn
     450                     455                     460
Arg  Ala  Asn  Ile  Cys  Phe  Met  Ser  Ser  Val  Leu  Gln  Val  Leu  Leu  Tyr
465                      470                     475                     480
Cys  Lys  Pro  Phe  Ile  Asp  Val  Ile  Asn  Val  Leu  Ser  Thr  Arg  Asn  Thr
               485                     490                     495
Asn  Ser  Arg  Val  Gly  Thr  Ser  Ser  Cys  Lys  Leu  Leu  Asp  Ala  Cys  Leu
               500                     505                     510
Thr  Met  Tyr  Lys  Gln  Phe  Asp  Lys  Glu  Thr  Tyr  Glu  Lys  Lys  Phe  Leu
               515                     520                     525
Glu  Asn  Ala  Asp  Asp  Ala  Glu  Lys  Thr  Thr  Glu  Ser  Asp  Ala  Lys  Lys
     530                     535                     540
Ser  Ser  Lys  Ser  Lys  Ser  Phe  Gln  His  Cys  Ala  Thr  Ala  Asp  Ala  Val
545                      550                     555                     560
Lys  Pro  Asp  Glu  Phe  Tyr  Lys  Thr  Leu  Ser  Thr  Ile  Pro  Lys  Phe  Lys
               565                     570                     575
Asp  Leu  Gln  Trp  Gly  His  Gln  Glu  Asp  Ala  Glu  Glu  Phe  Leu  Thr  His
               580                     585                     590
Leu  Leu  Asp  Gln  Leu  His  Glu  Glu  Leu  Ile  Ser  Ala  Ile  Asp  Gly  Leu
               595                     600                     605
Thr  Asp  Asn  Glu  Ile  Gln  Asn  Met  Leu  Gln  Ser  Ile  Asn  Asp  Glu  Gln
     610                     615                     620
Leu  Lys  Val  Phe  Phe  Ile  Arg  Asn  Leu  Ser  Arg  Tyr  Gly  Lys  Ala  Glu
625                      630                     635                     640
Phe  Ile  Lys  Asn  Ala  Ser  Pro  Arg  Leu  Lys  Glu  Leu  Ile  Glu  Lys  Tyr
               645                     650                     655
Gly  Val  Ile  Asn  Asp  Asp  Ser  Thr  Glu  Glu  Asn  Gly  Trp  His  Glu  Val
               660                     665                     670
Ser  Gly  Ser  Ser  Lys  Arg  Gly  Lys  Lys  Thr  Lys  Thr  Ala  Ala  Lys  Arg
               675                     680                     685
Thr  Val  Glu  Ile  Val  Pro  Ser  Pro  Ile  Ser  Lys  Leu  Phe  Gly  Gly  Gln
     690                     695                     700
Phe  Arg  Ser  Val  Leu  Asp  Ile  Pro  Asn  Asn  Lys  Glu  Ser  Gln  Ser  Ile
705                      710                     715                     720
Thr  Leu  Asp  Pro  Phe  Gln  Thr  Ile  Gln  Leu  Asp  Ile  Ser  Asp  Ala  Gly
               725                     730                     735
Val  Asn  Asp  Leu  Glu  Thr  Ala  Phe  Lys  Lys  Phe  Ser  Glu  Tyr  Glu  Leu
               740                     745                     750
Leu  Pro  Phe  Lys  Ser  Ser  Ser  Gly  Asn  Asp  Val  Glu  Ala  Lys  Lys  Gln
               755                     760                     765
Thr  Phe  Ile  Asp  Lys  Leu  Pro  Gln  Val  Leu  Leu  Ile  Gln  Phe  Lys  Arg
     770                     775                     780
Phe  Ser  Phe  Ile  Asn  Asn  Val  Asn  Lys  Asp  Asn  Ala  Met  Thr  Asn  Tyr
785                      790                     795                     800
Asn  Ala  Tyr  Asn  Gly  Arg  Ile  Glu  Lys  Ile  Arg  Lys  Lys  Ile  Lys  Tyr
               805                     810                     815
```

-continued

```
Gly His Glu Leu Ile Ile Pro Glu Glu Ser Met Ser Ser Ile Thr Leu
            820                 825                     830

Lys Asn Asn Thr Ser Gly Ile Asp Asp Arg Arg Tyr Lys Leu Thr Gly
        835                 840                 845

Val Ile Tyr His His Gly Val Ser Ser Asp Gly Gly His Tyr Thr Ala
    850                 855                 860

Asp Val Tyr His Ser Glu His Asn Lys Trp Tyr Arg Ile Asp Asp Val
865                 870                 875                     880

Asn Ile Thr Glu Leu Glu Asp Asp Asp Val Leu Lys Gly Gly Glu Glu
            885                 890                     895

Ala Ser Asp Ser Arg Thr Ala Tyr Ile Leu Met Tyr Gln Lys Arg Asn
            900                 905                     910
```

( 2 ) INFORMATION FOR SEQ ID NO:9:

( i ) SEQUENCE CHARACTERISTICS:
   ( A ) LENGTH: 4 amino acids
   ( B ) TYPE: amino acid
   ( D ) TOPOLOGY: linear ( x i ) SEQUENCE DESCRIPTION: SEQ ID NO:9:

```
Gly Gly Gly Ser
 1
```